United States Patent
Mahajan et al.

(10) Patent No.: US 10,940,401 B2
(45) Date of Patent: Mar. 9, 2021

(54) METHOD FOR CHROMATOGRAPHY REUSE

(71) Applicant: Genentech, Inc., South San Francisco, CA (US)

(72) Inventors: Ekta Mahajan, South San Francisco, CA (US); Joanna So, South San Francisco, CA (US); Jay Werber, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 279 days.

(21) Appl. No.: 15/920,237

(22) Filed: Mar. 13, 2018

(65) Prior Publication Data

US 2019/0054396 A1 Feb. 21, 2019

Related U.S. Application Data

(63) Continuation of application No. 14/479,092, filed on Sep. 5, 2014, now abandoned.

(60) Provisional application No. 61/874,305, filed on Sep. 5, 2013.

(51) Int. Cl.
*B01D 15/20* (2006.01)
*B01J 49/60* (2017.01)
*B01D 15/38* (2006.01)
*C07K 1/18* (2006.01)
*C07K 1/22* (2006.01)

(52) U.S. Cl.
CPC ....... *B01D 15/203* (2013.01); *B01D 15/3809* (2013.01); *B01J 49/60* (2017.01); *C07K 1/18* (2013.01); *C07K 1/22* (2013.01)

(58) Field of Classification Search
CPC .... B01D 15/203; B01D 15/3809; B01J 49/60; C07K 1/18; C07K 1/22
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 5,208,020 A | 5/1993 | Chari et al. | |
| 5,229,275 A | 7/1993 | Goroff | |
| 5,500,362 A | 3/1996 | Robinson et al. | |
| 5,534,615 A | 7/1996 | Baker et al. | |
| 5,545,807 A | 8/1996 | Surani et al. | |
| 5,565,332 A | 10/1996 | Hoogenboom et al. | |
| 5,567,610 A | 10/1996 | Borrebaeck et al. | |
| 5,571,894 A | 11/1996 | Wels et al. | |
| 5,573,905 A | 11/1996 | Lerner et al. | |
| 5,587,458 A | 12/1996 | King et al. | |
| 5,589,369 A | 12/1996 | Seidman et al. | |
| 5,591,669 A | 1/1997 | Krimpenfort et al. | |
| 5,641,870 A | 6/1997 | Rinderknecht et al. | |
| 5,693,780 A | 12/1997 | Newman et al. | |
| 5,712,374 A | 1/1998 | Kuntsmann et al. | |
| 5,731,168 A | 3/1998 | Carter et al. | |
| 5,821,337 A | 10/1998 | Carter et al. | |
| 7,521,541 B2 | 4/2009 | Eigenbrot et al. | |
| 9,447,188 B2 | 9/2016 | Koncilja et al. | |
| 2004/0101524 A1 | 5/2004 | Qin et al. | |
| 2005/0038231 A1 | 2/2005 | Fahrner et al. | |
| 2005/0056592 A1 | 3/2005 | Braunger et al. | |
| 2006/0067930 A1 | 3/2006 | Adams et al. | |
| 2006/0102561 A1 | 5/2006 | Larsen et al. | |
| 2007/0093399 A1 | 4/2007 | Hamilton et al. | |
| 2008/0230478 A1* | 9/2008 | Johansson | C07K 1/22 210/656 |
| 2009/0105465 A1* | 4/2009 | Arunakumari | C07K 16/2878 530/416 |
| 2011/0065901 A1 | 3/2011 | Soice et al. | |
| 2012/0282654 A1 | 11/2012 | Yao et al. | |
| 2013/0046080 A1 | 2/2013 | Jeon et al. | |
| 2014/0072585 A1 | 3/2014 | Herigstad et al. | |
| 2014/0228548 A1 | 8/2014 | Galperina | |
| 2016/0193633 A1 | 7/2016 | Bian et al. | |

FOREIGN PATENT DOCUMENTS

| | | | |
|---|---|---|---|
| CN | 1771080 A | 5/2006 |
| CN | 101838215 A | 9/2010 |
| CN | 101914433 A | 12/2010 |
| EP | 0 308 936 A2 | 3/1989 |
| EP | 0 404 097 A2 | 12/1990 |
| EP | 1 506 809 A1 | 2/2005 |
| JP | 2006-510356 A | 3/2006 |
| JP | 2006-525496 A | 11/2006 |
| JP | 2007-526897 A | 9/2007 |
| JP | 2008-542710 A | 11/2008 |
| JP | 2010-516773 A | 5/2010 |

(Continued)

OTHER PUBLICATIONS

Albrecht et al. (2009). "Fundamentals of antibody-related therapy and diagnostics," *Drugs Today (Barc.)* 45:199-211.
Brennan et al. "Preparation of bispecific antibodies by chemical recombination of monoclonal immunoglobulin G₁ fragments" Science 229(4708):81-83 (Jul. 5, 1985).
Brodeur et al. (1987). Monoclonal Antibody Production Techniques and Applications New York:NY, Marcel Dekker, Inc., pp. 51-63.
Bruggermann et al., "Designer mice: The production of human antibody repertoires in transgenic animals" Generation of Antibodies by Cell and Gene Immortalization:the Year in Immunology 7:33-40 (1993).
Capel et al., "Heterogeneity of human IgG Fc receptors" Immunomethods 4:25-34 (1994).
Caron et al., "Engineered Humanized Dimeric Forms of IgG are More Effective Antibodies" J Exp Med 176:1191-1195 (Oct. 1992).
Carter et al., "Humanization of an anti-p185 HER2 antibody for human cancer therapy" PNAS 89:4285-4289 (May 1992).

(Continued)

*Primary Examiner* — Daniel E Kolker
*Assistant Examiner* — James L Rogers
(74) *Attorney, Agent, or Firm* — Morrison & Foerster LLP

(57) ABSTRACT

The present invention provides methods for cleaning or regenerating a chromatography materiel for reuse. The methods of the invention can be used for cleaning or regenerating chromatography columns for reuse in the large-scale manufacture of multiple polypeptide products.

36 Claims, 22 Drawing Sheets

(56) References Cited

FOREIGN PATENT DOCUMENTS

| | | |
|---|---|---|
| JP | 2013-501721 A | 1/2013 |
| JP | 2013-514073 A | 4/2013 |
| WO | WO-91/00360 A1 | 1/1991 |
| WO | WO-92/20373 A1 | 11/1992 |
| WO | WO-93/08829 A1 | 5/1993 |
| WO | WO-93/11161 A1 | 6/1993 |
| WO | WO-93/16185 A2 | 8/1993 |
| WO | WO-93/16185 A3 | 8/1993 |
| WO | WO-94/04690 A1 | 3/1994 |
| WO | WO-94/11026 A2 | 5/1994 |
| WO | WO-94/11026 A3 | 5/1994 |
| WO | WO-00/29004 A1 | 5/2000 |
| WO | WO-02/051870 A2 | 7/2002 |
| WO | WO-02/051870 A3 | 7/2002 |
| WO | WO-03/035694 A2 | 5/2003 |
| WO | WO-03/035694 A3 | 5/2003 |
| WO | WO-2004/043373 A2 | 5/2004 |
| WO | WO-2004/043373 A3 | 5/2004 |
| WO | WO-2004/089504 A1 | 10/2004 |
| WO | WO-2005/016968 A2 | 2/2005 |
| WO | WO-2005/016968 A3 | 2/2005 |
| WO | WO-2005/035572 A2 | 4/2005 |
| WO | WO-2005/035572 A3 | 4/2005 |
| WO | WO-2006/126942 A1 | 11/2006 |
| WO | WO-2008/091740 A2 | 7/2008 |
| WO | WO-2008/091740 A3 | 7/2008 |
| WO | WO-2008/091740 A4 | 7/2008 |
| WO | WO-2011/017514 A1 | 2/2011 |
| WO | WO-2011/073389 A1 | 6/2011 |
| WO | WO2011150110 A1 | 12/2011 |
| WO | WO-2012/135415 A1 | 10/2012 |

OTHER PUBLICATIONS

Carter et al., "High level *Escherichia coli* expression and production of a bivalent humanized antibody fragment" Bio/Tech 10:163-167 (Feb. 1992).

Chothia et al. (1987). "Canonical structures for the hypervariable regions of immunoglobulins," *J. Mol. Biol.* 196:901-917.

Clackson et al., "Making antibody fragments using phage display libraries" Nature 352:624-628 (Aug. 15, 1991).

Clynes et al., "Fc receptors are required in passive and active immunity to melanoma" PNAS 95(2):652-656 (Jan. 1998).

Cunningham et al. "High-resolution epitope mapping of hGH-receptor interactions by alanine-scanning mutagenesis" Science 24:1081-1085 (Jun. 2, 1989).

Daeron, "Fc receptor biology" Annu Rev Immunol 15:203-234 (1997).

Davies et al. (1994). "'Camelising' human antibody fragments: NMR studies on VH domains," *FEBS Letters* 339:285-290.

De Hass et al. "Fcγ receptors of phagocytes" J Lab. Clin. Med. 126(4):330-341 ( 1995).

Dooley et al. (2006). "Antibody repertoire development in cartilaginous fish," *Dev. Comp. Immunol.* 30:43-56.

Fahrner et al. (2001). "Industrial purification of pharmaceutical antibodies: development, operation, and validation of chromatography processes," *Biotechnol. Genet. Eng. Rev.* 18:301-327.

Fahrner et al. (1999). "Performance comparison of protein A affinity-chromatography sorbents for purifying recombinant monoclonal antibodies," *Biotechnol. Appl. Biochem.* 30(Pt. 2):121-128.

Fahrner et al. (1999). "The optimal flow rate and column length for maximum production rate of protein a affinity chromatography," *Bioprocess Eng.* 21:287-292.

Federal Register (1997). "Impurities: Residual Solvents, Note for Guidance on Impurities: Residual Solvents (CPMP/ICH/283/95)," vol. 62, No. 247, 12 Total Pages.

Food and Drug Administration (Jul. 2005). "Guidance for Industry Estimating the Maximum Safe Starting Dose in Initial Clinical Trials for Therapeutics in Adult Healthy Volunteers," located at <http://www.fda.gov/downloads/Drugs/Guidances/UCM078932.pdf>, last visited on Mar. 11, 2015, 30 pages.

GE Healthcare (2002). "Affinity Chromatography: Principles and Methods," 159 Total Pages.

GE Healthcare et al. (2009). "Use of Sodium Hydroxide for Cleaning and Sanitizing Chromatography Media and Systems," GE Healthcare, Application Note 18-1124-57 AG, pp. 1-8.

Goding (1986). *Monoclonal Antibodies: Principles and Practice*, "Production and Application of Monoclonal Antibodies in Cell Biology, Biochemistry and Immunology"Academic Press, pp. 56-103.

Griffiths et al., "Human anti-self antibodies with high specificity from phage display libraries" EMBO Journal 12:725-734 (1993).

Gruber et al., "Efficient tumor cell lysis mediated by a bispecific single chain antibody expressed in *Escherichia coli*" J Immunol 152:5368-5374 (1994).

Guyer et al., "Immunoglobulin binding by mouse intestinal epithelial cell receptors" *J Immunol* 117(2):587-593 (Aug. 1976).

Hahn, R. et al. (Jan. 13, 2006). "Comparison of Protein a Affinity Sorbents III. Life Time Study," *Journal of Chromatography A* 1102(1-2):224-231.

Hollinger et al. (1993). "Diabodies: small bivalent and bispecific antibody fragments," *PNAS* 90:6444-6448.

Holt et al. (2003). "Domain antibodies: proteins for therapy," *Trends Biotechnol.* 21:484-490.

International Search Report dated Dec. 24, 2014, for PCT Patent Application No. PCT/US2014/054313, filed on Sep. 5, 2014, three pages.

Jakobovits et al., "Analysis of Homozygous Mutant Chimeric Mice: Deletion of the Immunoglobin Heavy-Chain Joining Region Blocks B-cell Development and Antibody Production" PNAS 90(6):2551-2555 (Mar. 15, 1993).

Jakobovits et al., "Germ-line Transmission and Expression of a Human-Derived Yeast Artificial Chromosome" Nature 362(6417):255-258 (Mar. 18, 1993).

Johnson & Chiswell, "Human antibody engineering" Curr Opin Struc Biol 3:564-571 (1993).

Jones et al., "Replacing the complementarity-dtermining regions in a human antibody with thise from a mouse" Nature 321:522-525 (1986).

Kelley et al. (2007). "Very large scale monoclonal antibody purification: the case for conventional unit operations," *Biotechnol. Prog.* 23:995-1008.

Kim et al., "Localization of the site of the murine IgG1 molecule that is involved in binding to the murine intestinal Fc receptor" Eur J Immunol. 24(10):2429-24234 (Oct. 1994).

Kohler et al. (1975). "Continuous cultures of fused cells secreting antibody of predefined specificity," *Nature* 256:495-497.

Kostelny et al., "Formation of a bispecific antibody by the use of leucine zippers" J Immunol 148(5):1547-1553 (Mar. 1, 1992).

Kozbor et al., "A Human Hybrid Myeloma for Production of Human Monoclonal Antibodies" J Immunol 133(6):3001-3005 (Dec. 1, 1984).

Lehninger, "The amino acid building blocks of protein" Biochemistry (Figures 4.2-4.4), 2nd Edition edition, New York, NY: Worth Publishers, Inc. pp. 73-75 (1975).

Mahajan, E. et al. (Mar. 8, 2013). "One Resin, Multiple Products: A green Approach to Purification" Chapter 6, pp. 86-111.

Marks et al., "By-passing immunization, Human antibodies from V-gene libraries displayed on phage" J. Mol. Biol. 222:581-597 (1991).

Marks et al., "By-passing immunization: building high affinity human antibodies by chain shuffling" Bio/Technology 10(7):779-783 (Jul. 1992).

McCafferty et al., "Phage Antibodies: Filamentous Phage Displaying Antibody Variable Domains" Nature 348:552-554 (Dec. 1990).

Merrifield, R.B., "Solid Phase Peptide Synthesis. I. The Synthesis of a Tetrapeptide" J. Am. Chem. Soc. 85(14):2149-2154 (Jul. 20, 1963).

Millstein et al., "Hybrid hybridomas and their use in immunohistochemistry" Nature 305:537-539 (1983).

Morimoto et al. "Single-step purification of F(ab') $_2$ fragments of mouse monoclonal antibodies (immunoglobulins G1) by hydropho-

(56) References Cited

OTHER PUBLICATIONS bic interaction high performance liquid chromatography using TSKgel phenyl-5PW" J. Biochem. Biophys. Meth. 24:107-117 (1992).

Morrison et al., "Chimeric human antibody molecules: Mouse antigen-binding domains with human constant region domains" PNAS 81:6851-6855 (Nov. 1984).

Munson et al. "Ligand: A Versatile Computerized Approach for Characterization of Ligand-Binding Systems" Anal Biochem 107(1):220-239 (Sep. 1, 1980).

Muyldermans et al. (2001). "Recognition of antigens by single-domain antibody fragments: the superfluous luxury of paired domains," *Trends Biochem. Sci.* 26:230-235.

Octagam® (Aug. 2002). "Product Approval Information Summary Basis of Approval Octagam® 5% Octapharma Pharmazeutika," located at <www.fda.gov/downloads/BiologicsBloodVaccines/BloodBloodProducts/ApprovedProducts/LicensedProductsBLAs/FractionatedPlasmaProducts/ucm064955.pdf>, last visited on Mar. 11, 2015, 11 pages.

Pluckthun (1994). "Antibodies from *Escherichia*," Chapter 11 in *The Pharmacology of Monoclonal Antibodies*, vol. 113, Rosenburg and Moore eds., Springer-Verlag, New York, pp. 269-315.

Presta et al., "Humanization of an antibody directed against IgE" J. Immunol. 151(5):2623-2632 (Sep. 1, 1993).

Presta, "Antibody Engineering" Curr. Opin. Struc. Biol. 2:593-596 (1992).

Ravetch and Kinet, "Fc receptors" Annu. Rev. Immunol. 9:457-492 (1991).

Reichmann et al., "Reshaping human antibodies for therapy" Nature 332:323-327 (Mar. 24, 1988).

Shopes, "A Genetically Engineered Human IgG Mutant With Enhanced Cytolytic Activity" J Immunol 148(9):2918-2922 (May 1992).

Sims et al. (1993). "A humanized CD18 antibody can block function without cell destruction," *J. Immunol.* 151:2296-2308.

Skerra, A., "Bacterial expression of immunoglobulin fragments" Curr. Opinion in Immunol. 5:256-262 (1993).

Stevenson et al., "A Chimeric Antibody With Dual Fc Regions (bisFabFc) Prepared by Manipulations at the IgG Hinge" Anti-Cancer Drug Des 3(4):219-230 (1989).

Suresh et al., "Bispecific Monoclonal Antibodies from Hybrid Hybridomas" Method Enzymol. 121:210-228 (1986).

Teschner et al. (2007). "A new liquid, intravenous immunoglobulin product (IGIV 10%) highly purified by a state-of-the-art process," *Vox Sang* 92:42-55.

Thai et al. (Mar. 2, 2009). "Purification Strategies to Process 5 g/L Titers of Monoclonal Antibodies," *BioPharm. Int'l*, 5 Total Pages.

Traunecker et al., "Bispecific single chain molecules (Janusins) target cytotoxic lymphocytes on HIV infected cells" EMBO J 10(12):3655-3659 (1991).

Tutt et al., "Trispecific F(ab') $_3$ derivatives that use cooperative signaling via the TCR/CD3 complex and CD2 to activate and redirect resting cytotoxic T cells" J Immunol 147(1):60-69 (Jul. 1991).

Verhoeyen et al., "Reshaping Human Antibodies: Grafting an Antilysozyme Activity" Science 239:1534-1536 (Mar. 1988).

Vitetta et al., "Redesigning Nature's Poisons to Create Anti-Tumor Reagents" Science 238:1098-1104 (1987).

Ward et al. (1989). "Binding activities of a repertoire of single immunoglobulin variable domains secreted from *Escherichia coli*," *Nature* 341:544-546.

Waterhouse et al., "Combinatorial infection and in vivo recombination: a strategy for making large phage antibody repertoires" Nucl Acids Res 21(9):2265-2266 (1993).

Wolff et al., "Monoclonal antibody homodimers: enhanced antitumor activity in nude mice" Cancer Res 53(11):2560-2565 (Jun. 1993).

Written Opinion of the International Searching Authority dated Dec. 24, 2014, for PCT Patent Application No. PCT/US2014/054313, filed on Sep. 5, 2014, five pages.

Zapata et al. (1995). "Engineering linear F(ab')2 fragments for efficient production in *Escherichia coli* and enhanced antiproliferative activity," *Prot. Eng.* 8:1057-1062.

Zhu-Shimoni et al. (2009). "Trace level analysis of leached Protein a in bioprocess samples without interference from the large excess of rhMAb IgG," *J. Immunol. Methods* 341:59-67.

Extended European Search Report and Search Opinion dated Aug. 2, 2017, for EP Patent Application No. 14841863.5, filed on Sep. 5, 2014, 20 pages.

\* cited by examiner

MAb A

MAb B

METHOD FOR CHROMATOGRAPHY REUSE

CROSS-REFERENCE TO RELATED APPLICATIONS

This application is a continuation of U.S. patent application Ser. No. 14/479,092, filed on Sep. 5, 2014, now abandoned, which claims the benefit of priority to U.S. Provisional Ser. No. 61/874,305, filed on Sep. 5, 2013, entitled METHOD FOR CHROMATOGRAPHY REUSE, which are hereby incorporated by reference in their entirety for all purposes.

FIELD OF THE INVENTION

The present invention provides methods for chromatography.

BACKGROUND OF THE INVENTION

Recombinant monoclonal antibodies (mAbs) are used in medicine and diagnostics (Albrecht, H., et al., *Drugs Today* 2009, 45:199-211; Takimoto, C. H.; Principles of Oncologic Pharmacotherapy Calvo, E. In Cancer Management: a Multidisciplinary Approach Medical, Surgical & Radiation Oncolog, 11th ed.; Pazdur, R.; Wagman, L. D.; Camphausen, K. A.; Hoskins, W. J., Eds. CMP Healthcare Media LLC: Lawrence, Kans., USA, 2008). Industrially, recombinant mAbs are bioproduced in living cells, such as Chinese Hamster Ovary (CHO) cells (Fahrner, R. L., et al., *Biotechnol. Genet. Eng. Rev.* 2001, 18:301-327). Once produced, the mAb of interest must be isolated from the cellular and media components used for its production. This purification process has two main steps (a) the primary isolation process, which is followed by (b) the final purification process. The primary mAb isolation process begins after the cells are harvested for the mAb of interest. Once the mAb is harvested the product pool contains the mAb of interest as well as cellular components (media components, proteins, DNA) and viruses that may be present during the mAb production process. In the first chromatography step of an exemplary isolation process, the product pool is run through a Protein A affinity column (Step 1). The purpose of the Protein A affinity step is to remove media components, cellular debris, and putative viruses. Following Step 1, the product pool, containing the mAb, is further purified over an ion exchange column (IEX, Step 2). Step 2 serves to remove additional contaminants, such as aggregates and DNA. After IEX chromatography the last step of the primary isolation process includes a step to remove viruses using a virus reduction filter (Step 3). Typically after Step 3 a final purification of the mAb is performed with a second ion exchange step (Step 4), to remove any residual CHO proteins (CHOP). After final purification, Ultrafiltration/Diafiltration (UF/DF, Step 5) is performed to remove small molecules, concentrate the mAb, and exchange the buffer to formulate the purified mAb into its final formulation buffer. This is followed by a bulk filtration step, which ensures sterility of the mAb pool (Step 6).

The use of Protein A affinity chromatography in industrial mAb purification is commonplace as it is efficient, scalable, and reproducible (Affinity Chromatography Principles and Methods, Amersham Biosciences, Uppsala, Sweden, 2002, see the world wide web at gelifesciences.com/webapp/wcs/stores/servlet/productById/en/GELifeSciences-us/181022-29 as accessed on Jul. 13, 2012; Fahrner, R. L. et al., *Bioprocess Eng.* 1999, 22:287). However, Protein A resin costs are significant, comprising a substantial portion of the raw material costs in MAb manufacturing (Fahrner, R. L., et al., *Biotechnol. Appl. Biochem.* 1999, 30, 121-128; Kelley, B., *Biotechnol. Prog.* 2007, 23:995-1008). This expense is further exacerbated by resin underuse, such that a single packed Protein A column is used only 10% of its potential lifetime (in the pilot plant and during clinical production). In order to reduce these costs reuse of Protein A resin for multiple different mAb products is desired. Protein A resin reuse for multiple products is not a common practice as reuse can result in protein carryover, not only from previous runs, but also from previously purified products. Thus an efficient cleaning process would enable reuse. Such a process would not only save money, space, and time, but would also be environmentally friendly. In addition, time savings are obtained from the avoidance of repacking columns for every new mAb synthesized. Reuse of Protein A resin is also cleaner for the environment, as there is less Protein A resin that is wasted, stored, or shipped. Note a typical MabSelect™ SuRe resin can be used up to 250 cycles (times) (Fahrner, R. L. *Biotechnol. Appl. Biochem.* 1999, 30, 121-128; Kelley, B., *Biotechnol. Prog.* 2007, 23:995-1008; MabSelect™ Sure resin; Application note 28-9872096 AA; Lifetime performance study of MabSelect™ Sure LX during repeated cleaning-in-place; GE Healthcare, Piscataway, N.J. February 2011. See the worldwide web at gelifesciences.com/gehcls_images/GELS/Related %20Content/Files/131-4807262343/litdoc2898 7296AA_20110831222625.pdf). However, on pilot plant scale for a typical clinical or toxicology run, a Protein A column is only used at total 3-4 runs (18-30 cycles), wasting anywhere from 220-232 cycles (Fahrner, R. L., et al., *Biotechnol. Genet. Eng. Rev.* 2001, 18:301-327). As described herein, the reuse of chromatography columns such as MabSelect™ SuRe resin columns for multiple CHO products on lab and pilot scale was enabled and optimized. To reduce levels of mAb carryover from previous purifications to acceptable levels an improved Protein A resin cleaning procedure to be used between mAb purification runs was developed and validated. This was achieved by addressing the following: (a) quantification of the amount of pre-cleaning protein carryover (if any) from previous purifications into subsequent purifications using the same Protein A resin, and (b) identification of a method to clean a Protein A affinity resin before or after use such that multiple products could be purified over the same Protein A resin with limited protein carryover and no safety concerns.

All references cited herein, including patent applications and publications, are incorporated by reference in their entirety.

BRIEF SUMMARY

The invention provides methods to clean or regenerate a chromatography material, e.g., a chromatography resin, for reuse. The chromatography material may be cleaned and/or regenerated for use with the same product or with different product.

In some aspects, the invention provides methods to clean a chromatography material for reuse comprising the steps of a) passing two or more material volumes of elution buffer through the material, wherein the elution buffer comprises about 0.15 M acetic acid and is about pH 2.9; b) statically holding the material in elution buffer for a time ranging from about 10 minutes to about 30 minutes; c) passing about two or more material volumes of elution buffer through the material; and d) passing about two or more material volumes of regeneration buffer through the material, wherein the regeneration buffer comprises about 0.1 N NaOH and is about pH 13.

In some aspects, the invention provides methods to clean a chromatography material for reuse comprising the steps of a) passing about two material volumes of elution buffer through the material, wherein the elution buffer comprises about 0.15 M acetic acid and is about pH 2.9; b) statically holding the material in elution buffer for about 30 minutes; c) passing about two material volumes of elution buffer through the material; and d) passing about four material volumes of regeneration buffer through the material, wherein the regeneration buffer comprises about 0.1 N NaOH and is about pH 13.

In some aspects, the invention provides methods to clean a chromatography material for reuse comprising the steps of a) passing about two material volumes of elution buffer through the material, wherein the elution buffer comprises about 0.15 M acetic acid and is about pH 2.9, b) statically holding the material in elution buffer for about 30 minutes, c) passing about two material volumes of elution buffer through the material, and d) passing about two and one-half material volumes of regeneration buffer through the material, wherein the regeneration buffer comprises about 0.1 N NaOH and is about pH 13, e) statically holding the material in regeneration buffer for about 30 minutes, f) passing about two and one-half material volumes of regeneration buffer through the material.

In some aspects, the invention provides methods to clean a chromatography material for reuse comprising the steps of a) passing about two material volumes of equilibration buffer through the material, wherein the equilibration buffer comprises about 25 mM Tris and about 25 mM NaCl and is about pH 7.1; b) statically holding the material in equilibration buffer for about 30 minutes; c) passing about two material volumes of equilibration buffer through the material; d) passing about two material volumes of elution buffer through the material, wherein the elution buffer comprises about 0.15 M Acetic acid and is about pH 2.8; e) statically holding the material in elution buffer for about 30 minutes; f) passing about two material volumes of elution buffer through the material; g) passing about two material volumes of regeneration buffer through the material, wherein the regeneration buffer comprises 0.1 N NaOH, pH 13; h) statically holding the material in regeneration buffer for about 30 minutes; i) passing about two material volumes of regeneration buffer through the material.

In some aspects, the invention provides methods to clean a chromatography material for reuse comprising the steps of a) passing about four material volumes of equilibration buffer through the material, wherein the equilibration buffer comprises about 25 mM Tris and about 25 mM NaCl and is pH 7.1; b) performing six cycles of the steps comprising i) passing about three material volumes of elution buffer through the material, wherein the elution buffer comprises about 0.15 M Acetic acid and is about pH 2.8; ii) statically holding the material in elution buffer for about 10 minutes; iii) passing about one material volume of elution buffer through the material; iv) passing about three material volumes of regeneration buffer through the material, wherein the regeneration buffer comprises about 0.1 N NaOH and is about pH 13; v) statically holding the material in regeneration buffer for about 10 minutes; vi) passing about one material volume of regeneration buffer through the material.

In some aspects, the invention provides methods to clean a chromatography material for reuse comprising the steps of a) passing about three material volumes of elution buffer through the material, wherein the elution buffer comprises about 0.15 M Acetic acid and is about pH 2.8; b) statically holding the material in elution buffer for about 15 minutes; c) passing about one material volume of elution buffer through the material; d) passing about three material volumes of regeneration buffer through the material, wherein the regeneration buffer comprises about 0.1 N NaOH and is about pH 13; e) statically holding the material in regeneration buffer for about 15 minutes; f) passing about one material volume of regeneration buffer through the material; g) passing about three material volumes of storage buffer through the material, wherein the storage buffer comprises about 100 mM sodium acetate, about 2% benzyl alcohol, and is about pH 5.0; e) statically holding the material in storage buffer for about 15 minutes; f) passing about one material volume of storage buffer through the material.

In some embodiments of the above aspects, the chromatography material is in a chromatography column. In some embodiments, the chromatography material is an affinity material. In further embodiments, the affinity material is a protein A affinity material; for example but not limited to a MAbSelect material, a MAbSelect SuRe material or a MAbSelect SuRe LX material. In some embodiments of the above aspects, the chromatography material is used for large-scale production of a polypeptide.

In some aspects, the invention provides methods to clean a chromatography material for reuse, the method comprising the steps of a) passing about three material volumes of equilibration buffer through the material, wherein the equilibration buffer comprises about 40 mM sodium acetate and is about pH 5.5; b) passing about two material volumes of about 0.5 N NaOH through the material c) statically holding the material in about 0.5 N NaOH for about 10 minutes; d) passing about one material volume of about 0.5 N NaOH through the material; and e) statically holding the material in about 0.5 N NaOH for about 10 minutes; f) passing about one material volume of about 0.5 N NaOH through the material.

In some embodiments of the above aspect, the chromatography material is in a chromatography column. In some embodiments, the chromatography material is an ion exchange material. In some embodiments, the ion exchange material is a cation exchange material; for example a POROS HS50 material. In some embodiments, the chromatography material is used for large-scale production of an antibody.

In some aspects, the invention provides methods to clean a chromatography material for reuse, the method comprising the steps of a) passing about three material volumes of equilibration buffer through the material, wherein the equilibration buffer comprises about 50 mM Tris, 85 mM sodium acetate and is about pH 8.8 and about 8.6 mS/cm; b) passing about two material volumes of about 0.5 N NaOH through the material; c) statically holding the material in about 0.5 N NaOH for about 10 minutes; d) passing about one material volume of about 0.5 N NaOH through the material; and e) statically holding the material in about 0.5 N NaOH for about 10 minutes; f) passing about one material volume of about 0.5 N NaOH through the material.

In some embodiments of the above aspect, the chromatography material is in a chromatography column. In some embodiments, the chromatography material is an ion exchange material. In some embodiments, the ion exchange material is an anion exchange material; for example, a QSFF material. In some embodiments, the chromatography material is used for large-scale production of an antibody.

In some embodiments of any of the above aspects, the buffers are passed through the material at about 30 material volumes/hour, about 20 material volumes/hour or about 15 material volumes/hour. In some embodiments, the buffer is passed through the material in a downflow direction or an upflow direction. In some embodiments, the cleaning of the chromatography material is measured by running a mock elution after cleaning the chromatography material. In some embodiments, an eluent of the mock elution comprising one or more of <0.25 mg/mL total protein, <1 ppm IgG fragments, <1 ppm leached protein A, <1 μg/mL CZE LIF, <1 ppm CHOP, and <1 pg/mL CHO DNA indicates effective cleaning of the material for multiproduct use. In some embodiments, the chromatography material is stable in alkali.

In some embodiments of any of the above aspects, the chromatography material is used to purify a polypeptide. In some embodiments, the chromatography material is cleaned following purification of a first polypeptide and wherein the chromatography material is used to purify a second polypeptide following the cleaning. In some embodiments, the polypeptide is an antibody or immunoadhesin. In some embodiments, the antibody is a monoclonal antibody. In further embodiments, the monoclonal antibody is a chimeric antibody, humanized antibody, or human antibody. In further embodiments, the monoclonal antibody is an IgG monoclonal antibody. In some embodiments, the antibody is an antigen binding fragment. In some embodiments, the antigen binding fragment is a Fab fragment, a Fab' fragment, a F(ab')2 fragment, a scFv, a di-scFv, a bi-scFv, a tandem (di, tri)-scFv, a Fv, a sdAb, a tri-functional antibody, a BiTE, a diabody or a triabody. In other embodiments, polypeptide is an enzyme, a hormone, a fusion protein, an Fc-containing protein, an immunoconjugate, a cytokine or an interleukin. In some embodiments, the first polypeptide is a first antibody or a first immunoadhesin and the second polypeptide is a second antibody or second immunoadhesin.

BRIEF DESCRIPTION OF THE DRAWINGS

FIG. 6A. Protein carryover (ng/mg protein) as a function of Elution buffer cycle wash; FIG. 6B. protein carryover (ng/mg protein) as a function of Regeneration buffer cycle wash; FIG. 6C. protein carryover (ng/mg protein) as a function of the stage in the "mock run". Intact IgG is shown in black, Fc fragments are shown in grey.

FIG. 10A. Protein carryover (ng/mg protein) as a function of Elution buffer cycle wash; FIG. 10B. protein carryover (ng/mg protein) as a function of Regeneration buffer cycle wash; FIG. 10C. protein carryover (ng/mg protein) as a function of the stage in the "mock run".

FIG. 12A. Protein carryover (ng/mg protein) as a function of Elution buffer cycle wash; FIG. 12B. protein carryover (ng/mg protein) as a function of Regeneration buffer cycle wash. Intact IgG is shown in black, Fc fragments are shown in grey.

DETAILED DESCRIPTION OF THE INVENTION

Figure 1:
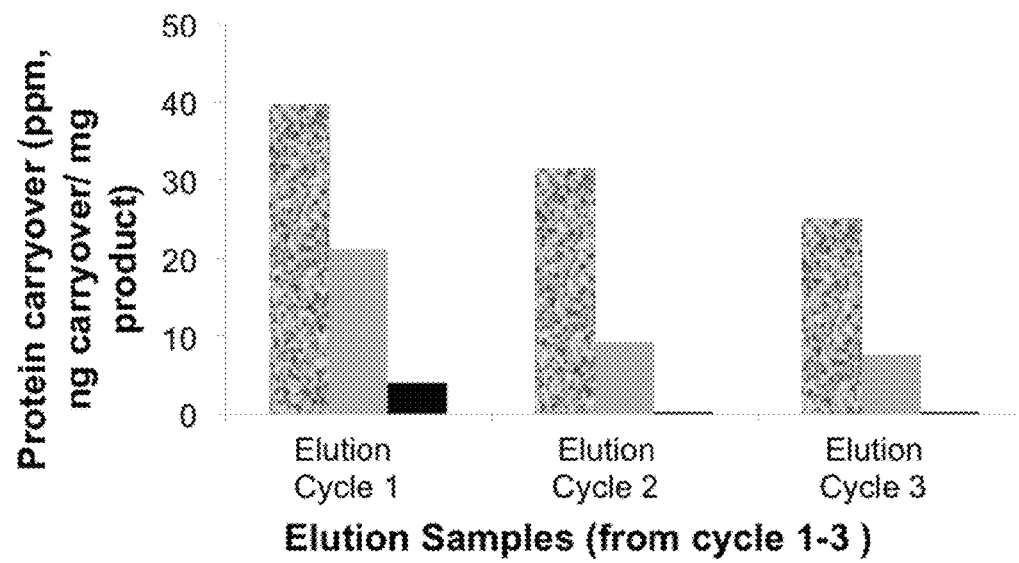
FIG. 1 shows a plot of total protein carryover (intact IgG+Fc fragment) as a function of Elution sample cycle from a sequential lab scale purification of mAbA, mAbB, and mAbC on a MabSelect™ SuRe column without additional resin cleaning. Legend: mAbA carryover in mAbB elution (black & grey), mAbB carryover in mAbC elution (grey), and mAbA carryover in mAbC elution (black).

Provided herein are methods to clean or regenerate a chromatography material, e.g., a chromatography resin, for reuse. Chromatography reuse is a changeover procedure where the chromatography material is cleaned and/or regenerated for use with the same product or a different product. The methods of the invention can be used for the regeneration of large-scale; e.g. manufacturing-scale, chromatography material. Significant cost savings can be achieved if a resin; e.g., a Protein A resin, is reused for multiple products. In some embodiments, the cleaning procedure results in less than 1 ppm carryover of intact protein; e.g., an IgG, into subsequent purification samples. In some embodiments, this low protein carryover is $10^3$ fold less protein carryover than that set in safety margins, and demonstrates that the same resins can be used to purify multiple products. In some embodiments, the chromatography material is in a chromatography column.

I. Definitions

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

"Purified" polypeptide (e.g., antibody or immunoadhesin) means that the polypeptide has been increased in purity, such that it exists in a form that is more pure than it exists in its natural environment and/or when initially synthesized and/or amplified under laboratory conditions. Purity is a relative term and does not necessarily mean absolute purity.

A polypeptide "which binds" an antigen of interest, e.g. a tumor-associated polypeptide antigen target, is one that binds the antigen with sufficient affinity such that the polypeptide is useful as a diagnostic and/or therapeutic agent in targeting a cell or tissue expressing the antigen, and does not significantly cross-react with other polypeptides. In such embodiments, the extent of binding of the polypeptide to a "non-target" polypeptide will be less than about 10% of the binding of the polypeptide to its particular target polypeptide as determined by fluorescence activated cell sorting (FACS) analysis or radioimmunoprecipitation (RIA).

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions ("HVRs"), which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three hypervariable regions, for example, complementarity determining regions ("CDRs"), each of which contains a "hypervariable loop", and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies have antigen binding sites which are defined by $V_H$ and $V_L$ domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between $V_H$ and $V_L$.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

"Framework" or "FR" residues are those variable domain residues other than the hypervariable region residues as herein defined.

"Antibody fragments" comprise a portion of an intact antibody, preferably comprising the antigen binding region thereof. Examples of antibody fragments include Fab, Fab', $F(ab')_2$, and Fv fragments; diabodies; tandem diabodies (taDb), linear antibodies (e.g., U.S. Pat. No. 5,641,870, Example 2; Zapata et al., *Protein Eng.* 8(10):1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di, tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_HV_L$ unit has polyepitopic specificity, antibodies having two or more $V_L$ and $V_H$ domains with each $V_HV_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 μM to 0.001 pM, 3 μM to 0.001 pM, 1 μM to 0.001 pM, 0.5 μM to 0.001 pM, or 0.1 μM to 0.001 pM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a cytotoxic moiety or radiolabel.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci.* (USA) 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

The terms "Fc receptor" or "FcR" are used to describe a receptor that binds to the Fc region of an antibody. In some embodiments, the FcR is a native sequence human FcR. Moreover, a preferred FcR is one that binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daeron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "sequential" as used herein with regard to chromatography refers to having a first chromatography followed by a second chromatography. Additional steps may be included between the first chromatography and the second chromatography.

The term "continuous" as used herein with regard to chromatography refers to having a first chromatography material and a second chromatography material either directly connected or some other mechanism which allows for continuous flow between the two chromatography materials.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated".

An "Acceptable Daily Exposure (ADE)" as used herein is a substance-specific dose that is unlikely to cause an adverse health event or undesirable physiological effect if an individual is exposed to this does or to a lower dose over a lifetime (Teschner, W., et al., *Vox Sang.* 2007, 92:42-55; Food and Drug Administration, HHS. Guidance for Industry Estimating the Maximum Safe Starting Dose in Initial Clinical Trials for Therapeutics in Adult Healthy Volunteers. Rockville, Md. July 2005 on the world wide web at google. com/url?sa=t&rct=j&q=&esrc=s&source=web&cd=1& v-ed=0CE8QFjAA&url=http%3A%2F%2Fwww.fda.gov %2-Fdownloads%2FDrugs%2F...%2FGuidances%2FUCM07-8932.pdf&ei=f4QhUJv4K9Ov6gGQ-4DgAg&usg=AFQj-CNFbTE- 75U0nDbFpfdpxK85uWXT8frg as accessed on Aug. 7, 2012; European Medicines Agency. Impurities: Residual Solvents, Note for Guidance on Impurities: Residual Solvents (CPMP/ICH/283/95). London, UK September 1997 on the world wide web at ema.europa.eu/ema/index.jsp?curl=pages/regulation/general/general_content_000431. jsp&mid=WC0b01ac0580029593 as accessed on Aug. 7, 2012). In addition to an ADE, an "Estimated Daily Intake (EDI)" for IgG is determined based on the amount of IgG administered per dose.

"Contaminants" refer to materials that are different from the desired polypeptide product. The contaminant includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc. In some examples, the contaminant may be a host cell protein (HCP) from, for example but not limited to, a bacterial cell such as an *E. coli* cell, an insect cell, a prokaryotic cell, a eukaryotic cell, a yeast cell, a mammalian cell, an avian cell, a fungal cell.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

II. Methods of Column Cleaning (A) Chromatography

The invention provides methods to clean or regenerate chromatography materials for reuse. In some embodiments, the chromatography materials are used for large-scale; e.g., manufacturing-scale, production of polypeptide products.

In some embodiments, the method comprises the steps of a) passing about two or more material volumes of elution buffer through the material, wherein the elution buffer comprises about 0.15 M acetic acid, at about pH 2.9; b) statically holding the material in elution buffer for a time ranging from about 10 min to about 30 min; c) passing about two or more material volumes of elution buffer through the material; and d) passing about two or more material volumes of regeneration buffer through the material, wherein the regeneration buffer is about 0.1 N NaOH, pH 13. In some embodiments, the chromatography material is in a chromatography column. In some embodiments, the chromatography column is used for large-scale, e.g. manufacturing-scale, production of a polypeptide product such as an antibody product. In some embodiments, the chromatography material is a Protein A chromatography material. In some embodiments, the chromatography material is used to purify multiple antibody products. In some embodiments, the carryover after the cleaning methods comprises one or more of <0.25 mg/mL total protein, <1 ppm IgG fragments, <1 ppm leached protein A, <1 µg/mL CZE LIF, <1 ppm CHOP, and <1 pg/mL CHO DNA.

In some embodiments, the method comprising the steps of a) passing about two material volumes of elution buffer through the material, wherein the elution buffer comprises about 0.15 M acetic acid, at about pH 2.9; b) statically holding the material in elution buffer for about 30 min; c) passing about two material volumes of elution buffer through the material; and d) passing about four material volumes of regeneration buffer through the material, wherein the regeneration buffer is about 0.1 N NaOH, at about pH 13. In some embodiments, the chromatography material is in a chromatography column. In some embodiments, the chromatography column is used for large-scale, e g manufacturing-scale, production of a polypeptide product such as an antibody product. In some embodiments, the chromatography material is a Protein A chromatography material. In some embodiments, the chromatography material is used to purify multiple antibody products. In some embodiments, the carryover after the cleaning methods comprises one or more of <0.25 mg/mL total protein, <1 ppm IgG fragments, <1 ppm leached protein A, <1 µg/mL CZE LIF, <1 ppm CHOP, and <1 pg/mL CHO DNA.

In some embodiments, the method comprising the steps of a) passing about two material volumes of elution buffer through the material, wherein the elution buffer comprises about 0.15 M acetic acid, at about pH 2.9, b) statically holding the material in elution buffer for about 30 min, c) passing about two material volumes of elution buffer through the material, d) passing about two and one-half material volumes of regeneration buffer through the material, wherein the regeneration buffer is about 0.1 N NaOH, at about pH 13, e) statically holding the material in regeneration buffer for about 30 min, f) passing about two and one-half material volumes of regeneration buffer through the material. In some embodiments, the chromatography material is in a chromatography column. In some embodiments, the chromatography column is used for large-scale, e g manufacturing-scale, production of a polypeptide product such as an antibody product. In some embodiments, the chromatography material is a Protein A chromatography material. In some embodiments, the chromatography material is used to purify multiple antibody products. In some embodiments, the carryover after the cleaning methods comprises one or more of <0.25 mg/mL total protein, <1 ppm IgG fragments, <1 ppm leached protein A, <1 µg/mL CZE LIF, <1 ppm CHOP, and <1 pg/mL CHO DNA.

In some embodiments, the method comprising the steps of a) passing about two material volumes of equilibration buffer through the material, wherein the equilibration buffer comprises about 25 mM Tris, about 25 mM NaCl, at about pH 7.1; b) statically holding the material in equilibration buffer for about 30 min; c) passing about two material volumes of equilibration buffer through the material; d) passing about two material volumes of elution buffer through the material, wherein the elution buffer is about 0.15 M Acetic acid, at about pH 2.8; e) statically holding the material in elution buffer for about 30 min; f) passing about two material volumes of elution buffer through the material; g) passing about two material volumes of regeneration buffer through the material, wherein the regeneration buffer is about 0.1 N NaOH, at about pH 13; h) statically holding the material in regeneration buffer for about 30 min; i) passing about two material volumes of regeneration buffer through the material. In some embodiments, the chromatography material is in a chromatography column. In some embodiments, the chromatography column is used for large-scale, e g manufacturing-scale, production of a polypeptide product such as an antibody product. In some embodiments, the chromatography material is a Protein A chromatography material. In some embodiments, the chromatography material is used to purify multiple antibody products. In some embodiments, the carryover after the cleaning methods comprises one or more of <0.25 mg/mL total protein, <1 ppm IgG fragments, <1 ppm leached protein A, <1 µg/mL CZE LIF, <1 ppm CHOP, and <1 pg/mL CHO DNA.

In some embodiments, the method comprising the steps of a) passing about four material volumes of equilibration buffer through the material, wherein the equilibration buffer comprises about 25 mM Tris, about 25 mM NaCl, at about pH 7.1; b) performing six cycles of the steps comprising i) passing about three material volumes of elution buffer through the material, wherein the elution buffer is about 0.15 M Acetic acid, pH 2.8; ii) statically holding the material in elution buffer for about 10 min; iii) passing about one material volume of elution buffer through the material; iv) passing about three material volumes of regeneration buffer through the material, wherein the regeneration buffer is about 0.1 N NaOH, at about pH 13; v) statically holding the material in regeneration buffer for about 10 min; vi) passing about one material volume of regeneration buffer through the material In some embodiments, the chromatography material is in a chromatography column. In some embodiments, the chromatography column is used for large-scale, e g manufacturing-scale, production of a polypeptide product such as an antibody product. In some embodiments, the chromatography material is a Protein A chromatography material. In some embodiments, the chromatography material is used to purify multiple antibody products. In some embodiments, the carryover after the cleaning methods comprises one or more of <0.25 mg/mL total protein, <1 ppm IgG fragments, <1 ppm leached protein A, <1 µg/mL CZE LIF, <1 ppm CHOP, and <1 pg/mL CHO DNA.

In some embodiments, the method comprising six cycles of the steps of a) passing about three material volumes of elution buffer through the material, wherein the elution buffer is about 0.15 M Acetic acid, at about pH 2.8; b) statically holding the material in elution buffer for about 15 min; c) passing about one material volume of elution buffer through the material; d) passing about three material volumes of regeneration buffer through the material, wherein the regeneration buffer is about 0.1 N NaOH, at about pH 13; e) statically holding the material in regeneration buffer for about 15 min; f) passing about one material volume of regeneration buffer through the material; g) passing about three material volumes of storage buffer through the material, wherein the storage buffer is about 100 mM sodium acetate, about 2% benzyl alcohol, at about pH 5.0; e) statically holding the material in storage buffer for about 15 min; f) passing about one material volume of storage buffer through the material. In some embodiments, the chromatography material is in a chromatography column. In some embodiments, the chromatography column is used for large-scale, e g manufacturing-scale, production of a polypeptide product such as an antibody product. In some embodiments, the chromatography material is a Protein A chromatography material. In some embodiments, the chromatography material is used to purify multiple antibody products. In some embodiments, the carryover after the cleaning methods comprises one or more of <0.25 mg/mL total protein, <1 ppm IgG fragments, <1 ppm leached protein A, <1 µg/mL CZE LIF, <1 ppm CHOP, and <1 pg/mL CHO DNA.

In some aspects of the invention, the chromatography material is an affinity chromatography material. Examples of affinity chromatography materials include, but are not limited to chromatography materials derivatized with protein A or protein G. Examples of affinity chromatography material include, but are not limited to, Prosep-VA, Prosep-VA Ultra Plus, Protein A sepharose fast flow, Tyopearl Protein A, MAbSelect™, MAbSelect™ SuRe and MAbSelect™ SuRe LX. In some embodiments of the above, the affinity chromatography material is an affinity chromatography material. In some embodiments of the above, the affinity chromatography material is an affinity chromatography membrane. In some embodiments, the affinity chromatography material is a Protein G chromatography material. In some embodiments, the chromatography column is used for large-scale, e g manufacturing-scale, production of a polypeptide product such as an antibody product.

In some aspects, the invention provides methods to clean an ion-exchange chromatography material for reuse. In some embodiments, the method comprising the steps of a) passing about three material volumes of equilibration buffer through the material, wherein the equilibration buffer comprises about 25 mM Tris, about 25 mM NaCl, at about pH 7.1; b) passing about two material volumes of about 0.5 N NaOH through the material c) statically holding the material in about 0.5 N NaOH for about 10 min; d) passing about one material volume of about 0.5 N NaOH through the material; e) statically holding the material in about 0.5 N NaOH for about 10 min; and f) passing about one material volume of about 0.5 N NaOH through the material. In some embodiments, the ion exchange material is in a chromatography column. In some embodiments, the chromatography column is used for large-scale, e.g. manufacturing-scale, production of a polypeptide product such as an antibody product. In some embodiments, the chromatography material is used to purify multiple antibody products. In some embodiments, the carryover after the cleaning methods comprises one or more of <0.25 mg/mL total protein, <1 ppm IgG fragments, <1 ppm leached protein A, <1 µg/mL CZE LIF, <1 ppm CHOP, and <1 pg/mL CHO DNA.

In some embodiments of any of the methods described herein, the chromatography material is an ion exchange chromatography material; for example, an anion exchange chromatography material or a cation exchange chromatography material. In some embodiments of any of the methods described herein, the chromatography material is an anion exchange material. In some embodiments, the anion exchange material is in a chromatography column. In some embodiments, the anion exchange chromatography material is a solid phase that is positively charged and has free anions for exchange with anions in an aqueous solution passed over or through the solid phase. In some embodiments of any of the methods described herein, the anion exchange material may be a membrane, a monolith, or resin. In an embodiment, the anion exchange material may be a resin. In some embodiments, the anion exchange material may comprise a primary amine, a secondary amine, a tertiary amine or a quarternary ammonium ion functional group, a polyamine functional group, or a diethylaminoaethyl functional group. In some embodiments of the above, the anion exchange chromatography material is an anion exchange chromatography material. In some embodiments of the above, the anion exchange chromatography material is an anion exchange chromatography membrane. In some embodiments, the anion exchange chromatography material is used for large-scale, e.g. manufacturing-scale, production of a polypeptide product such as an antibody product.

In some embodiments of any of the methods described herein, the chromatography material is a cation exchange material. In some embodiments, the cation exchange material is in a chromatography column. In some embodiments, the cation exchange material is a solid phase that is negatively charged and has free cations for exchange with cations in an aqueous solution passed over or through the solid phase. In some embodiments of any of the methods described herein, the cation exchange material may be a membrane, a monolith, or resin. In some embodiments, the cation exchange material may be a resin. The cation exchange material may comprise a carboxylic acid functional group or a sulfonic acid functional group such as, but not limited to, sulfonate, carboxylic, carboxymethyl sulfonic acid, sulfoisobutyl, sulfoethyl, carboxyl, sulphopropyl, sulphonyl, sulphoxyethyl, or orthophosphate. In some embodiments of the above, the cation exchange chromatography material is a cation exchange chromatography material. In some embodiments of the above, the cation exchange chromatography material is a cation exchange chromatography membrane. In some embodiments of the invention, the chromatography material is not a cation exchange chromatography material. In some embodiments, the cation exchange chromatography material is used for large-scale, e.g. manufacturing-scale, production of a polypeptide product such as an antibody product.

In some embodiments of any of the methods described herein, the ion exchange material may utilize a conventional chromatography material or a convective chromatography material. The conventional chromatography materials include, for example, perfusive materials (e.g., poly (styrene-divinylbenzene) resin) and diffusive materials (e.g., cross-linked agarose resin). In some embodiments, the poly (styrene-divinylbenzene) resin can be Poros resin. In some embodiments, the cross-linked agarose resin may be sulphopropyl-Sepharose Fast Flow ("SPSFF") resin. The convective chromatography material may be a membrane (e.g., polyethersulfone) or monolith material (e.g. cross-linked polymer). The polyethersulfone membrane may be Mustang. The cross-linked polymer monolith material may be cross-linked poly(glycidyl methacrylate-co-ethylene dimethacrylate).

Examples of anion exchange materials are known in the art and include, but are not limited to Poros HQ 50, Poros PI 50, Poros D, Mustang Q, Q Sepharose FF, and DEAE Sepharose.

Examples of cation exchange materials are known in the art include, but are not limited to Mustang S, Sartobind S, SO3 Monolith, S Ceramic HyperD, Poros XS, Poros HS50, Poros HS20, SPSFF, SP-Sepharose XL (SPXL), CM Sepharose Fast Flow, Capto S, Fractogel Se HiCap, Fractogel SO3, or Fractogel COO. In some embodiments of any of the methods described herein, the cation exchange material is Poros HS50. In some embodiments, the Poros HS resin may be Poros HS 50 µm or Poros HS 20 µm particles.

In some embodiments of any of the methods described herein, the chromatography material is a mixed mode material comprising functional groups capable of one of more of the following functionalities: anionic exchange, cation exchange, hydrogen bonding, and hydrophobic interactions. In some embodiments, the mixed mode material comprises functional groups capable of anionic exchange and hydrophobic interactions. The mixed mode material may contain N-benzyl-N-methyl ethanol amine, 4-mercapto-ethyl-pyridine, hexylamine, or phenylpropylamine as ligand or contain cross-linked polyallylamine Examples of the mixed mode materials include Capto Adhere resin, QMA resin, Capto MMC resin, MEP HyperCel resin, HEA HyperCel resin, PPA HyperCel resin, or ChromaSorb membrane or Sartobind STIC. In some embodiments, the mixed mode material is Capto Adhere resin. In some embodiments of the above, the mixed mode material is a mixed mode chromatography material. In some embodiments of the above, the mixed mode material is a mixed mode chromatography column. In some embodiments of the above, the mixed mode material is a mixed mode membrane. In some embodiments, the mixed mode chromatography column is a large-scale; e.g. manufacturing-scale, chromatography column.

In some aspects of the invention, the chromatography material is a hydrophobic interaction chromatography material. Hydrophobic interaction chromatography (HIC) is a liquid chromatography technique that separates biomolecules according to hydrophobicity. Examples of HIC chromatography materials include, but are not limited to, Toyopearl hexyl 650, Toyopear butyl 650, Toyopearl phenyl 650, Toyopearl ether 650, Source, Resource, Sepharose Hi-Trap, Octyl sepharose, and Phenyl sepharose. In some embodiments of the above, the HIC chromatography material is a HIC chromatography column. In some embodiments of the above, the HIC chromatography material is a HIC chromatography membrane. In some embodiments, the HUC chromatography column is a large-scale; e g manufacturing-scale, chromatography column.

In some aspects of the invention, the chromatography material is a hydroxyapatite (HAP) chromatography material. Examples of hydroxyapatite chromatography material include but are limited to HA Ultrogel, and CHT hydroxyapatite. In some embodiments of the above, the HAP chromatography material is a HAP chromatography column. In some embodiments of the above, the HAP chromatography material is a HAP chromatography membrane. In some embodiments, the HAP chromatography column is a large-scale; e g manufacturing-scale, chromatography column.

In some embodiments, the invention provides methods to clean or regenerate an alkali stable chromatography material; e.g. an alkali stable chromatography column.

The invention provides buffers for use in the methods of the invention. Elution buffers are generally used to remove a material from a chromatography material; e.g. a desired material or an undesired material such as a contaminant Examples of elution buffers include but are not limited to about 0.15 M acetic acid at about pH 2.8-2.9. A regeneration buffer is generally used to recharge a column following a chromatography procedure. For example, a regeneration buffer for an anion chromatography may be about 0.1 N NaOH at about pH 13. An equilibration buffer may be used to make put the chromatography material under the same conditions (salt concentration, pH, etc.) as the sample. A nonlimiting example of an equilibration buffer is about 25 mM Tris, and about 25 mM NaCl at about pH 7.1. A storage buffer is generally used to maintain a chromatography material when not in use; for example, with a microcode to prevent contamination. A nonlimiting example of a storage buffer is about 100 mM sodium acetate, about 2% benzyl alcohol, and at about pH 5.0.

In some embodiments of any of the methods described herein, the flow rate is less than about any of 50 material volumes/hr, 40 material volumes/hr, or 30 material volumes/hr. The flow rate may be between about any of 5 material volumes/hr and 50 material volumes/hr, 10 material volumes/hr and 40 material volumes/hr, or 18 material volumes/hr and 36 material volumes/hr. In some embodiments, the flow rate is about any of 9 material volumes/hr, 18 material volumes/hr, 25 material volumes/hr, 30 material volumes/hr, 36 material volumes/hr, or 40 material volumes/hr.

In some embodiments, the chromatography material is in a chromatography column. In some embodiments of any of the methods described herein, the flow rate is less than about any of 50 column volumes (CV)/hr, 40 CV/hr, or 30 CV/hr. The flow rate may be between about any of 5 CV/hr and 50 CV/hr, 10 CV/hr and 40 CV/hr, or 18 CV/hr and 36 CV/hr. In some embodiments, the flow rate is about any of 9 CV/hr, 18 CV/hr, 25 CV/hr, 30 CV/hr, 36 CV/hr, or 40 CV/hr. In some embodiments of any of the methods described herein, the flow rate is less than about any of 100 cm/hr, 75 cm/hr, or 50 cm/hr. The flow rate may be between about any of 25 cm/hr and 150 cm/hr, 25 cm/hr and 100 cm/hr, 50 cm/hr and 100 cm/hr, or 65 cm/hr and 85 cm/hr.

Bed height is the height of chromatography material used. In some embodiments of any of the method described herein, the bed height is greater than about any of 3 cm, 10 cm, or 15 cm. The bed height may be between about any of 3 cm and 35 cm, 5 cm and 15 cm, 3 cm and 10 cm, or 5 cm and 8 cm. In some embodiments, the bed height is about any of 3 cm, 5 cm, 10 cm, 15 cm, 20 cm, 25 cm, or 30 cm. In some embodiments, bed height is determined based on the amount of polypeptide or contaminants in the load. In some embodiments, the chromatography material is in a column used for large-scale; e.g., manufacturing-scale, production of a polypeptide. In some embodiments, the manufacturing-scale chromatography material has a bed height of about any of 10 cm, 15, cm, 20 cm, 25 cm or 30 cm.

Bed diameter is the diameter of chromatography material used. In some embodiments of any of the method described herein, the bed diameter is greater than about any of 80 cm, 100 cm, or 120 cm. In some embodiments, the bed diameter is about any of 50 cm, 60 cm, 70 cm, 80 cm, 90 cm, 100 cm, 110 cm, 120 cm, 130 cm, 140 cm, 150 cm, 160 cm, 170 cm, 180 cm, 190, or 200 cm. In some embodiments, bed diameter is determined based on the amount of polypeptide or contaminants in the load. In some embodiments, the chromatography material is in a column used for large-scale; e.g., manufacturing-scale, production of a polypeptide. In some embodiments, the manufacturing-scale chromatography material had a bed diameter of about any 50 cm, 60 cm, 70 cm, 80 cm, 90 cm, 100 cm, 110 cm, 120 cm, 130 cm, 140 cm, 150 cm, 160 cm, 170 cm, 180 cm, 190, or 200 cm.

In some embodiments, the chromatography is in a material of vessel with a volume of greater than about 1 mL, 2 mL, 3 mL, 4 mL, 5 mL, 6 mL, 7 mL, 8 mL, 9 mL, 10 mL, 15 mL, 20 mL, 25 mL, 30 mL, 40 mL, 50 mL, 75 mL, 100 mL, 200 mL, 300 mL, 400 mL, 500 mL, 600 mL, 700 mL, 800 mL, 900 mL, 1 L, 2 L, 3 L, 4 L, 5 L, 6 L, 7 L, 8 L, 9 L, 10 L, 25 L, 50 L, 100 L, 200 L, 300 L, 400 L, 500 L, 600 L, 700 L, 800 L, 900 L or 1000 L. In some embodiments, the vessel has a bed height of 14 cm and a bed volume of 80 cm; e.g. a large-scale protein A column. In some embodiments, the vessel has a bed height of 19 cm and a bed volume of 100 cm, e.g. a large-scale anion exchange column. In some embodiments, the vessel has a bed height of 30 cm and a bed volume of 120 cm, e.g. a large-scale cation exchange column.

Load, as used herein, is the composition loaded onto a chromatography material. In some embodiments, the load is a polypeptide that is loaded onto a chromatography material that had been previously used to isolate a different polypeptide. Loading buffer is the buffer used to load the composition comprising the product of interest onto a chromatography material. The chromatography material may be equilibrated with an equilibration buffer prior to loading the composition which is to be purified. In some examples, the wash buffer is used after loading the composition onto a chromatography material and before elution of the polypeptide of interest from the solid phase. However, some of the product of interest, e.g. a polypeptide, may be removed from the chromatography material by the wash buffer (e.g. similar to a flow-through mode).

Elution, as used herein, is the removal of the product, e.g. polypeptide, from the chromatography material. In some embodiments of the invention, the elution is a "mock elution" where an elution procedure is applied to a chromatography material for which a protein was not loaded subsequent of the last cleaning procedure. In some embodiments of the invention, the mock elution procedure is applied to a chromatography material following any one of the cleaning procedure described herein. In some embodiments, the mock elution mimics the elution that will be used to elute a protein that will be applied to the material in an effort to determine if there may be carryover material (e.g., contaminants) during the actual production run. A mock elution can be used as a means to evaluate the efficacy of the cleaning procedure.

Elution buffer is the buffer used to elute the polypeptide or other product of interest from a chromatography material. In many cases, an elution buffer has a different physical characteristic than the load buffer. For example, the elution buffer may have a different conductivity than load buffer or a different pH than the load buffer. In some embodiments, the elution buffer has a lower conductivity than the load buffer. In some embodiments, the elution buffer has a higher conductivity than the load buffer. In some embodiments, the elution buffer has a lower pH than the load buffer. In some embodiments, the elution buffer has a higher pH than the load buffer. In some embodiments the elution buffer has a different conductivity and a different pH than the load buffer. The elution buffer can have any combination of higher or lower conductivity and higher or lower pH.

Conductivity refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

(B) Contaminants

The invention provides methods for the reuse of chromatography materials for use on a large-scale such as a manufacturing-scale. The method provides for the multiple use of chromatography materials for multiple polypeptide products. For example, using the methods of the invention, a first antibody can be purified at an industrial scale on a chromatography material, followed by the methods of cleaning/regenerating the chromatography material described herein, and then followed by the industrial scale purification of a second antibody product. In some embodiments, the methods of the invention are used to reduce the "carryover" of previous products that were purified using the chromatography material. In some embodiments, the carryover contaminants include but are not limited to whole antibodies, IgG fragments, Fc, and Fc fragments.

In some embodiments of any of the methods described herein, the at least one contaminant is any one or more of host cell material, such as CHOP; leached Protein A; nucleic acid; a variant, fragment, aggregate or derivative of the desired polypeptide; another polypeptide; endotoxin; viral contaminant; cell culture media component, carboxypeptidase B, gentamicin, etc. In some examples, the contaminant may be a host cell protein (HCP) from, for example but not limited to, a bacterial cell such as an *E. coli* cell, an insect cell, a prokaryotic cell, a eukaryotic cell, a yeast cell, a mammalian cell, an avian cell, a fungal cell.

Leached Protein A is Protein A detached or washed from a solid phase to which it is bound. For example, leached Protein A can be leached from Protein A chromatography material. The amount of Protein A may be measured, for example, by ELISA. In some embodiments of any of the methods described herein, the amount of leached Protein A is reduced by greater than about any of 10%, 20%, 30%, 40%, 50%, 60%, 70%, 80%, or 90%. The amount of leached Protein A may be reduced by between about any of 10% and 99%, 30% and 95%, 30% and 99%, 50% and 95%, 50% and 99%, 75% and 99%, or 85% and 99%. In some embodiments, the amount of leached Protein A is reduced by about any of 10%, 20%, 30%, 40%, 50%, 60%, 70%, 80%, 90%, or 95%. In some embodiments, the reduction is determined by comparing the amount of leached Protein A in the composition recovered from a purification step(s) to the amount of leached Protein A in the composition before the purification step(s).

Host cell proteins (HCP) are proteins from the cells in which the polypeptide was produced. For example, CHOP are proteins from host cells, i.e., Chinese Hamster Ovary Proteins. The amount of CHOP may be measured by enzyme-linked immunosorbent assay ("ELISA") or Meso Scale Discovery ("MSO"). In some embodiments of any of the methods described herein, the amount of HCP (e.g. CHOP) in the eluate is at a minimum in a mock elution. In some embodiments, the level of host cell protein in an eluate from a mock elution is compared with and without cleaning method or before and after cleaning method.

Methods of measuring DNA such as host cell DNA are known in the art and described in the examples section. In some embodiments of any of the methods described herein, the amount of DNA is reduced by greater than about any of 10%, 20%, 30%, 40%, 50%, 60%, 70%, 80%, or 90%. The amount of DNA may be reduced by between about any of 10% and 99%, 30% and 95%, 30% and 99%, 50% and 95%, 50% and 99%, 75% and 99%, or 85% and 99%. The amount of DNA may be reduced by about any of 10%, 20%, 30%, 40%, 50%, 60%, 70%, 80%, 90%, 95%, or 99%. In some embodiments, the reduction is determined by comparing the amount of DNA in the composition recovered from a purification step(s) to the amount of DNA in the composition before the purification step(s).

Fragment polypeptide can be low molecular weight (LMW) protein. In some embodiments, the fragmented polypeptide is a fragment of the polypeptide of interest. Examples of LMW protein include, but not limited to, a Fab (Fragment antigen binding), Fc (fragment, crystallizable) regions or combination of both or any random fragmented part of an antibody of interest. Methods of measuring fragmented protein (e.g., LMW protein) are known in the art and described in the examples section. In some embodiments of any of the methods described herein, the amount of LMW protein is reduced by greater than about any of 5%, 10%, 20%, 30%, 40%, 50%, 60%, 70%, 80%, 90%, or 95%. The amount of LMW protein may be reduced by between about any of 10% and 99%, 30% and 95%, 30% and 99%, 50% and 95%, 50% and 99%, 75% and 99%, or 85% and 99%. The amount of LMW protein may be reduced by about any of 5%, 10%, 20%, 30%, 40%, 50%, 60%, 70%, 80%, 90%, or 95%. In some embodiments, the reduction is determined by comparing the amount of fragmented protein (e.g., LMW protein) in the composition recovered from a purification step(s) to the amount of fragmented protein (e.g., LMW protein) in the composition before the purification step(s).

Aggregated polypeptide can be high molecular weight (HMW) protein. In some embodiments, the aggregated polypeptide is multimers of the polypeptide of interest. The HMW protein may be a dimer, up to 8× monomer, or larger of the polypeptide of interest. Methods of measuring aggregated protein (e.g., HMW protein) are known in the art. In some embodiments, the level of HMW in a mock elution is at a minimum; e.g., less than about 5 ppm, less than about 4 ppm, less than about 3 ppm, less than about 2 ppm or less than about 1 ppm. In some embodiments of any of the methods described herein, the amount of aggregated protein is reduced by greater than about any of 5%, 10%, 20%, 30%, 40%, 50%, 60%, 70%, 80%, 90%, or 95%. The amount of aggregated protein may be reduced by between about any of 10% and 99%, 30% and 95%, 30% and 99%, 50% and 95%, 50% and 99%, 75% and 99%, or 85% and 99%. The amount of aggregated protein may be reduced by about any of 5%, 10%, 20%, 30%, 40%, 50%, 60%, 70%, 80%, 90%, or 95%. In some embodiments, the reduction is determined by comparing the amount of aggregated protein (e.g., HMW protein) in the composition recovered from a purification step(s) to the amount of aggregated protein (e.g., HMW protein) in the composition before the purification step(s).

Cell culture media component refers to a component present in a cell culture media. A cell culture media may be a cell culture media at the time of harvesting cells. In some embodiments, the cell culture media component is gentamicin. The amount of gentamicin may be measured by ELISA. In some embodiments of any of the methods described herein, the amount of cell culture media component is reduced by greater than about any of 10%, 20%, 30%, 40%, 50%, 60%, 70%, 80%, or 90%. The amount of cell culture media component may be reduced by between about any of 10% and 99%, 30% and 95%, 30% and 99%, 50% and 95%, 50% and 99%, 75% and 99%, or 85% and 99%. In some embodiments, the amount of cell culture media component is reduced by about any of 10%, 20%, 30%, 40%, 50%, 60%, 70%, 80%, 90%, 95%, or 98%. In some embodiments, the reduction is determined by comparing the amount of cell culture media component in the composition recovered from a purification step(s) to the amount of cell culture media component in the composition before the purification step(s).

(C) Methods to Detect Contaminants

The invention provides methods to evaluate the effectiveness of the cleaning of the reusable chromatography material. For example, a chromatography material in which a polypeptide had been previously loaded and eluted at least one time is cleaned by one of the methods of the invention described above. A mock elution is then run on the material where no additional polypeptide had been loaded on the material after the cleaning procedure. The mock elution may follow the elution procedure that was used on the polypeptide that was previously loaded on the material or the elution procedure may follow the elution procedure for the polypeptide that will be purified after the cleaning procedure. In some embodiments, a mock loading is run on the material prior to the mock elution. A mock loading uses the same procedure to load a polypeptide on the material with the exception that the polypeptide is not included in the loading. In some embodiments, the eluent from the mock elution is collected in one or more fractions. In some embodiments, the eluent of the mock elution is collected in a single fraction. In some embodiments, the eluent, or a sample of the eluent, is analyzed for contaminants including carryover polypeptides from the previous loading of the chromatography material, IgG fragments, leached protein A, CHOP and CHO DNA.

Polypeptide Quantification

The concentration of polypeptide such as an antibody can be determined via absorbance at 280 and 320 nm using a UV-visible spectrophotometer (8453 model G1103A; Agilent Technologies; Santa Clara, Calif., U.S.A.) or NanoDrop 1000 model ND-1000 (Thermo Fisher Scientific; Waltham, Mass., U.S.A.). Species other than the polypeptide previously loaded on the reusable chromatography material or the polypeptide loaded onto a material cleaned by the methods of the invention (i.e. impurities) may be too low in concentration to have an appreciable effect on UV absorbance. As needed, samples may be diluted with an appropriate non-interfering diluent in the range of 0.1-1.0 absorbance unit. Sample preparation and UV measurement are performed in duplicate and the average value is recorded. MAb absorption coefficients may range from 1.42 to 1.645/mg·ml·cm.

Total protein can be determined by a capillary zone electrophoresis/Laser-induced fluorescence detection assay.

IgG Detection

Intact human IgG and human IgG fragments may be detected using an intact human IgG-specific or IgG fragment-specific ELISA. Human Fc may be detected using a human Fc-specific ELISA.

CHO Host Cell Protein (CHOP) Quantification

An ELISA may be used to quantify the levels of the host cell protein called CHOP. Anti-CHOP antibodies are immobilized on microtiter plate wells. Dilutions of the samples containing CHOP, standards and controls are incubated in the wells, followed by incubation with anti-CHOP antibodies conjugated with horseradish peroxidase (HRP). The HRP enzymatic activity can be detected with o-phenylenediamine, and the CHOP is quantified by reading absorbance at 490 nm in a microtiter plate reader. Based on the principles of sandwich ELISA, the concentration of peroxidase corresponds to the CHOP concentration. The assay range for the ELISA is typically 5-320 ng/ml with intra-assay variability <10%. CHOP values may be reported in units of ng/ml. Alternatively, CHOP values may be divided by the MAb concentration and the results may be reported in PPM (parts per million; e.g. ng of CHOP/mg of MAb). The CHOP ELISA may be used to quantify total CHOP levels in a sample but does not quantify the concentration of individual proteins.

CHO DNA Quantification

CHO DNA in product samples may be quantified using real-time PCR (TaqMan PCR). DNA from samples and controls may first be extracted using Qiagen's Virus Biorobot kit. The extracted samples, controls, and standard DNA, are subject to TaqMan real time Polymerase chain reaction (PCR) using PCR primers and probe in a 96-well plate with ABI's sequence detection system. The primers are defined by a 110 base pair segment of a repetitive DNA sequence in the *Cricetulus griseus* genome. The probe is labeled with a fluorescent reporter dye at 5' end and a quencher dye at the 3' end. When the probe is intact, the emission spectrum of the reporter is suppressed by the quencher. The 5' nuclease activity of polymerase hydrolyzes the probe and releases the report, which results in an increase in fluorescence emission. The sequence detector quantifies the amplified product in direct proportion to the increase in fluorescence emission measured continuously during the DNA amplification. Cycle numbers at which DNA had amplifies past the threshold (CT) are calculated for the standard curve. A standard curve ranging 1 pg/mL-10,000 pg/mL may be generated, which is used for quantifying DNA in samples.

Leached Protein a Quantification

The level of leached Protein-A in the Protein A pools may be determined by a sandwich Protein-A ELISA. Chicken anti-staphylococcal protein A antibodies are immobilized on microtiter plate wells. The sample treatment procedure may include sample dilution and dissociation of the Protein A/IgG complex using microwave assisted heating as a pretreatment step before running the samples on a sandwich ELISA. Protein A, if present in the sample, may bind to the coated antibody. Bound protein A is detected using horseradish peroxidase conjugated anti-protein antibodies. Horseradish peroxidase enzymatic activity is quantified with a two component TMB substrate solution which produces a colorimetric signal.

III. Polypeptides

The methods of the invention may be used to clean chromatography material used in the purification of multiple polypeptides. In some embodiments, the chromatography material is used in large-scale; e.g., manufacturing-scale production of polypeptides such as antibodies or fragments thereof. In some embodiments, a chromatography material is used in the purification of a first polypeptide, such as a first antibody, the material is then cleaned by the methods of the invention, and then the chromatography material can be used to purify a second polypeptide, such as a second antibody. In some embodiments, the cleaning is effective such that the preparation comprising the second purified polypeptide is essentially free of the first polypeptide. In some embodiments, the preparation comprising the second purified polypeptide (e.g. a second antibody) comprises less than 1 ppm of the first polypeptide (e.g. a first antibody). In some embodiments, the second purified polypeptide comprises less than any one of 1 ppm, 2 ppm, 3 ppm, 4 ppm, 5 ppm, 10 ppm, 20 ppm, 30 ppm, 40 ppm, 50 ppm or 100 ppm of the first polypeptide.

In some embodiments, the methods of the invention are used to reuse chromatography material used to purify therapeutic polypeptides. In some embodiments, the polypeptide is an antagonist. In some embodiments, the polypeptide is an agonist. In some embodiments, the polypeptide is an antibody. In some embodiments, the polypeptide is epitope tagged. In some embodiments, the polypeptide retains a biological and/or immunological activity. In some embodiments, the polypeptide is an antagonist. In some embodiments, the polypeptide initiates complement dependent cytotoxicity. In some embodiments the polypeptide is an antibody or immunoadhesin.

In some embodiments, the polypeptide, the first polypeptide and/or the second polypeptide, has a molecular weight of greater than about any of 5,000 Daltons, 10,000 Daltons, 15,000 Daltons, 25,000 Daltons, 50,000 Daltons, 75,000 Daltons, 100,000 Dalton, 125,000 Daltons, or 150,000 Daltons. The polypeptide may have a molecular weight between about any of 50,000 Daltons to 200,000 Daltons or 100,000 Daltons to 200,000 Daltons. Alternatively, the polypeptide for use herein may have a molecular weight of about 120,000 Daltons or about 25,000 Daltons.

pI is the isoelectric point and is the pH at which a particular molecule or surface carries no net electrical charge. In some embodiments of any of the methods described herein, the pI of the polypeptide, e.g. the first polypeptide and/or the second polypeptide, may be between about any of 6 to 10, 7 to 9, or 8 to 9. In some embodiments, the polypeptide has a pI of about any of 6, 7, 7.5, 8, 8.5, 9, 9.5, or 10.

The polypeptides to be purified using reusable chromatography material cleaned by the methods described herein are generally produced using recombinant techniques. Methods for producing recombinant proteins are described, e.g., in U.S. Pat. Nos. 5,534,615 and 4,816,567, specifically incorporated herein by reference. In some embodiments, the protein of interest is produced in a CHO cell (see, e.g. WO 94/11026). When using recombinant techniques, the polypeptides can be produced intracellularly, in the periplasmic space, or directly secreted into the medium.

The polypeptides to be purified using reusable chromatography material cleaned by the methods described herein may be recovered from culture medium or from host cell lysates. Cells employed in expression of the polypeptides can be disrupted by various physical or chemical means, such as freeze-thaw cycling, sonication, mechanical disruption, or cell lysing agents. If the polypeptide is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating polypeptides which are secreted to the periplasmic space of *E. coli*. Briefly, cell paste is thawed in the presence of sodium acetate (pH 3.5), EDTA, and phenylmethylsulfonylfluoride (PMSF) over about 30 min Cell debris can be removed by centrifugation. Where the polypeptide is secreted into the medium, supernatants from such expression systems are generally first concentrated using a commercially available polypeptide concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Examples of polypeptides that may be purified using reusable chromatography material cleaned by the methods described herein include but are not limited to immunoglobulins, immunoadhesins, antibodies, enzymes, hormones, fusion proteins, Fc-containing proteins, immunoconjugates, cytokines and interleukins. Examples of polypeptide include, but are not limited to, mammalian proteins, such as, e.g., renin; a hormone; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; an enzyme; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); a cytokine; CD proteins such as CD3, CD4, CD8, CD19 and CD20; erythropoietin; osteoinductive factors; immunotoxins; a fusion polypeptide, i.e. a polypeptide comprised on two or more heterologous polypeptides or fragments thereof and encoded by a recombinant nucleic acid; an Fc-containing polypeptide, for example, a fusion protein comprising an immunoglobulin Fc region, or fragment thereof, fused to a second polypeptide; an immunoconjugate; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as CA125 (ovarian cancer antigen) or HER2, HER3 or HER4 receptor; immunoadhesins; and fragments and/or variants of any of the above-listed proteins as well as antibodies, including antibody fragments, binding to a protein, including, for example, any of the above-listed proteins.

(A) Antibodies

In some embodiments of any of the methods described herein, the polypeptide that may be purified using reusable chromatography material cleaned by the methods described herein, e.g. the first polypeptide, the second polypeptide or any subsequent polypeptides, is an antibody.

Molecular targets for antibodies include CD proteins and their ligands, such as, but not limited to: (i) CD3, CD4, CD8, CD19, CD11a, CD20, CD22, CD34, CD40, CD79α (CD79a), and CD79β (CD79b); (ii) members of the ErbB receptor family such as the EGF receptor, HER2, HER3 or HER4 receptor; (iii) cell adhesion molecules such as LFA-1, Macl, p150,95, VLA-4, ICAM-1, VCAM and αv/β3 integrin, including either alpha or beta subunits thereof (e.g., anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, β7 etc; and (v) cell surface and transmembrane tumor-associated antigens (TAA), such as those described in U.S. Pat. No. 7,521,541.

Other exemplary antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11a antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

(i) Polyclonal Antibodies

In some embodiments, the antibodies are polyclonal antibodies. Polyclonal antibodies are preferably raised in animals by multiple subcutaneous (sc) or intraperitoneal (ip) injections of the relevant antigen and an adjuvant. It may be useful to conjugate the relevant antigen to a polypeptide that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the polypeptide or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. In some embodiments, the animal is boosted with the conjugate of the same antigen, but conjugated to a different polypeptide and/or through a different cross-linking reagent. Conjugates also can be made in recombinant cell culture as polypeptide fusions. Also, aggregating agents such as alum are suitably used to enhance the immune response.

(ii) Monoclonal Antibodies

In some embodiments, the antibodies purified on reusable chromatography material cleaned by the methods of the invention are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature* 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133:3001 (1984); Brodeur et al., *Monoclonal Antibody Production Techniques and Applications* pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.* 107:220 (1980).

After hybridoma cells are identified that produce antibodies of the desired specificity, affinity, and/or activity, the clones may be subcloned by limiting dilution procedures and grown by standard methods (*Goding, Monoclonal Antibodies: Principles and Practice* pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., *Curr. Opinion in Immunol.* 5:256-262 (1993) and Plückthun, *Immunol. Revs.*, 130:151-188 (1992).

In a further embodiment, antibodies or antibody fragments can be isolated from antibody phage libraries generated using the techniques described in McCafferty et al., *Nature* 348:552-554 (1990). Clackson et al., *Nature* 352: 624-628 (1991) and Marks et al., *J. Mol. Biol.* 222:581-597 (1991) describe the isolation of murine and human antibodies, respectively, using phage libraries. Subsequent publications describe the production of high affinity (nM range) human antibodies by chain shuffling (Marks et al., *Bio/Technology* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., *Proc. Natl Acad. Sci. USA* 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.
(iii) Humanized Antibodies In some embodiments, the antibody is a humanized antibody. Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature* 321:522-525 (1986); Riechmann et al., *Nature* 332:323-327 (1988); Verhoeyen et al., *Science* 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.* 151:2296 (1993); Chothia et al., *J. Mol. Biol.* 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA* 89:4285 (1992); Presta et al., *J. Immunol.* 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.
(v) Human Antibodies In some embodiments, the antibody is a human antibody. As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669; 5,589,369; and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat polypeptide gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229,275).

(v) Antibody Fragments

In some embodiments, the antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894 and 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab' fragment, a F(ab')$_2$ fragment, a scFv, a Fv, and a diabody.

(vi) Bispecific Antibodies

In some embodiments, the antibody is a bispecific antibody. Bispecific antibodies are antibodies that have binding specificities for at least two different epitopes. Exemplary bispecific antibodies may bind to two different epitopes. Alternatively, a bispecific antibody binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the cell. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers that are recovered from recombinant cell culture. In some embodiments, the interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.* 152:5368 (1994).

Antibodies with more than two valencies are contemplated. For example, trispecific antibodies can be prepared. Tutt et al., *J. Immunol.* 147: 60 (1991).

(vii) Multivalent Antibodies

In some embodiments, the antibodies are multivalent antibodies. A multivalent antibody may be internalized (and/or catabolized) faster than a bivalent antibody by a cell expressing an antigen to which the antibodies bind. The antibodies provided herein can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2) n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

In some embodiments, the antibody is a multispecific antibody. Example of multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. In some embodiment that antibody has polyepitopic specificity; for example, the ability to specifically bind to two or more different epitopes on the same or different target(s). In some embodiments, the antibodies are monospecific; for example, an antibody that binds only one epitope. According to one embodiment the multispecific antibody is an IgG antibody that binds to each epitope with an affinity of 5 μM to 0.001 pM, 3 μM to 0.001 pM, 1 μM to 0.001 pM, 0.5 μM to 0.001 pM, or 0.1 μM to 0.001 pM.

(viii) Other Antibody Modifications

It may be desirable to modify the antibody provided herein with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J., Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement mediated lysis and ADCC capabilities. See Stevenson et al., *Anti-Cancer Drug Design* 3:219-230 (1989).

For increasing serum half the serum half-life of the antibody, amino acid alterations can be made in the antibody as described in US 2006/0067930, which is hereby incorporated by reference in its entirety.

(B) Polypeptide Variants and Modifications

Amino acid sequence modification(s) of the polypeptides, including antibodies, described herein may be used in reusable chromatography material cleaned by the methods of described herein.

(i) Variant Polypeptides

"Polypeptide variant" means a polypeptide, preferably an active polypeptide, as defined herein having at least about 80% amino acid sequence identity with a full-length native sequence of the polypeptide, a polypeptide sequence lacking the signal peptide, an extracellular domain of a polypeptide, with or without the signal peptide. Such polypeptide variants include, for instance, polypeptides wherein one or more amino acid residues are added, or deleted, at the N or C-terminus of the full-length native amino acid sequence. Ordinarily, a TAT polypeptide variant will have at least about 80% amino acid sequence identity, alternatively at least about any of 85%, 90%, 95%, 96%, 97%, 98%, or 99% amino acid sequence identity, to a full-length native sequence polypeptide sequence, a polypeptide sequence lacking the signal peptide, an extracellular domain of a polypeptide, with or without the signal peptide. Optionally, variant polypeptides will have no more than one conservative amino acid substitution as compared to the native polypeptide sequence, alternatively no more than about any of 2, 3, 4, 5, 6, 7, 8, 9, or 10 conservative amino acid substitution as compared to the native polypeptide sequence.

The variant polypeptide may be truncated at the N-terminus or C-terminus, or may lack internal residues, for example, when compared with a full length native polypeptide. Certain variant polypeptides may lack amino acid residues that are not essential for a desired biological activity. These variant polypeptides with truncations, deletions, and insertions may be prepared by any of a number of conventional techniques. Desired variant polypeptides may be chemically synthesized. Another suitable technique involves isolating and amplifying a nucleic acid fragment encoding a desired variant polypeptide, by polymerase chain reaction (PCR). Oligonucleotides that define the desired termini of the nucleic acid fragment are employed at the 5' and 3' primers in the PCR. Preferably, variant polypeptides share at least one biological and/or immunological activity with the native polypeptide disclosed herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

For example, it may be desirable to improve the binding affinity and/or other biological properties of the polypeptide Amino acid sequence variants of the polypeptide are prepared by introducing appropriate nucleotide changes into the antibody nucleic acid, or by peptide synthesis. Such modifications include, for example, deletions from, and/or insertions into and/or substitutions of, residues within the amino acid sequences of the polypeptide. Any combination of deletion, insertion, and substitution is made to arrive at the final construct, provided that the final construct possesses the desired characteristics. The amino acid changes also may alter post-translational processes of the polypeptide (e.g., antibody), such as changing the number or position of glycosylation sites.

Guidance in determining which amino acid residue may be inserted, substituted or deleted without adversely affecting the desired activity may be found by comparing the sequence of the polypeptide with that of homologous known polypeptide molecules and minimizing the number of amino acid sequence changes made in regions of high homology.

A useful method for identification of certain residues or regions of the polypeptide (e.g., antibody) that are preferred locations for mutagenesis is called "alanine scanning mutagenesis" as described by Cunningham and Wells, *Science* 244:1081-1085 (1989). Here, a residue or group of target residues are identified (e.g., charged residues such as Arg, Asp, His, Lys, and Glu) and replaced by a neutral or negatively charged amino acid (most preferably Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table 1 below under the heading of "preferred substitutions." If such substitutions result in a change in biological activity, then more substantial changes, denominated "exemplary substitutions" in the Table 1, or as further described below in reference to amino acid classes, may be introduced and the products screened.

TABLE 1

Exemplary amino acid substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain Amino acids may be grouped according to similarities in the properties of their side chains (in A. L. Lehninger, Biochemistry second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the polypeptide to improve its stability (particularly where the antibody is an antibody fragment such as an Fv fragment).

A particularly preferred type of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the polypeptide alters the original glycosylation pattern of the antibody. The polypeptide may comprise non-amino acid moieties. For example, the polypeptide may be glycosylated. Such glycosylation may occur naturally during expression of the polypeptide in the host cell or host organism, or may be a deliberate modification arising from human intervention. By altering is meant deleting one or more carbohydrate moieties found in the polypeptide, and/or adding one or more glycosylation sites that are not present in the polypeptide.

Glycosylation of polypeptide is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Removal of carbohydrate moieties present on the polypeptide may be accomplished chemically or enzymatically or by mutational substitution of codons encoding for amino acid residues that serve as targets for glycosylation. Enzymatic cleavage of carbohydrate moieties on polypeptides can be achieved by the use of a variety of endo- and exo-glycosidases.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group.

(ii) Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

In an alternative embodiment, the chimeric molecule may comprise a fusion of the polypeptide with an immunoglobulin or a particular region of an immunoglobulin. A bivalent form of the chimeric molecule is referred to as an "immunoadhesin."

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The Ig fusions preferably include the substitution of a soluble (transmembrane domain deleted or inactivated) form of a polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule.

(iii) Polypeptide Conjugates

The polypeptide for use in polypeptide formulations may be conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such conjugates can be used. In addition, enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated polypeptides. Examples include $^{212}Bi$, $^{131}I$, $^{131}In$, $^{90}Y$, and $^{186}Re$. Conjugates of the polypeptide and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the polypeptide.

Conjugates of a polypeptide and one or more small molecule toxins, such as a calicheamicin, maytansinoids, a trichothene, and CC1065, and the derivatives of these toxins that have toxin activity, are also contemplated herein.

Maytansinoids are mitototic inhibitors which act by inhibiting tubulin polymerization. Maytansine was first isolated from the east African shrub *Maytenus serrata*. Subsequently, it was discovered that certain microbes also produce maytansinoids, such as maytansinol and C-3 maytansinol esters. Synthetic maytansinol and derivatives and analogues thereof are also contemplated. There are many linking groups known in the art for making polypeptide-maytansinoid conjugates, including, for example, those disclosed in U.S. Pat. No. 5,208,020. The linking groups include disufide groups, thioether groups, acid labile groups, photolabile groups, peptidase labile groups, or esterase labile groups, as disclosed in the above-identified patents, disulfide and thioether groups being preferred.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Another conjugate of interest comprises a polypeptide conjugated to one or more calicheamicin molecules. The calicheamicin family of antibiotics are capable of producing double-stranded DNA breaks at sub-picomolar concentrations. For the preparation of conjugates of the calicheamicin family, see, e.g., U.S. Pat. No. 5,712,374. Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$. Another anti-tumor drug that the antibody can be conjugated is QFA which is an antifolate. Both calicheamicin and QFA have intracellular sites of action and do not readily cross the plasma membrane. Therefore, cellular uptake of these agents through polypeptide (e.g., antibody) mediated internalization greatly enhances their cytotoxic effects.

Other antitumor agents that can be conjugated to the polypeptides described herein include BCNU, streptozoicin, vincristine and 5-fluorouracil, the family of agents known collectively LL-E33288 complex, as well as esperamicins.

In some embodiments, the polypeptide may be a conjugate between a polypeptide and a compound with nucleolytic activity (e.g., a ribonuclease or a DNA endonuclease such as a deoxyribonuclease; DNase).

In yet another embodiment, the polypeptide (e.g., antibody) may be conjugated to a "receptor" (such streptavidin) for utilization in tumor pre-targeting wherein the polypeptide receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In some embodiments, the polypeptide may be conjugated to a prodrug-activating enzyme which converts a prodrug (e.g., a peptidyl chemotherapeutic agent) to an active anti-cancer drug. The enzyme component of the immunoconjugate includes any enzyme capable of acting on a prodrug in such a way so as to covert it into its more active, cytotoxic form.

Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs into free active drugs.

(iv) Other

Another type of covalent modification of the polypeptide comprises linking the polypeptide to one of a variety of nonproteinaceous polymers, e.g., polyethylene glycol, polypropylene glycol, polyoxyalkylenes, or copolymers of polyethylene glycol and polypropylene glycol. The polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 18th edition, Gennaro, A. R., Ed., (1990).

IV. Obtaining Polypeptides for Use in the Formulations and Methods

The polypeptides to be purified using reusable chromatography material cleaned by the methods described herein may be obtained using methods well-known in the art, including the recombination methods. The following sections provide guidance regarding these methods.

(A) Polynucleotides

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region ($V_H$) but also a heavy chain constant region ($C_H$), which typically will comprise three constant domains: $C_H1$, $C_H2$ and $C_H3$; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and F(ab')$_2$ and "minibodies." Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above. Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions.

Suitably, the polynucleotides described herein may be isolated and/or purified. In some embodiments, the polynucleotides are isolated polynucleotides.

The term "isolated polynucleotide" is intended to indicate that the molecule is removed or separated from its normal or natural environment or has been produced in such a way that it is not present in its normal or natural environment. In some embodiments, the polynucleotides are purified polynucleotides. The term purified is intended to indicate that at least some contaminating molecules or substances have been removed.

Suitably, the polynucleotides are substantially purified, such that the relevant polynucleotides constitutes the dominant (i.e., most abundant) polynucleotides present in a composition.

(B) Expression of Polynucleotides

The description below relates primarily to production of polypeptides by culturing cells transformed or transfected with a vector containing polypeptide-encoding polynucleotides. It is, of course, contemplated that alternative methods, which are well known in the art, may be employed to prepare polypeptides. For instance, the appropriate amino acid sequence, or portions thereof, may be produced by direct peptide synthesis using solid-phase techniques (see, e.g., Stewart et al., *Solid-Phase Peptide Synthesis* W.H. Freeman Co., San Francisco, Calif. (1969); Merrifield, *J. Am. Chem. Soc.* 85:2149-2154 (1963)). In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the polypeptide may be chemically synthesized separately and combined using chemical or enzymatic methods to produce the desired polypeptide.

Polynucleotides as described herein are inserted into an expression vector(s) for production of the polypeptides. The term "control sequences" refers to DNA sequences necessary for the expression of an operably linked coding sequence in a particular host organism. The control sequences include, but are not limited to, promoters (e.g., naturally-associated or heterologous promoters), signal sequences, enhancer elements, and transcription termination sequences.

A polynucleotide is "operably linked" when it is placed into a functional relationship with another polynucleotide sequence. For example, nucleic acids for a presequence or secretory leader is operably linked to nucleic acids for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

For antibodies, the light and heavy chains can be cloned in the same or different expression vectors. The nucleic acid segments encoding immunoglobulin chains are operably linked to control sequences in the expression vector(s) that ensure the expression of immunoglobulin polypeptides.

The vectors containing the polynucleotide sequences (e.g., the variable heavy and/or variable light chain encoding sequences and optional expression control sequences) can be transferred into a host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection. For production of transgenic animals, transgenes can be microinjected into fertilized oocytes, or can be incorporated into the genome of embryonic stem cells, and the nuclei of such cells transferred into enucleated oocytes.

(C) Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *Escherichia coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

Vectors may be transformed into a suitable host cell as described below to provide for expression of a polypeptide. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

The vectors may be for example, plasmid, virus or phage vectors provided with an origin of replication, optionally a promoter for the expression of the said polynucleotide and optionally a regulator of the promoter. Vectors may contain one or more selectable marker genes which are well known in the art.

These expression vectors are typically replicable in the host organisms either as episomes or as an integral part of the host chromosomal DNA.

(D) Host Cells

The host cell may be a bacterium, a yeast or other fungal cell, insect cell, a plant cell, or a mammalian cell, for example.

A transgenic multicellular host organism which has been genetically manipulated may be used to produce a polypeptide. The organism may be, for example, a transgenic mammalian organism (e.g., a transgenic goat or mouse line).

Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P), *Pseudomonas* such as *P. aeruginosa*, and *Streptomyces*. These examples are illustrative rather than limiting. Strain W3110 is one particularly preferred host or parent host because it is a common host strain for recombinant polynucleotide product fermentations. Preferably, the host cell secretes minimal amounts of proteolytic enzymes. For example, strain W3110 may be modified to effect a genetic mutation in the genes encoding polypeptides endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan; *E. coli* W3110 strain 37D6, which has the complete genotype tonA ptr3 phoA E15 (argF-lac)169 degP ompT rbs7 ilvG kan; *E. coli* W3110 strain 40B4, which is strain 37D6 with a non-kanamycin resistant degP deletion mutation; and an *E. coli* strain having mutant periplasmic protease. Alternatively, in vitro methods of cloning, e.g., PCR or other nucleic acid polymerase reactions, are suitable.

In these prokaryotic hosts, one can make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Eukaryotic microbes may be used for expression. Eukaryotic microbes such as filamentous fungi or yeast are suitable cloning or expression hosts for polypeptide-encoding vectors. *Saccharomyces cerevisiae* is a commonly used lower eukaryotic host microorganism. Others include *Schizosaccharomyces pombe; Kluyveromyces* hosts such as, e.g., *K. lactis* (MW98-8C, CBS683, CBS4574), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris; Candida; Trichoderma reesia; Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans*, and *A. niger*. Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides as described herein and in some instances are preferred (See Winnacker, *From Genes to Clones* VCH Publishers, N.Y., N.Y. (1987). For some embodiments, eukaryotic cells may be preferred, because a number of suitable host cell lines capable of secreting heterologous polypeptides (e.g., intact immunoglobulins) have been developed in the art, and include CHO cell lines, various Cos cell lines, HeLa cells, preferably, myeloma cell lines, or transformed B-cells or hybridomas. In some embodiments, the mammalian host cell is a CHO cell.

In some embodiments, the host cell is a vertebrate host cell. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/–DHFR(CHO or CHO-DP-12 line); mouse sertoli cells; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

V. Exemplary Embodiments

In some embodiments, the invention provides the following:

1. A method to clean a chromatography material for reuse, the method comprising the steps of a) passing two or more material volumes of elution buffer through the material, wherein the elution buffer comprises about 0.15 M acetic acid and is about pH 2.9; b) statically holding the material in elution buffer for a time ranging from about 10 minutes to about 30 minutes; c) passing about two or more material volumes of elution buffer through the material; and d) passing about two or more material volumes of regeneration buffer through the material, wherein the regeneration buffer comprises about 0.1 N NaOH and is about pH 13.

2. A method to clean a chromatography material for reuse, the method comprising the steps of a) passing about two material volumes of elution buffer through the material, wherein the elution buffer comprises about 0.15 M acetic acid and is about pH 2.9; b) statically holding the material in elution buffer for about 30 minutes; c) passing about two material volumes of elution buffer through the material; and d) passing about four material volumes of regeneration buffer through the material, wherein the regeneration buffer comprises about 0.1 N NaOH and is about pH 13.

3. A method to clean a chromatography material for reuse, the method comprising the steps of a) passing about two material volumes of elution buffer through the material, wherein the elution buffer comprises about 0.15 M acetic acid and is about pH 2.9, b) statically holding the material in elution buffer for about 30 minutes, c) passing about two material volumes of elution buffer through the material, and d) passing about two and one-half material volumes of regeneration buffer through the material, wherein the regeneration buffer comprises about 0.1 N NaOH and is about pH 13, e) statically holding the material in regeneration buffer for about 30 minutes, f) passing about two and one-half material volumes of regeneration buffer through the material.

4. A method to clean a chromatography material for reuse, the method comprising the steps of a) passing about two material volumes of equilibration buffer through the material, wherein the equilibration buffer comprises about 25 mM Tris and about 25 mM NaCl and is about pH 7.1; b) statically holding the material in equilibration buffer for about 30 minutes; c) passing about two material volumes of equilibration buffer through the material; d) passing about two material volumes of elution buffer through the material, wherein the elution buffer comprises about 0.15 M Acetic acid and is about pH 2.8; e) statically holding the material in elution buffer for about 30 minutes; f) passing about two material volumes of elution buffer through the material; g) passing about two material volumes of regeneration buffer through the material, wherein the regeneration buffer comprises 0.1 N NaOH, pH 13; h) statically holding the material in regeneration buffer for about 30 minutes; i) passing about two material volumes of regeneration buffer through the material.

5. A method to clean a chromatography material for reuse, the method comprising the steps of a) passing about four material volumes of equilibration buffer through the material, wherein the equilibration buffer comprises about 25 mM Tris and about 25 mM NaCl and is pH 7.1; b) performing six cycles of the steps comprising i) passing about three material volumes of elution buffer through the material, wherein the elution buffer comprises about 0.15 M Acetic acid and is about pH 2.8; ii) statically holding the material in elution buffer for about 10 minutes; iii) passing about one material volume of elution buffer through the material; iv) passing about three material volumes of regeneration buffer through the material, wherein the regeneration buffer comprises about 0.1 N NaOH and is about pH 13; v) statically holding the material in regeneration buffer for about 10 minutes; vi) passing about one material volume of regeneration buffer through the material.

6. A method to clean a chromatography material for reuse, the method comprising six cycles of the steps of a) passing about three material volumes of elution buffer through the material, wherein the elution buffer comprises about 0.15 M Acetic acid and is about pH 2.8; b) statically holding the material in elution buffer for about 15 minutes; c) passing about one material volume of elution buffer through the material; d) passing about three material volumes of regeneration buffer through the material, wherein the regeneration buffer comprises about 0.1 N NaOH and is about pH 13; e) statically holding the material in regeneration buffer for about 15 minutes; f) passing about one material volume of regeneration buffer through the material; g) passing about three material volumes of storage buffer through the material, wherein the storage buffer comprises about 100 mM sodium acetate, about 2% benzyl alcohol, and is about pH 5.0; e) statically holding the material in storage buffer for about 15 minutes; f) passing about one material volume of storage buffer through the material.

7. The method of any one of embodiments 1-6, wherein the chromatography material is in a chromatography column.

8. The method of any one of embodiments 1-7, wherein the chromatography material is an affinity material.

9. The method of embodiment 8, wherein the affinity material is a protein A affinity material.

10. The method of embodiment 9, wherein the protein A affinity material is a MAbSelect material, a MAbSelect SuRe material or a MAbSelect SuRe LX material.

11. The method of any one of embodiments 1-10, wherein the chromatography material is used for large-scale production of a polypeptide.

12. A method to clean a chromatography material for reuse, the method comprising the steps of a) passing about three material volumes of equilibration buffer through the material, wherein the equilibration buffer comprises about 40 mM sodium acetate and is about pH 5.5; b) passing about two material volumes of about 0.5 N NaOH through the material c) statically holding the material in about 0.5 N NaOH for about 10 minutes; d) passing about one material volume of about 0.5 N NaOH through the material; and e) statically holding the material in about 0.5 N NaOH for about 10 minutes; f) passing about one material volume of about 0.5 N NaOH through the material.

13. The method of embodiment 12, wherein the chromatography material is in a chromatography column.

14. The method of embodiment 12 or 13, wherein the chromatography material is an ion exchange material.

15. The method of embodiment 14 herein the ion exchange material is a cation exchange material.

16. The method of embodiment 15, wherein the cation exchange material is a POROS HS50 material.

17. The method of any one of embodiments 12-16, wherein the chromatography material is used for large-scale production of an antibody.

18. A method to clean a chromatography material for reuse, the method comprising the steps of a) passing about three material volumes of equilibration buffer through the material, wherein the equilibration buffer comprises about 50 mM Tris, 85 mM sodium acetate and is about pH 8.8 and about 8.6 mS/cm; b) passing about two material volumes of about 0.5 N NaOH through the material; c) statically holding the material in about 0.5 N NaOH for about 10 minutes; d) passing about one material volume of about 0.5 N NaOH through the material; and e) statically holding the material in about 0.5 N NaOH for about 10 minutes; f) passing about one material volume of about 0.5 N NaOH through the material.

19. The method of embodiment 18, wherein the chromatography material is in a chromatography column.

20. The method of embodiment 18 or 19, wherein the chromatography material is an ion exchange material.

21. The method of embodiment 20, wherein the ion exchange material is an anion exchange material.

22. The method of embodiment 21, wherein the anion exchange material is a QSFF material.

23. The method of any one of embodiments 18-22, wherein the chromatography material is used for large-scale production of an antibody.

24. The method of any one of embodiments 1-23, wherein the buffers are passed through the material at about 30 material volumes/hour, about 20 material volumes/hour or about 15 material volumes/hour.

25. The method of any one of embodiments 1-24, wherein the buffer is passed through the material in a downflow direction or an upflow direction.

26. The method of any one of embodiments 1-25, wherein the cleaning of the chromatography material is measured by running a mock elution after cleaning the chromatography material.

27. The method of embodiment 26, wherein an eluent of the mock elution comprising one or more of <0.25 mg/mL total protein, <1 ppm IgG fragments, <1 ppm leached protein A, <1 µg/mL CZE LIF, <1 ppm CHOP, and <1 pg/mL CHO DNA indicates effective cleaning of the material for multiproduct use.

28. The method of any one of embodiments 1-27, wherein the chromatography material is stable in alkali.

29. The method of any one of embodiments 1-28, wherein the chromatography material is used to purify a polypeptide.

30. The method of any one of embodiments 1-29, wherein the chromatography material is cleaned following purification of a first polypeptide and wherein the chromatography material is used to purify a second polypeptide following the cleaning.

31. The method of embodiment 30, wherein the polypeptide is an antibody or immunoadhesin.

32. The method of embodiment 31, wherein the polypeptide is an immunoadhesin.

33. The method of embodiment 31, wherein the polypeptide is an antibody.

34. The method of embodiment 33, wherein the antibody is a monoclonal antibody.

35. The method of embodiment 34, wherein the monoclonal antibody is a chimeric antibody, humanized antibody, or human antibody.

36. The method of embodiment 35, wherein the monoclonal antibody is an IgG monoclonal antibody.

37. The method of embodiment 36, wherein the antibody is an antigen binding fragment.

38. The method of embodiment 37, wherein the antigen binding fragment is a Fab fragment, a Fab' fragment, a F(ab')2 fragment, a scFv, a di-scFv, a bi-scFv, a tandem (di, tri)-scFv, a Fv, a sdAb, a tri-functional antibody, a BiTE, a diabody or a triabody.

39. The method of embodiment 38, wherein the polypeptide is an enzyme, a hormone, a fusion protein, an Fc-containing protein, an immunoconjugate, a cytokine or an interleukin.

40. The method of embodiment 30, wherein the first polypeptide is a first antibody or a first immunoadhesin and the second polypeptide is a second antibody or second immunoadhesin.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further details of the invention are illustrated by the following non-limiting Examples. The disclosures of all references in the specification are expressly incorporated herein by reference.

EXAMPLES

The examples below are intended to be purely exemplary of the invention and should therefore not be considered to limit the invention in any way. The following examples and detailed description are offered by way of illustration and not by way of limitation.

Example 1. Protein Carryover

This example describes an effort to quantify protein carryover from sample to sample a pre-cleaning test run was performed on lab scale using a standard Protein A affinity material (0.66×20 cm). This run was called a "mock run" as the process was run according to a standard purification procedure except the load cycle was simulated with the equilibration buffer. The elution pool was collected, as per a typical Protein A process, and analyzed to determine the presence of protein. The analysis revealed that 20-30 ppm of protein carryover was present in the "mock elution" in the absence of any additional column cleaning. The result was confirmed with a second run.

In order to determine safe carryover levels, a risk assessment was conducted to determine acceptable immunoglobulins (IgG) and protein carryover levels in mAbs, and a substance-specific Acceptable Daily Exposure (ADE) for IgG was calculated. A comparison of the ADE to EDI, resulted in a "worst case" x-fold safety margin (e.g., see OCTAGAM®; Product Approval Information Summary Basis of Approval OCTAGAM® 5%. OCTAPHARMA Pharmazeutika: Vienna, Austria. August, 2002 on the world wide web at fda.gov/downloads/BiologicsBloodVaccines/ BloodBloodProducts/ApprovedProducts/LicensedP rod- uctsBLAs/FractionatedPlasmaProducts/ucm064955.pdf as accessed on Aug. 7, 2012. The "worst-case" safety margin is the highest value of IgG carryover allowed from a previous sample, and this value is set at 10 μg mAb A/ml mAb B or 1000 ppm. Where mAb A is the carried over mAb and mAb B is the desired mAb of interest (Teschner, W., et al., *Vox Sang.* 2007, 92:42-55; Food and Drug Administration, HHS. Guidance for Industry Estimating the Maximum Safe Starting Dose in Initial Clinical Trials for Therapeutics in Adult Healthy Volunteers. Rockville, Md. July 2005 on the world wide web at google.com/url?sa=t&rct=j&q=&esrc= s& source=web&cd=1&ved=0CE8QFjAA&url=http %3A %2F %2Fwww.fda.gov %2Fdow nloads %2FDrugs%2F...%2 FGuidances%2FUCM078932.pdf&ei=f4QhUJv4K9Ov6g- GQ-4DgAg&usg=AFQjCNFbTE75U0nDbFpfdpxK85uW- XT8frg as accessed on Aug. 7, 2012; European Medicines Agency. Impurities: Residual Solvents, Note for Guidance on Impurities: Residual Solvents (CPMP/ICH/283/95). London, UK September 1997 on the world wide web at ema.europa.eu/ema/index.jsp?curl=pages/regulation/general/general_ con- tent_000431.jsp&mid=WC0b01ac0580029593 as accessed on Aug. 7, 2012; OCTAGAM®; Product Approval Information Summary Basis of Approval OCTAGAM® 5%. OCTAPHARMA Pharmazeutika: Vienna, Austria. August, 2002 on the world wide web at fda.gov/downloads/BiologicsBloodVaccines/BloodBlood- Products/ApprovedProducts/LicensedProductsBLAs/Fract ionatedPlasmaProducts/ucm- 064955.pdf as accessed on Aug. 7, 2012.

Materials and Methods

Equipment

AKTA explorer 100 system: A standard AKTA explorer 100 chromatography system from GE Healthcare (Uppsala, Sweden) was used for experimentation. 0.66 cm diameter× 20 cm bed height columns (Omnifit) packed with MabSelect™ SuRe (GE Healthcare) Protein A media were used for system evaluation. The system was controlled using UNI- CORN software (v 5.11). Affinity resins: MabSelect™ SuRe resin (GE Healthcare, Uppsala, Sweden) was used in this project as resin of choice because it is composed of a rigid, high-flow agarose matrix and alkali-stabilized protein A-derived ligand. This ligand provides greater stability than conventional protein A-based media under the alkaline conditions used in cleaning-in-place (CIP) protocols. Cleaning can be performed with cost-effective reagents such as sodium hydroxide that may help improve process economy.

Standard Purification Procedure ("mock elution"). Protein A cycles were run using the following parameters (a) MabSelect™ SuRe resin with a load capacity of 30 g/L resin, (b) The harvested cell culture fluid (HCCF) was loaded at 15° C. (12-18° C.) (all other phases at room temp.) on a 0.66×20 cm column, (c) The pool pH was adjusted to pH 5.0 by the addition of 1.5 M Tris base. The buffers used were similar to those used for the batch process. The columns were equilibrated with 25 mM Tris and 25 mM sodium chloride, washed 0.4 M potassium phosphate, eluted with 0.1 N acetic acid (pH 2.9), and regenerated with 0.1 N sodium hydroxide for MabSelect™ SuRe (Fahrner, R. L., et al., *Biotechnol. Genet. Eng. Rev.* 2001, 18:301-327; Fahrner, R. L., et al., *Biotechnol. Appl. Biochem.* 1999, 30:121-128; B. Kelley, *Biotechnol. Prog.* 2007, 23:995-1008; Trexlar-Schmidt, M. et al., *Biopharm. Intl.* Mar. 2, 2009).

Buffers

The following buffers were used:
Elution Buffer: 0.15 M Acetic Acid, pH 2.9
Regeneration Buffer: 0.1 M NaOH, pH 13
Equilibration Buffer: 25 mM Tris, 25 mM NaCl, pH 7.1
Storage Buffer: 100 mM sodium acetate, 2% benzyl alcohol, pH 5.0

Cleaning Strategy.

The cleaning procedure is performed at 20 CV/hr flow rate. The cleaning procedure was developed based on two factors (a) pH cycling and (b) static hold times The pre-cleaning carryover results (20-30 ppm) obtained in the "mock run" without additional cleaning was well below the established safety limit of 1000 ppm, set by risk assessment. However, it was decided to err on the side of caution, as the limit for clinical manufacturing would be lower than 1000 ppm. The goal of the project was to develop cleaning procedure that can be transferred to clinical manufacturing; hence, a cleaning procedure was identified to minimize carryover to less than 1 ppm. After careful optimization the optimum cleaning strategy was based on (a) a static hold and (b) pH cycling. The addition of a static hold procedure in the cleaning process allowed for extra residence time without using extra buffer. Increased residence time likely aides with mass transfer, and effectively serves to extract any remaining protein on the column into the buffer. Alternation between an acidic and basic buffer called pH cycling, enhances protein extraction and thus effectively washes the column. The optimal cleaning conditions included those buffers that were already used as elution and regeneration buffers. The 'Elution buffer' was 0.15 M AcOH (pH 2.9) and 'Regeneration buffer' for cleaning was 0.1 N NaOH (pH 13). The choice of buffers was based on their respective properties. For example, the 'Elution buffer' (0.15 M AcOH, pH 2.9) was used to wash bound IgG from the Protein A resin. Sodium hydroxide solubilizes proteins and nucleic acids (all components of the production process) by denaturation and cleavage of the proteins into small fragments. In addition, sodium hydroxide destroys endotoxins and regenerates the resin. As neither of these conditions is incompatible with the resin, and was already used for purification of in house mAbs, their use was also economical.

Resin Selection

MabSelect™ SuRe Protein A affinity resin was chosen for the optimization as it has a large working pH range (pH 3-12), and is stable under basic conditions, without loss of binding capacity. Thus it was compatible with current Elution (0.15 M AcOH) and Regeneration (0.1 N NaOH) buffers for cleaning.

Other resins, such as ProSep® vA, were previously investigated. Briefly, several different cleaning agents were investigated to clean the ProSep® vA columns. However the majority of the conditions showed similar performance.

Screening of a variety of buffers followed by consecutive "mock runs," as outlined in the Standard Purification Procedure, resulted in decreased protein carryover from sample to sample. Increased elution flow rate also effectively cleaned the column. The major findings of this study were that static holds and pH cycling contributed more significantly to the reduction of protein carryover compared to other variables tested. Although some of the cleaning procedures did reduce protein carryover on ProSep® vA, the reduction was not sufficient to warrant its usage on pilot, or larger scale. Nevertheless, the results from the pH cycling and static hold experiments proved useful in the optimization of the cleaning procedure on MabSelect™ SuRe resin.

Analytical Methods

The antibody concentration of HCCF was determined using a 2.1×30 cm POROS column (Applied Biosystems, Foster City, Calif.) on an Agilent 1100 HPLC (Agilent Technologies, Santa Clara, Calif.). Buffer A (100 mM sodium phosphate, 250 mM sodium chloride, pH 6.3), Buffer B (2% acetic acid, 100 mM glycine), and Buffer C (0.1 M phosphoric acid, 20% CAN (20% acetonitrile)) were used, and the total run time was 4.5 min. The protein concentration in the purified pool was measured using the Agilent 8453 (Agilent Technologies, Santa Clara, Calif.) spectrophotometer at 280 nm. Multi-product enzyme-linked immunosorbent assay methods were used for CHOP, and leached ProA analysis. TaqMan polymerase chain reaction was used for CHO DNA analysis. Total protein was measured using a Capillary Zone Electrophoresis/Laser-Induced Fluorescence Detection (CZE-LIF) assay. Intact antibody and fragmented antibody parts were measured using a generic ELISA assay. SDS/PAGE was performed on 18% Tris-HCl gel.

Quantification of Protein Carryover without Cleaning

The experimental protocol for the determination of mAb carryover is as follows: First, 18 load cycles of a mAb were loaded onto a Protein A affinity column (0.66×20 cm, Volume=6.8 mL) at 30 g/L, and the sample was eluted. The Protein A affinity column was subsequently cleaned, following one of the column cleaning procedures outlined in Table 2. After cleaning, a "mock run" was performed. To determine levels of protein or impurity carryover, analytical samples were taken either during the "mock run" at specific time points or during the column wash procedure. Analytical samples collected were adjusted to pH 5-5.5 (1.5 M Tris base buffer) and then treated with a detergent (0.1% polysorbate, 0.05% sodium azide) to prevent protein surface adhesion (as this would give a false negative result).

In a first experiment the carryover in the elution pool was first determined for three different mAbs (mAbA, mAbB, and mAbC) purified sequentially on a MabSelect™ SuRe Protein A column without intermittent cleaning. The three purification cycles were loaded at 30 g/L on a Protein A affinity column (0.66×20 cm, Volume=6.8 mL), and the results are shown in (FIG. 1). The data are graphed as the amount of intact IgG protein (ng carryover/mg product) carried over from the previous run as a function of elution. According to the graph without intermittent cleaning the highest carryover of the three load cycles was 30-40 ppm (FIG. 1). The results clearly showed that in order to stay below 1 ppm of protein carryover, additional cleaning cycles are needed to recycle the column.

Optimization of the MabSelect™ SuRe Cleaning Procedure (CP)

Figure 2:
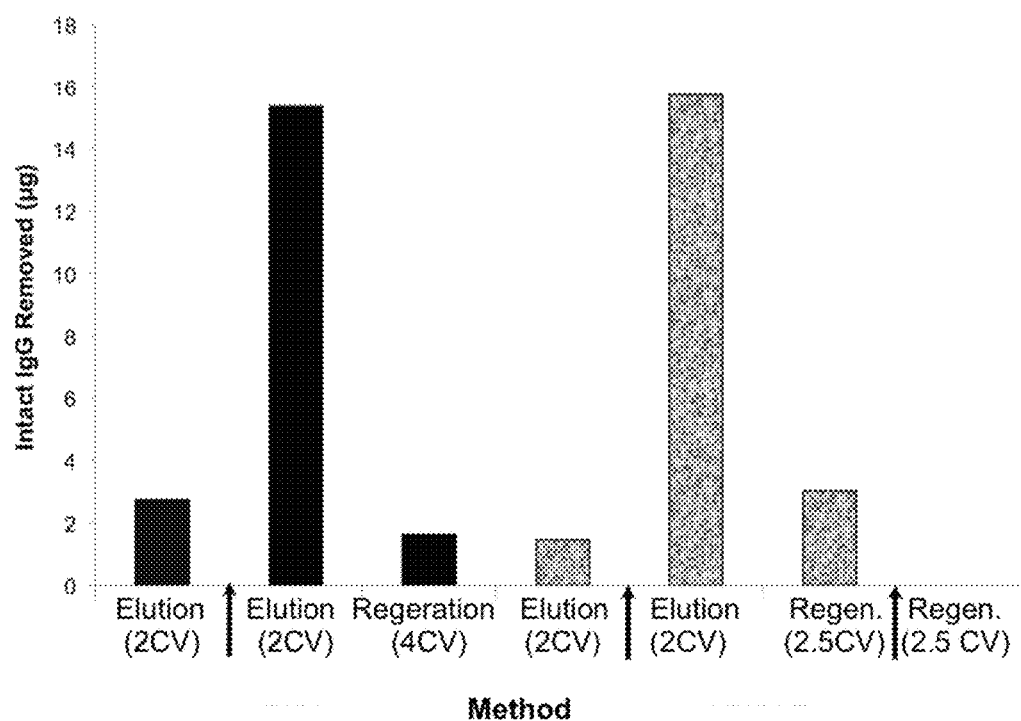
FIG. 2 shows protein removal seen in initial cleaning cycles as a function of elution buffer (0.15 M Acetic acid) or Regeneration buffer (0.1 N NaOH) CV washing. Arrows point to 30 min static holds. Note there is a 5 fold increase in the amount of protein that is washed off the column after a 30 min static hold and no protein was detected after static hold with Regeneration buffer. Legend: Method 4 (Table 2): black; method 5 (Table 2): black and grey.

In an attempt to simplify cleaning procedures by reducing buffer consumption and cleaning times, different combinations of buffers and run times were investigated (Table 2, Entries 1-3). As the levels of carryover never fell below the limit of 1 ppm, it was clear that more rigorous cleaning procedures needed to be identified for lab-scale recycling on the MabSelect™ SuRe columns More rigorous cleaning conditions included the addition of static holds, where the column was held for a defined period of time in a buffer and run at zero flow (Table 2, Entry 4-5). It was found that static holds effectively washed more protein off the resin than flushing with a buffer. Static holds effectively increased the amount of intact IgG washed off the column 5-fold after an elution buffer static hold, and intact IgG was not detected after a Regeneration buffer static hold (FIG. 2). Further, the amount of carryover was significantly reduced in a "mock elution" to less than 10 ppm of intact IgG for Entry 4 (Table 2) and less than 1 ppm of intact IgG is carried over for Entry 5 (Table 2).

TABLE 2

Cleaning procedures investigated to reuse a MabSelect ™ SuRe column[a].

| Entry | Condition | Intact IgG carryover (ng carryover/mg product)[f] |
|---|---|---|
| 1 | Regeneration buffer[b] (6 CV) <br> Equilibration buffer[c] (5 CV) | 0.98 ppm |
| 2 | Regeneration buffer[b] (5 CV) <br> Elution buffer[d] (3 CV) <br> Regeneration buffer[b] (5 CV) <br> Equilibration buffer[c] (5 CV) | 1.80 ppm |
| 3 | Elution buffer[d] (3 CV) <br> Regeneration buffer[b] (5 CV) | <1 ppm |
| 4 | Elution buffer[d] (2 CV) <br> 30-minute static hold <br> Elution buffer[d] (2 CV) <br> Regeneration buffer[b] (4 CV) | <10 ppm |
| 5 | Elution buffer[d] (2 CV) 30-minute static hold[e] <br> Elution buffer[d] (2 CV) <br> Regeneration buffer[b] (2.5 CV) <br> 30-minute static hold[e] <br> Regeneration buffer[b] (2.5 CV) | <1 ppm |
| 6 | Equilibration buffer[c] (2 CV) <br> 30-minute static hold <br> Equilibration buffer[c] (2 CV) <br> Elution buffer[d] (2 CV, pH 2.8) <br> 30-minute static hold <br> Elution buffer[d] (2 CV) <br> Regeneration buffer[b] (2 CV) <br> 30-minute static hold <br> Regeneration buffer[b] (2 CV) | <3 ppm |
| 7 | Equilibration buffer[c] (4 CV) <br> 6 cycles of the following: <br> Elution buffer[d] (3 CV) <br> 10-minute static hold <br> Elution buffer[d] (1 CV) <br> Regeneration buffer[b] (3 CV) <br> 10-minute static hold <br> Regeneration buffer[b] (1 CV) | <0.3 ppm |
| 8 | 6 cycles of the following: <br> Elution buffer[d] (3 CV) <br> 15-minute static hold <br> Elution buffer[d] (1 CV) <br> Regeneration buffer[b] (3 CV) <br> 15-minute static hold <br> Regeneration buffer[b] (1 CV) <br> Storage buffer[g] (3 CV) <br> 15-minute static hold <br> Storage buffer[b] (1 CV) | <0.5 ppm |

CV = column volume.
[a]0.66 × 20 cm.
[b]Regeneration Buffer = 0.1N NaOH (pH 13).
[c]Equilibration buffer = 25 mM Tris, 25 mM NaCl (pH 7.1).
[d]Elution buffer = 0.15M Acetic acid (pH 2.9).
[e]static hold = holding the buffer in the column at 0 mL/min flow rate.
[f]Carryover determined in a "mock run."
[g]Storage buffer = 100 mM sodium acetate and 2% Benzyl alcohol (pH 5).

Figure 3:
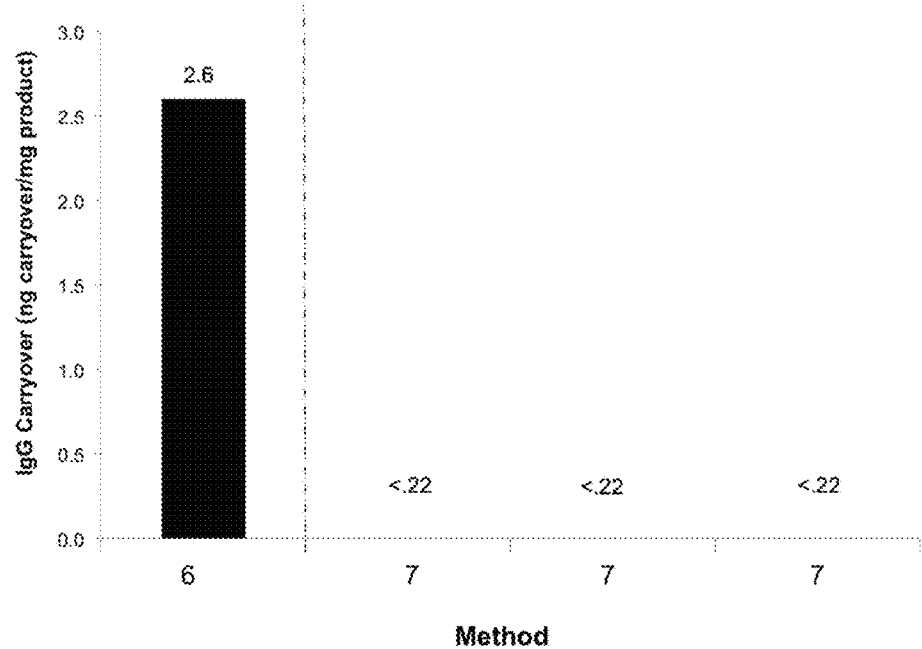
FIG. 3 shows intact IgG protein detected after "mock runs" were performed on a MabSelect™ SuRe column after cleaning using Method 6 (black bar, Table 2) and Method 7 (none detected, Table 2). Three "mock runs" were performed using Method 7 (Table 2) and results were reproducible.
Figure 4:
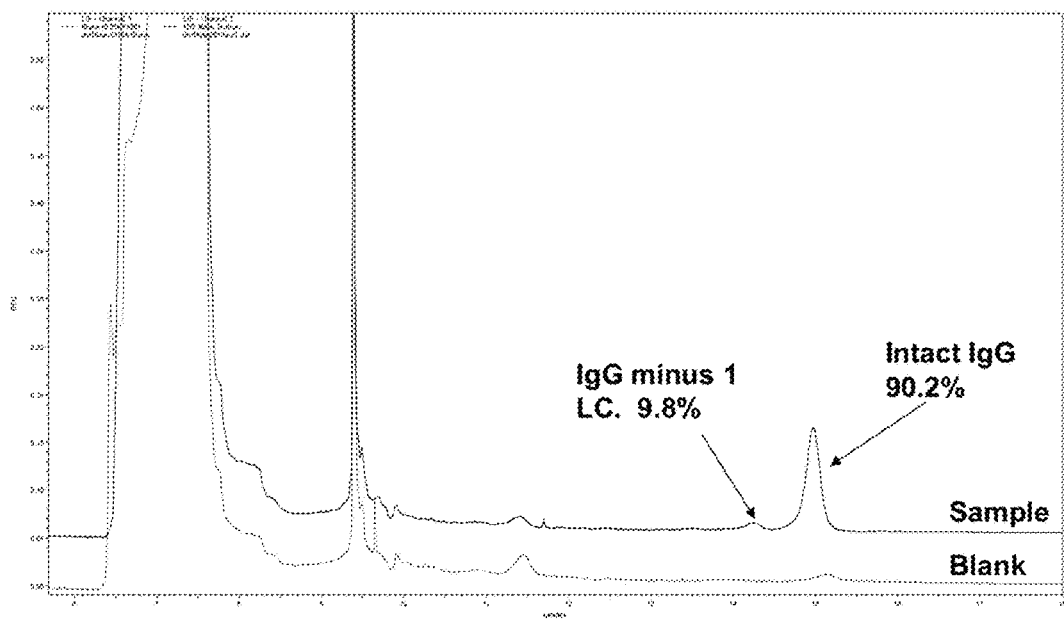
FIG. 4 shows Capillary Electrophoresis-Sodium Dodecyl Sulfate (CE-SDS) analysis of a "mock elution" after cleaning of a MabSelect™ SuRe column following the Method 7 cleaning procedure (Table 2) for a 94 ng/mL mock elution sample revealed that the mAb was over 90% fully intact.

Increasing the number of cleanings with static hold time investigated with Entries 6-7 (Table 2). Clearly, static hold times with additional cleaning cycles more effectively cleaned the resin than all other previously investigated conditions. Such that after "mock runs" were carried out, less than 3 ppm of carryover for Entry 6 (Table 2) and less than 0.3 ppm of carryover for Entry 7 (Table 2) were detected (Table 2, FIG. 3). The increase in pH cycles eluted more protein during the sharp pH transitions. However, aggregate time with 0.1N NaOH is increased by increasing number of cycles with long static hold which could be detrimental to the resin binding capacity. Since the majority of protein is eluted after first cycle (FIG. 3) for both 30-minute and 10-minute static hold times, the extra static hold time had limited additional benefit. Hence, shorter static hold times with increased cycles was preferred over longer hold times. In addition to ELISA assays, capillary electrophoresis-Sodium Dodecyl Sulfate analysis (CE-SDS) was performed to ensure fragment clearance through the cleaning cycles. CE-SDS analysis of a "mock elution" after cleaning of a MabSelect™ SuRe column using the procedure outlined in Entry 7 (Table 2) for a 94 ng/mL "mock elution" sample revealed that the isolated mAb was over 90% fully intact (FIG. 4).

Figure 5:
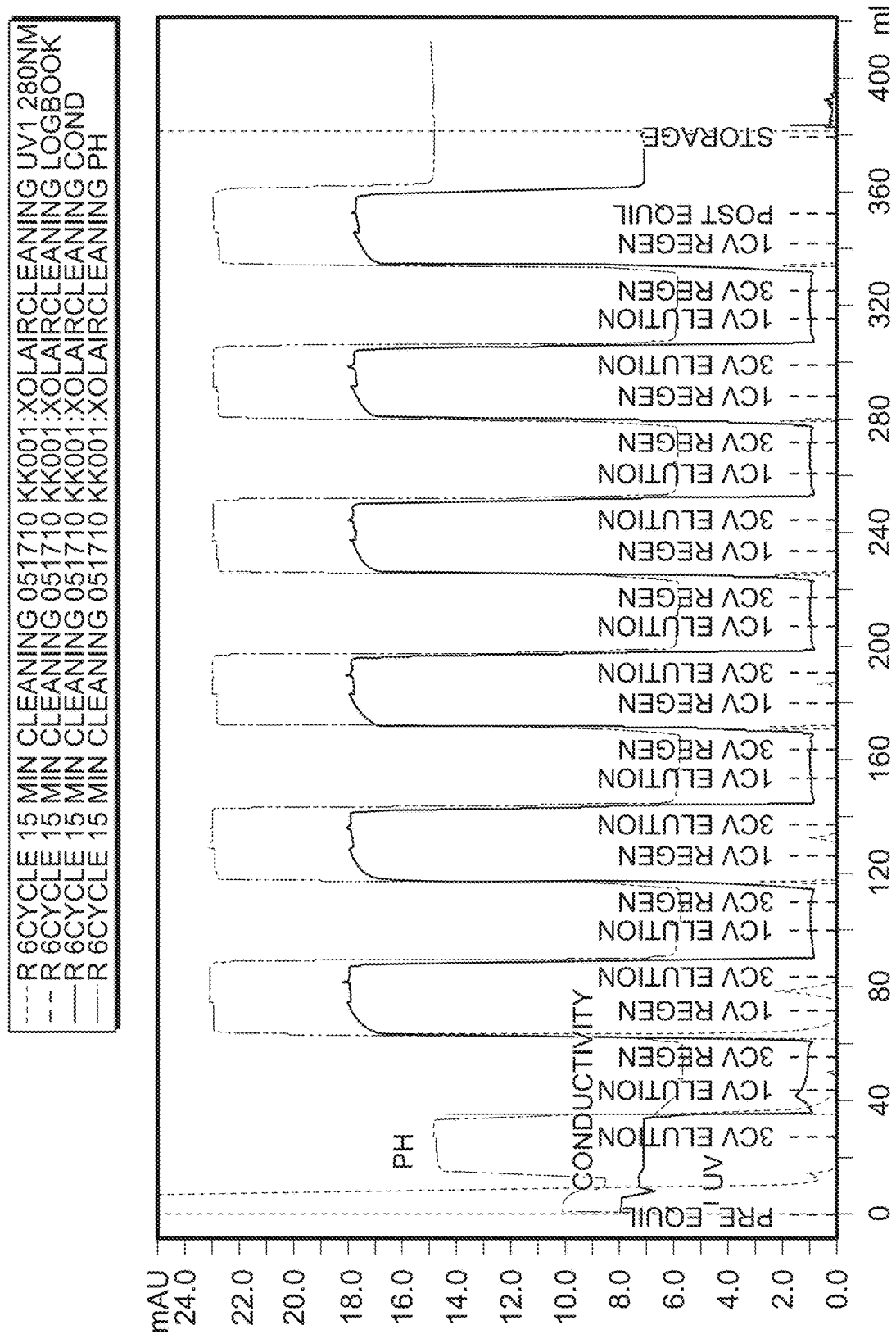
FIG. 5 shows Akta chromatograms using the Method 7 cleaning procedure (Table 2) a chromatogram of a "mock elution" suggests efficient cleaning of the column, as demonstrated with spikes in the UV-intensity when a shift from Elution buffer (0.15 M acetic acid) to Regeneration buffer (0.1 N NaOH) is made for each of the 6 cycles. Blue line=UV 280 nm, Red line=pH, Magenta line=conductivity.

As a "proof of concept" using the cleaning procedure in Entry 7 (Table 2) an Akta chromatogram (generated during purification run) of a "mock elution" suggested efficient cleaning of the column was achieved when a shift from Elution buffer (0.15 M acetic acid) to Regeneration buffer (0.1 N NaOH) was made. This was evidenced by successive spikes in the UV-intensity during this pH cycling for each of the 6 cycles (FIG. 5). Taken together, the pH cycling and static holds provide an ideal cleaning procedures.

Figure 6A:
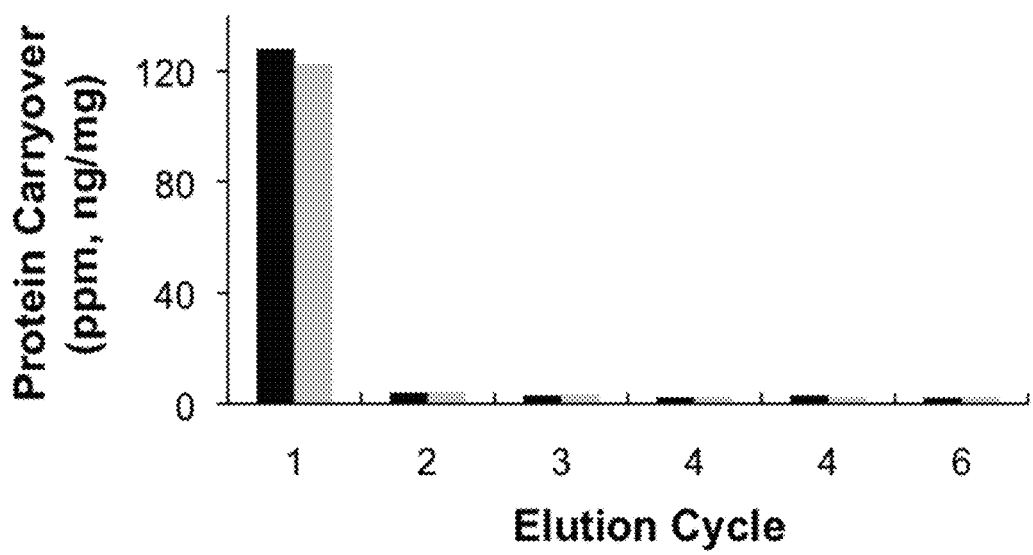
FIGS. 6A-6C shows results for a lab scale purification of mAbA using the optimized cleaning procedure (Entry 7, Table 2) before "mock runs" to determine protein carryover.
Figure 6B:
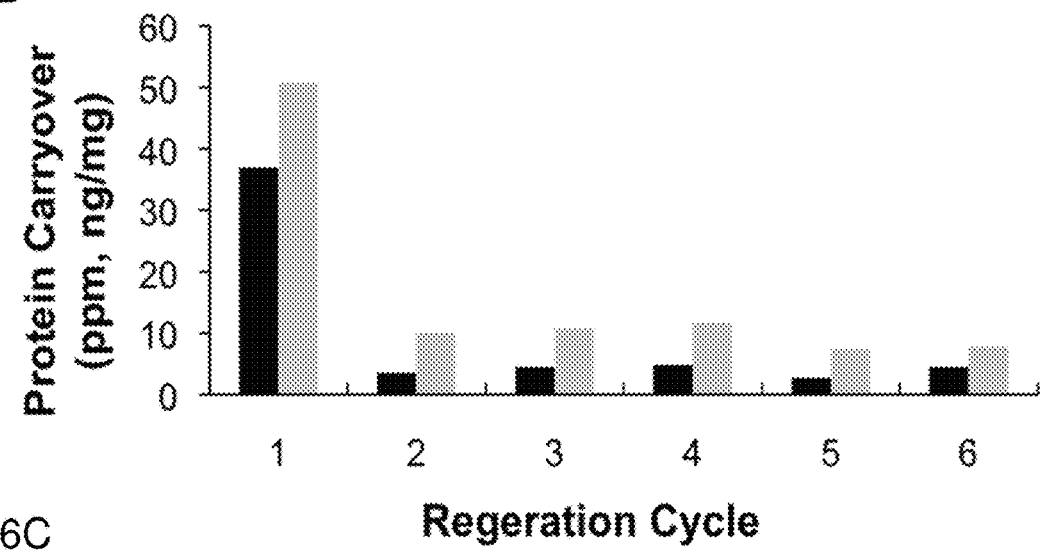
Figure 6C:
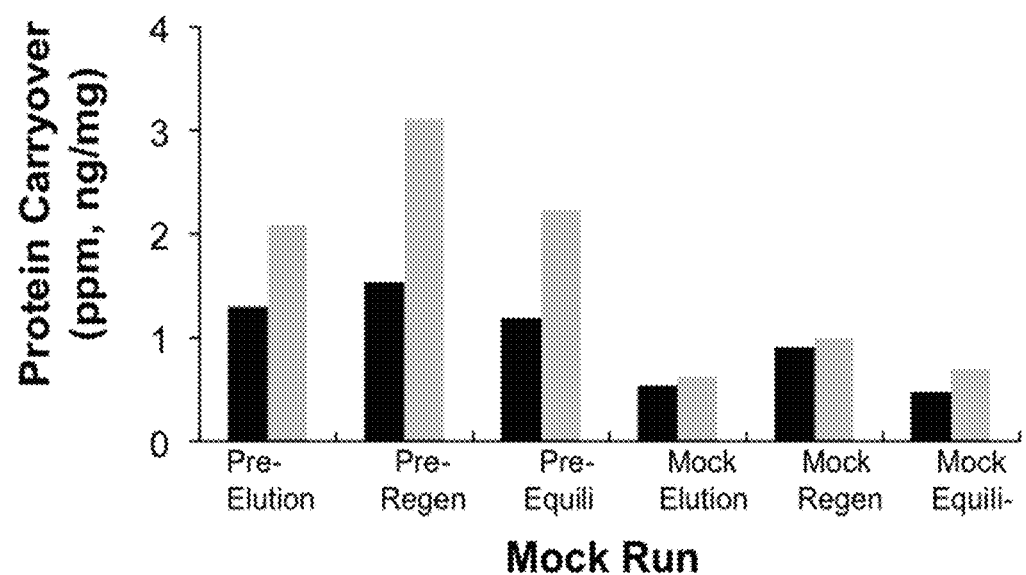

Scaling of the optimized cleaning procedure (Entry 7, Table 2) on lab scale for the purification of mAbA on a MabSelect™ SuRe Omni fit column (0.66×20 cm, Volume=6.7 mL, 18 cycles of HCCF at 30 g/L) did in fact minimize protein carryover (FIG. 6). The results clearly demonstrate that after cleaning the column using the six cycles of Elution buffer (0.15 M Acetic acid), significantly less intact IgG or Fc fragment was detected after each cycle, such that by cycle 6 less than 5 ppm was detected (FIG. 6). Similarly, even less intact IgG and Fc fragments (<10 ppm) were detected after each of the six cycle washes with Regeneration buffer (0.1 M NaOH, FIG. 6). Further, by the time the "mock elution" was carried out (after pre-elution, pre-regeneration, and pre-equilibration) less than 1 ppm of protein carryover was detected in the "mock elution" sample (FIG. 6).

Figure 7:
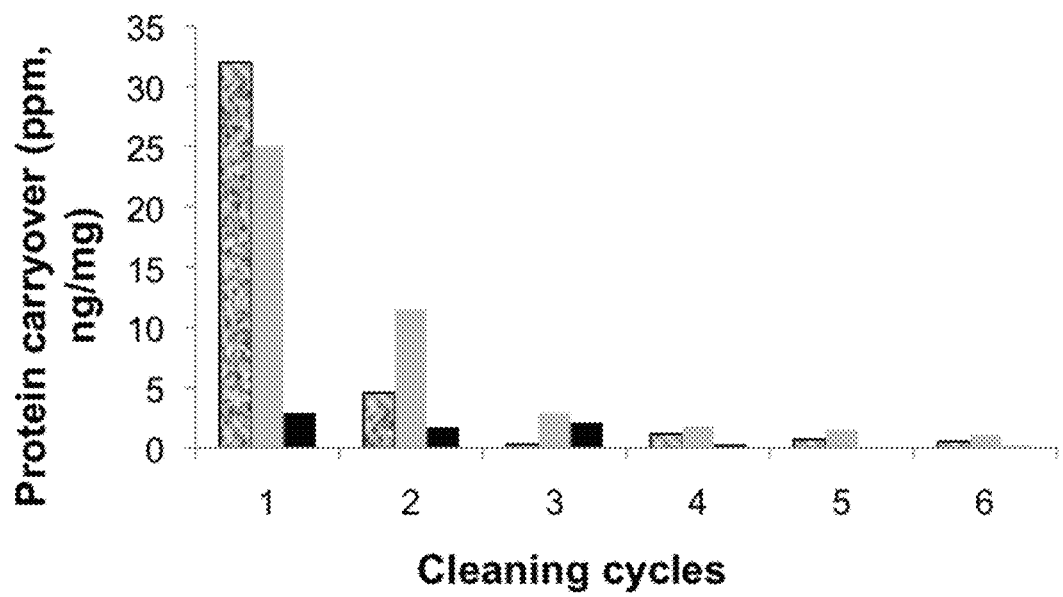
FIG. 7 shows a plot of total protein carryover as a function of cleaning cycle following conditions outlined in Method 8, Table 2 with Storage buffer (100 mM sodium acetate and 2% Benzyl alcohol (pH 5)). Legend: Elution cycles (black & grey), Regeneration cycles (grey), Storage buffer cycles (black).

During the course of the cleaning procedure optimization, small amounts of protein came off the column after periods of storage in storage buffer (100 mM Sodium Acetate, 2% benzyl alcohol at pH 5.0). This observation suggested that perhaps the storage buffer could also serve as an efficient cleaning buffer for the MabSelect™ SuRe resin. However, subsequent "mock runs" after intermittent column cleaning with the storage buffer did not result in more efficient column cleaning than previously optimized conditions (Entry 8, Table 2; FIG. 7). Further, the addition of this cleaning buffer in the process would make the overall process longer, without additional benefit. Hence, it was decided to proceed with the existing optimized cleaning procedure.

Figure 8:
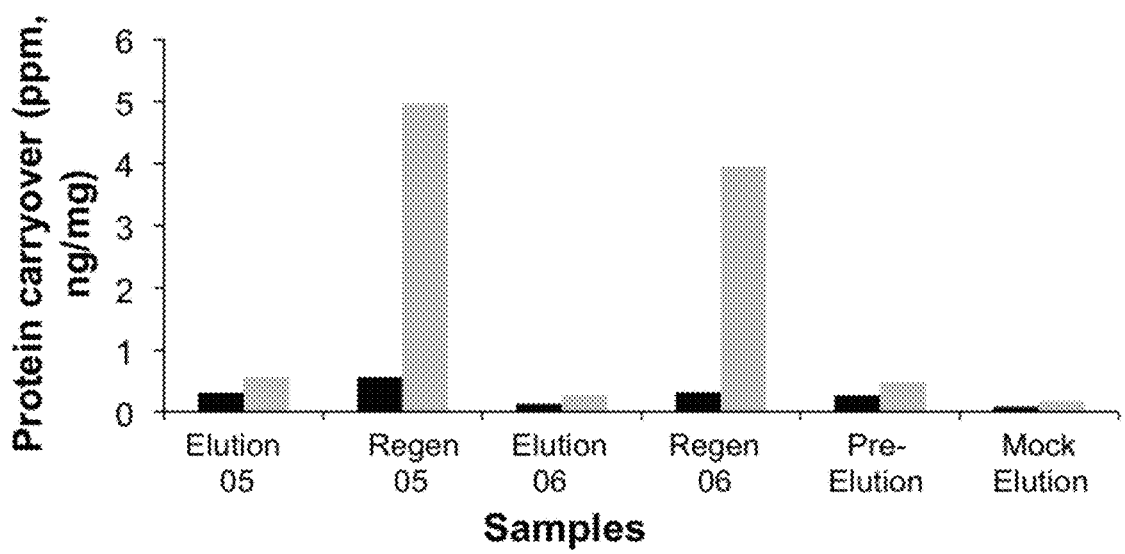
FIG. 8 is a plot of protein carryover as a function of sample from a 3.23 L pilot scale purification of mAbZ on MabSelect™ SuRe column followed by column cleaning with optimized 6 cycle cleaning procedure (Entry 7, Table 2). Intact IgG is shown in black, Fc fragments are shown in grey.

The optimized cleaning procedure (Entry 7, Table 2) was then implemented on a pilot scale for the purification of mAbZ (14×20, Volume=3.23 L) as a final test prior to extending the procedure onto mAbs of interest. The results were promising as expected with decreasing intact IgG and Fc detected after each cleaning such that less than 1 ppm protein carryover was detected in the "mock elution" of a "mock run." This particular pilot run was performed with mAbZ on a MabSelect™ SuRe column that had previously been used in nine purification cycles (FIG. 8).

As this cleaning procedure was so effective a total of 5 pilot scale columns were cleaned after implementation. Further analysis of all these pilot scale samples to determine the amount of other impurities such as: leached Protein A (Leached Protein A assay), (Zhu-Shimoni, J., et al., *J Immunol. Methods*. 2009, 341:59-67) other proteins (CZE LIF-Total protein, assay; D. Michels, (in preparation). Chinese Hamster Ovary Proteins (CHOP assay; Fahrner, R. L. et al., *Biotechnol. Appl. Biochem.* 1999, 30:121-128) and DNA (CHO DNA assay; a TaqMan polymerase chain reaction used for CHO DNA analysis), Fc fragments of an antibody (Human Fc ELISA; intact antibody and fragmented antibody parts were measured using a generic in house developed sandwich ELISAs) and total antibody (Intact Human IgG ELISA; intact antibody and fragmented antibody parts were measured using a generic in house developed sandwich ELISAs) were also performed to verify that the process performed similarly at pilot scale (Table 3). As expected, all detected impurities were well below acceptable limits, and the cleaning procedure can be used for purification of mAbs (Entry 6, Table 3).

TABLE 3

Analysis of all samples from pilot scale purification of mAbZ using optimized cleaning.

| Entry | Sample | Leached Protein A (ppm) | CZE-LIF (µg/mL) | CHOP DNA (ppm) | CHO DNA (pg/mL) |
| --- | --- | --- | --- | --- | --- |
| 1 | Elution 05 | 2.817 | <0.25 | 0.51 | <1.00 |
| 2 | Elution 06 | 3.06 | <0.25 | <0.5 | <1.00 |
| 3 | Regeneration 05 | 17.7 | >2.5 | <0.5 | <1.00 |
| 4 | Regeneration 06 | 17.6 | >2.5 | <0.5 | 67.93 |
| 5 | Pre-Elution | <1 | >2.5 | <0.5 | <1.0 |
| 6 | Mock Elution | <1 | <0.25 | 0.74 | <1.0 |

Results

The previously optimized extended cleaning condition (Entry 7, Table 2) was modified slightly for future studies and incorporated a 15 minute static hold time, instead of a 10 minute one (FIG. 8). The overall process of cleaning the resin took 4.5 hours at 20 column volume (CV)/hour flow rate, and it was run for 6 cycles (6 times). These conditions included pH cycling, between the Elution and Regeneration buffer, and static holds to effectively wash the column. Briefly, the procedure is detailed in FIG. 9. The entire process is run a total of 6 cycles in order to thoroughly clean the resin. Finally, the resin was washed with Equilibration buffer (3CV) before storage in storage buffer (SCV, Storage buffer). In order to effectively monitor resin-cleaning, samples were collected after the 15-minute hold times to analyze carryover at each cycle and determine how much protein was removed from the resin at each step and each cycle (FIG. 9).

Figure 9A:
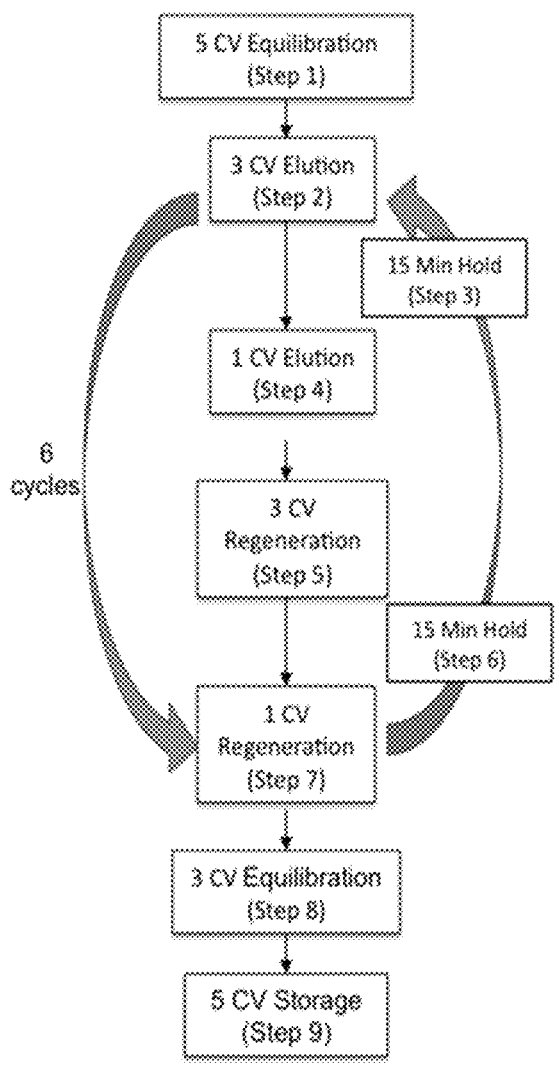
FIGS. 9A and 9B shows a schematic outline of the optimized cleaning protocol using 15-minute static hold time (FIG. 9A) and a "mock run" (FIG. 9B). The Equilibration buffer is 25 mM Tris, 25 mM NaCl (pH 7.1). The Elution buffer is 0.15 M sodium acetate (pH 2.9). The Regeneration buffer is 0.1 N NaOH (pH 13).
Figure 9B:
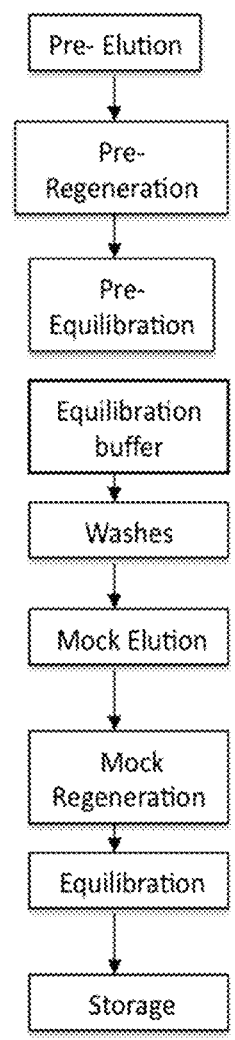

After the resin was cleaned, a "mock run" was performed to verify the protein carryover (FIG. 9). The "mock elution" was collected and assayed to determine the amount of carryover and the presence of other impurities (Zhu-Shimoni, J., et al., *J Immunol. Methods.* 2009, 341:59-67; Fahrner, R. L., et al., *Biotechnol. Appl. Biochem.* 1999, 30:121-128). Total protein was measured using a Capillary Zone Electrophoresis/Laser-Induced Fluorescence Detection (CZE-LIF) assay (D. Michaels et al., in preparation). A TaqMan polymerase chain reaction was used for CHO DNA analysis. Intact antibody and fragmented antibody parts were measured using generic sandwich ELISAs. These other impurities include host cell components, proteins, viruses, or DNA. These assays include a test for intact human immunoglobulin (IgG) using an ELISA, human Fc fragment in another ELISA, any other protein using a Capillary Zone Electrophoresis/Laser-Induced Fluorescence Detection assay (CZE/LIF), Chinese Hamster Ovary Proteins in a CHOP assay (Fahrner, R. L., et al., *Biotechnol. Appl. Biochem.* 1999, 30:121-128), and leached Protein A assay (Zhu-Shimoni, J., et al., *J Immunol. Methods.* 2009, 341: 59-67). In the "Intact Human IgG ELISA" and the "human Fc ELISA", the amount of entire antibody or antibody fragment on the column is quantified; where the former binds to both the fragment antigen-binding region (Fab) and the Fragment crystallizable (Fc) regions, and the latter binds only to human Fc region. The CZE-LIF assay can confirm those results by quantifying the total amount of protein in a sample. Finally, it is known that Protein A can leach off the resin during runs or during harsh cleaning, negatively impacting binding capacity, thus it is important to determine the amount of leached Protein A (Fahrner, R. L., et al., *Biotechnol. Appl. Biochem.* 1999, 30:121-128; Kelley, B., *Biotechnol. Prog.* 2007, 23995-1008; D. Michaels, in preparation; Fahrner, R. L., et al., *Biotechnol. Genet. Eng. Rev.* 2001, 18:301-327).

Figure 10A:
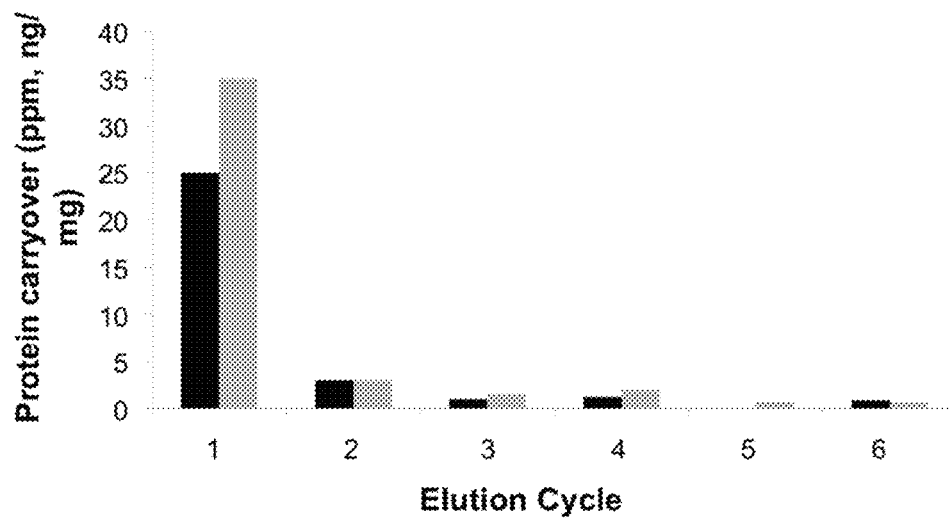
FIGS. 10A-10C shows the results for a lab scale purification of mAbC using the cleaning procedure (FIGS. 9A and 9B) before "mock run" to determine protein carryover.
Figure 10B:
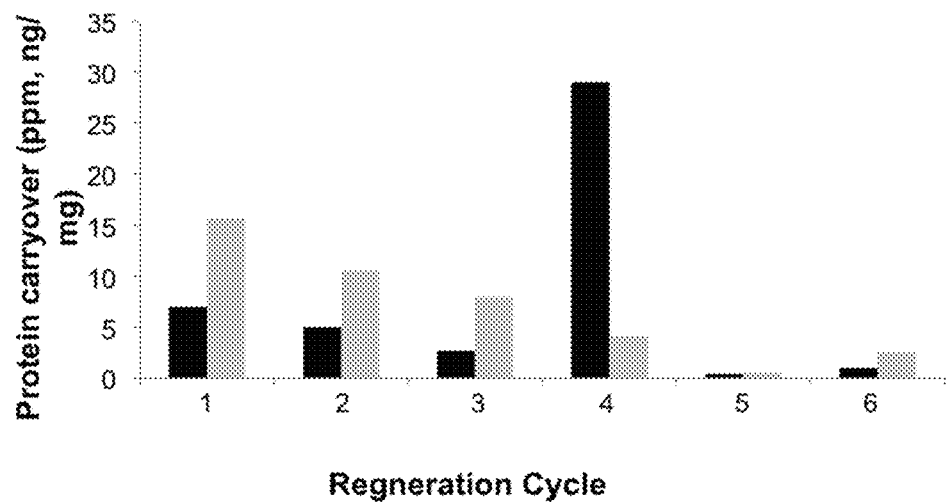
Figure 10C:
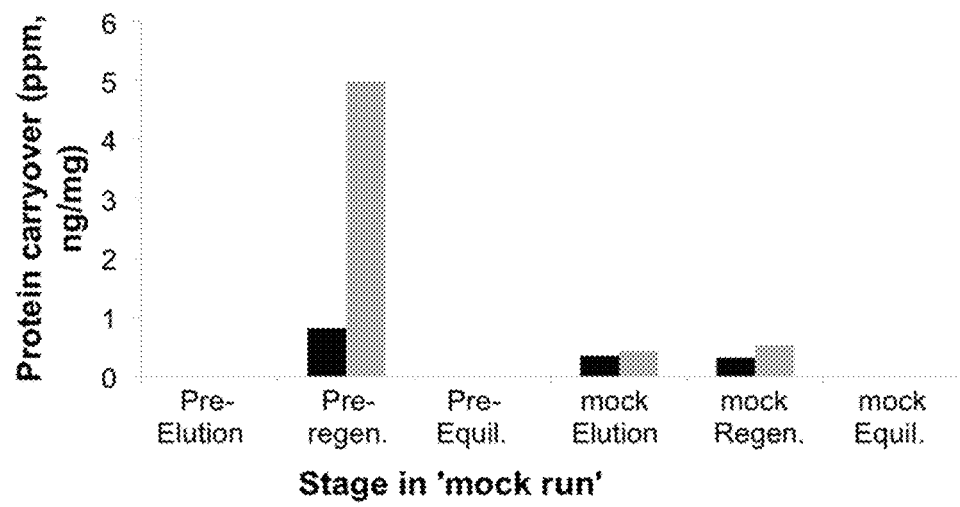

To test the efficiency of the cleaning procedure a mAb of interest, mAbC was purified on lab scale on the MabSelect™ SuRe column (0.66×20 cm, Volume=6.8 mL) with an AKTA Explorer 100 (as described in 2.2). The protein carryover during and after several cleaning cycles was measured and the results demonstrated that protein carryover decreased after each cleaning cycle (FIG. 10). The intact IgG protein and Fc fragment carryover of mAbC in a subsequent "mock run" decreased from 25 ng/mg intact IgG and 35 ng/mg Fc fragments in the first cycle with Elution buffer to less than 5 ng/mg for both after the sixth cycle with Elution buffer (FIG. 10). During and after Regeneration (which followed Elution), significantly more intact IgG and Fc fragments washed off the column until the sixth cycle was reached where levels were reduced cumulatively to less than 5 ng/mg carryover. To test carryover a "mock run" (run after the entire cleaning cycle) was performed and additional IgG and Fc fragments washed off the column in the pre-regeneration, but by the time the "mock elution" process began (where a second mAb would be expected to come off in the reuse process) less than 1 ppm of IgG and Fc fragments were detected (FIG. 10). Taken together these results confirm that these conditions are effective cleaning conditions and the total amount of protein carried over from previous runs will be less than 1 ppm when reusing the resin, after using this cleaning procedure.

Figure 11:
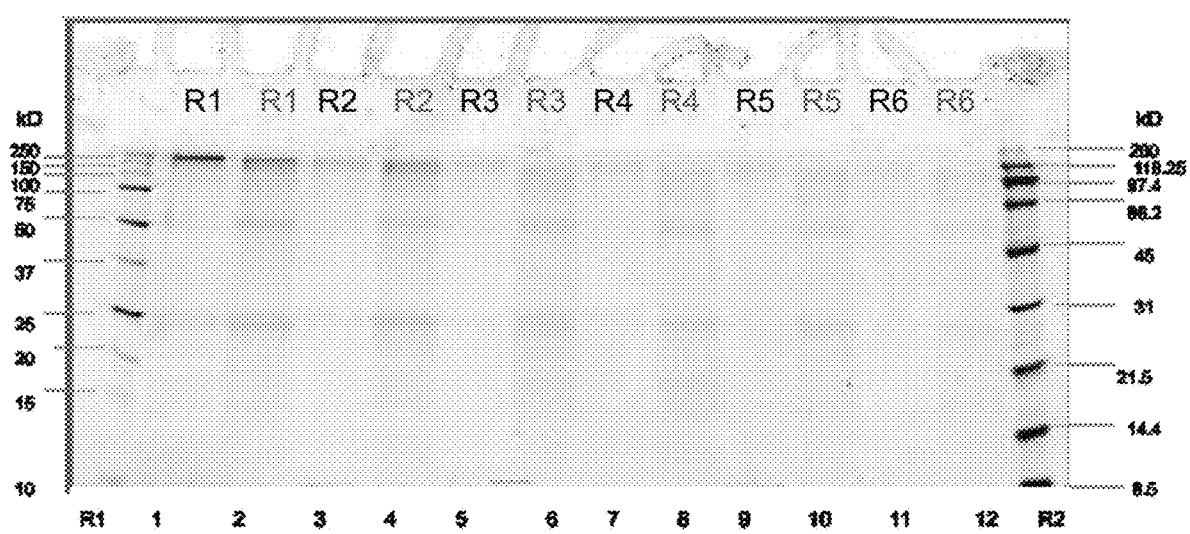
FIG. 11 shows a 10% Tris-HCl gel taken at different stages of an optimized cleaning protocol of a MabSelect™ SuRe column (FIGS. 9A and 9B). Samples were taken after the purification of mAbC. Regeneration samples are concentrated (25 fold) and lanes 2, 4, 6, 8, 10 and 12 contain samples after the 15 min static holds.

In order to get a better idea of what type of protein fragments are present per cycle wash, a sample from each cycle was run on a 10% Tris-HCl gel (mAbC) (FIG. 11) (Trexlar-Schmidt, M., et al., Biopharm. Intl. Mar. 2, 2009). From cycle 1 to cycle 6 less protein was observed in each successive cycle (decreased band intensity in each lane, FIG. 11). Further, lanes with samples from the static hold cycles were more concentrated than during cycle 1-6, with more protein removed after each static hold cycle. These results demonstrate that extended residence times help remove residual protein off the column.

Figure 12A:
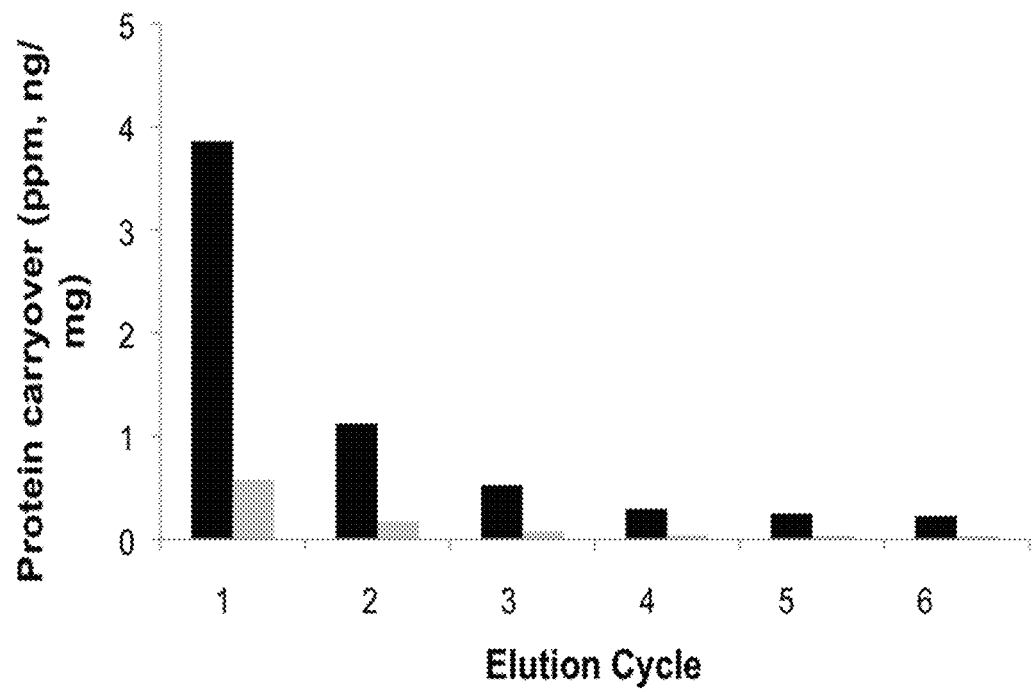
FIGS. 12A and 12B shows the results for a pilot scale column (3 L) purification of mAbC using the optimized cleaning procedure (Entry 7, Table 2) before "mock run" to determine protein carryover.
Figure 12B:
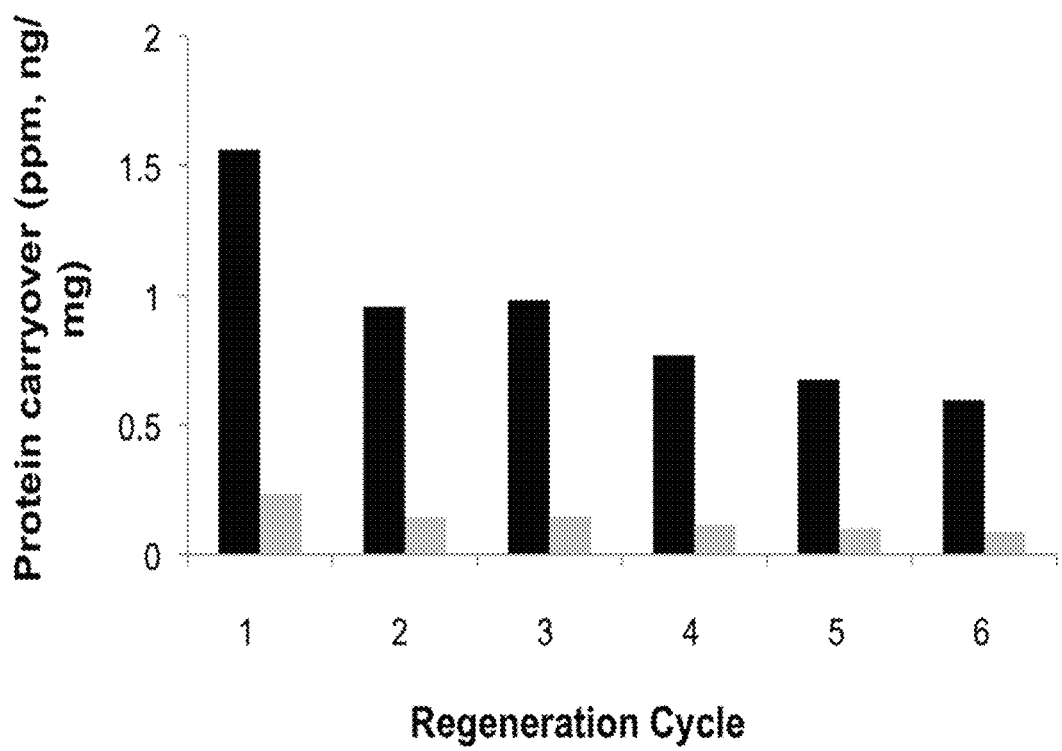

This optimized cleaning process was extended to the purification of mAbX at pilot scale on a MabSelect™ SuRe column (13.8×20, Volume=3 L). The results were similar to the results previously seen at lab scale (FIG. 6). As seen on the lab scale runs, protein impurities are removed from the resin in the initial cleaning stages, and their overall concentration decreases after each elution and regeneration cycle, until the sixth cycle is reached (FIG. 12). During the resin regeneration the amount of protein that is initially washed off the column is much greater than after the sixth cycle, such that by the time the sixth regeneration cycle is reached, less than 1 ppm of protein impurities are detected (FIG. 12).

Purification of mAbY on a MabSelect™ SuRe column (20×20, Volume=6.28 L) and subsequent column cleaning with the cleaning protocol described above (FIG. 9), followed by a "mock run" resulted in less than 1 ppm of leached Protein A, less than 0.25 mg/mL (limit of quantification) CZE-LIF, less than 0.5 ppm CHOP, and less that 1.0 pg/mL CHO DNA after the sixth regeneration cycle in the mock elution (Table 4). All impurities were comparable to historical data, and within acceptable limits.

TABLE 4

Analysis of all samples from large-scale column (6.28 L) purification of mAbY on a MabSelect ™ SuRe column using the optimized cleaning procedure MSSCCP to verify minimal carryover.[a]

| Entry | Sample | Leached Protein A (ppm) | CZE-LIF (µg/mL) | CHOP (ppm) | CHO DNA (pg/mL) |
|---|---|---|---|---|---|
| 1 | Elution 02 | 6.24 | 0.35 | 0.74 | <1.00 |
| 2 | Elution 03 | 2.72 | 0.28 | 0.63 | <1.00 |
| 3 | Elution 04 | 3.08 | 0.35 | <0.5 | <1.00 |
| 4 | Elution 05 | 3.01 | 0.34 | <0.5 | <1.00 |
| 5 | Elution 06 | 3.03 | <0.25 | <0.5 | <1.00 |
| 6 | Regeneration 06 | 23.72 | >2.5 | 1.1 | 27.05 |
| 7 | Pre-Elution | 1.4 | <0.25 | <0.5 | 1.12 |
| 8 | Mock Elution | <1 | <0.25 | <0.5 | <1.0 |

In a final test of the robustness of the optimized cleaning protocol (FIG. 9), a 6.28 L MabSelect™ SuRe resin that had previously undergone 153 multiproduct load cycles was used to purify a mAb of interest. The carryover from the previously used resin into a "mock run" (Entry 1, Table 5) was compared to the carryover observed from three other different MabSelect™ SuRe resins. The results are outlined in Table 5. Briefly, the old MabSelect™ SuRe large-scale multiproduct resin (Entry 1, and 2, Table 5), behaved comparably to a new mAb specific (not a multiproduct) MabSelect™ SuRe resin (Entry 3, Table 5) and a new mAb specific lab scale MabSelect™ SuRe resin (Entry 4, Table 5). According to the results all the Protein A resins provided mAbs in greater than 90% yield, with comparable CHOP, percentage aggregate and leached Protein A (ng/mg). Taken together a multiproduct resin has no negative impact on product impurity profile or the step yield. Pilot scale and lab scale results are also comparable (Entry 4, Table 5).

In addition to the work presented, several more mAbs have been purified on multiproduct resins that were cleaned using the procedure. The results have all been very similar and reproducible with total protein levels below 0.25 ppm (assay detection limit) (Table 6). The results suggest the optimized cleaning procedure is an efficient, reproducible and robust way to clean, regenerate, reuse and recycle multiproduct MabSelect™ SuRe Protein A resins. Use of the MSSCCP cleaning procedure for intermittent Protein A resin cleaning reduces protein carryover to well below established safety margins.

TABLE 5

Comparison of mAb product yields and impurity profiles of different MabSelect™ SuRe columns after using the optimized cleaning procedure[a].

| Entry | Column/ Scale | Step Op. | Yield (%) | Leached Protein A (ppm) | % ag.[f] | CHOP (ppm) | CHO DNA (pg/mL) |
|---|---|---|---|---|---|---|---|
| 1 | A/400 L[b] | HCCF | — | — | — | 1,161,000 | 59,700 |
|   |   | Protein A | >90 | 8 | 3.17 | <12000 | 62 |
| 2 | B/100 L[c] | HCCF | — | — | — | 2,115,520 | — |
|   |   | Protein A | >90 | 12 | 2.6 | <12000 | 80 |
| 3 | C/400 L[d] | HCCF | — | — | 2.2 | 1,115,320 | — |
|   |   | Protein A | >90 | 10 | 1.6 | <12000 | — |
| 4 | D[g] | Protein A | >95 | 15 | N/A | <12000 | 960 |

[a]For information on a particular assay see the Supporting Information.
[b]Column A was an old MabSelect™ SuRe multiproduct column used previously in 153 load cycles.
[c]Column B was a lab scale run on a newer MabSelect™ SuRe column.
[d]Column C was a pilot scale purification on a MabSelect™ SuRe mAb-specific (not multiproduct) column.
[e]Exchg. = Exchange.
[f]ag. = aggregate.
[g]Column D was a newer lab scale mAb specific MabSelect™ SuRe column.

A highly effective MabSelect™ SuRe cleaning method has been developed that allows MabSelect™ SuRe Protein A resin to be used for multi-product purification with no impact on product purity and or loss of resin binding capacity. Data from lab as well as pilot scale experiments suggest that a cleaning protocol that includes 6 cycles of 0.15 M Acetic Acid (Elution buffer) and 0.1 N Sodium Hydroxide (Regeneration buffer) washes and 15 min hold times clean the MabSelect™ SuRe resin to less than 5 ppm of protein carryover in this first mAb cleaning step. The process was successfully implemented on a multi-product Protein A resin (MabSelect™ SuRe) on pilot scale, giving further credence of the usefulness of the strategy.

TABLE 6

Analysis of in-house mAbs that have been purified on Protein A resin that was cleaned using the optimized cleaning procedure on a multiproduct column

| mAb | scale | CVb (mL) | Total Protein (mg/mL) |
|---|---|---|---|
| 1 | Lab | 6.8 | <0.25 |
| 2 | Lab | 6.8 | 0.46 |
| 3 | Pilot | 3000 | <0.25 |
| 4 | Pilot | 6280 | <0.25 |
| 5 | Pilot | 6280 | <0.25 |
| 6 | Pilot | 3230 | <0.25 |
| 7 | Pilot | 6280 | <0.25 |
| 8 | Pilot | 1730 | <0.25 |

Example 2. Evaluation of Ion Exchange Columns for Multi-Product Use

Figure 13:
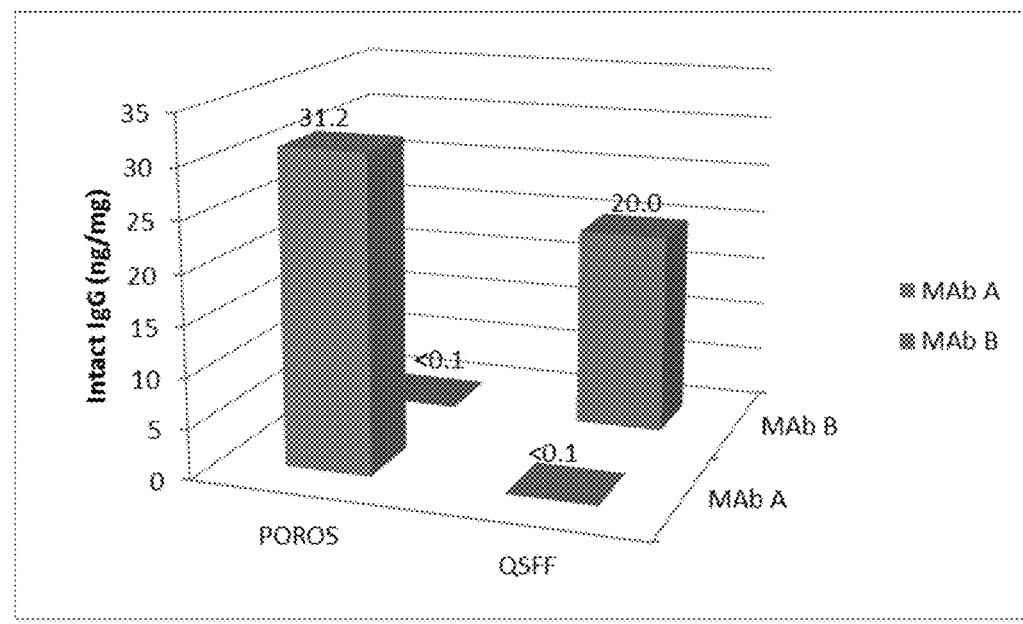
FIG. 13 shows the results intact IgG carryover detected following mock elutions of a cation exchange column (POROS) and an anion exchange column (QSFF). MAbA or MAbB had previously been loaded and eluted from the columns.

Studies were performed to determine if a similar cleaning process could be developed for ion exchange chromatographies. MAbA and MAbB from ProA pools were loaded onto cation exchange columns (POROS) or anion exchange columns (QSFF). Following normal elution, the columns were then subject to a "mock elution". Fractions were analyzed for the presence of MAbA and/or MabB using a MabSelectSure assay, limit of detection was 0.82 ng/mL. As seen in FIG. 13, mock elution results indicated the need for additional cleaning of the columns.

The following clean-in-place (CIP) procedure was tested.
I. 3 CV Equilibration Buffer
II. 2 CV 0.5 N NaOH
   10 minute static hold
III. 1 CV 0.5 N NaOH
   10 minute static hold
IV. 1 CV 0.5 N NaOH
V. Post-cleaning mock run Samples were conditioned with low concentration of detergent (0.1% polysorbate 20, 0.05% sodium azide) to prevent sample from sticking to the wall of the container. Samples were adjusted to neutral pH prior to loading on the column. MAbA and MAbB were loaded onto cation exchange columns (POROS) or anion exchange columns (QSFF). Following normal elution, the columns were cleaned using the protocol described above. A second set of columns were loaded with MAbA or MAb B but following elution, were not cleaned using the above protocol. All columns were then subject to a "mock elution". Mock eluates were analyzed for the presence of intact IgG were analyzed by ELISA.

Figure 14A:
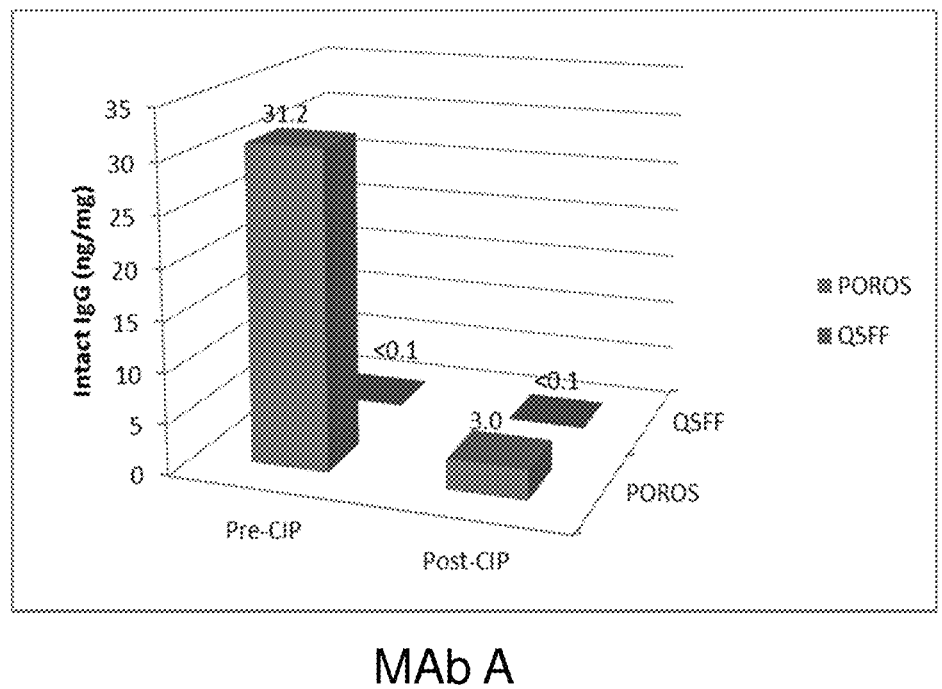
FIG. 14A shows the results intact IgG carryover detected following mock elutions of a cation exchange column (POROS) and an anion exchange column (QSFF) before and after a clean-in-place procedure. MAbA had previously been loaded and eluted from the columns.
Figure 14B:
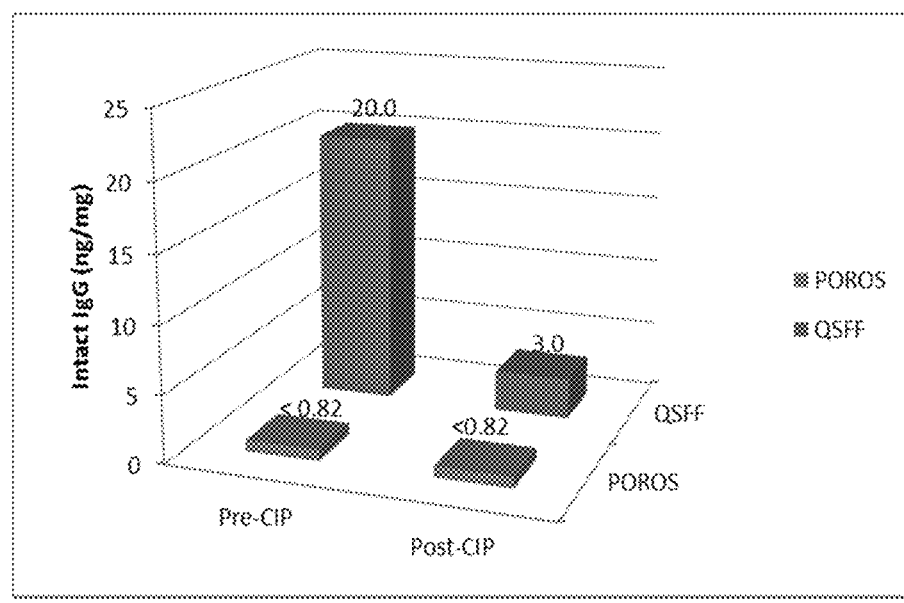
FIG. 14B shows the results intact IgG carryover detected following mock elutions of a cation exchange column (POROS) and an anion exchange column (QSFF) before and after a clean-in-place procedure. MAbB had previously been loaded and eluted from the columns.

As shown in FIG. 14, the cleaning method significantly reduced the protein carryover of MAbA in the POROS column (panel A) and significantly reduced the protein carryover of MAbB in the QSFF column (panel B). Little MAbA carryover was seen, even without a CIP step, with the QSFF column (panel A) and little MAbB carryover was seen, even without a CIP step, with the POROS column (panel B).

Figure 15:
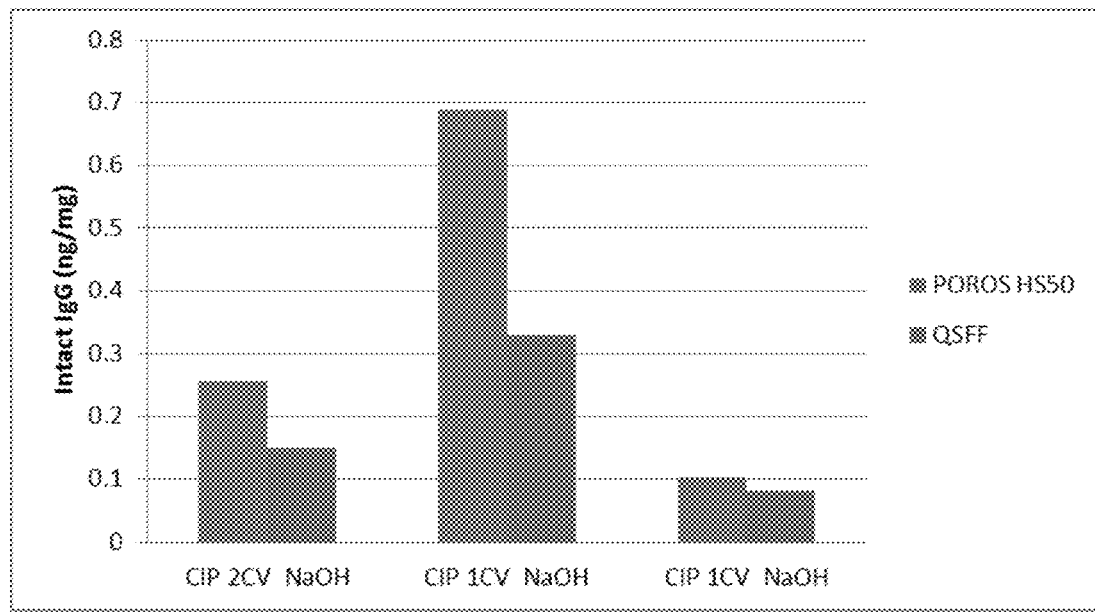
FIG. 15 shows the amount of intact IgG (MAbC) eluting from a POROS or QSFF column at the end of selected steps of the cleaning protocol.

A third antibody, MAbC was applied to POROS and QSFF columns and the amount of intact IgG eluting from the column at the end of selected steps of the cleaning protocol was measured (FIG. 15) such that by the end of the CIP cycle, the amount of protein carryover was less than 0.1 ppm. Protein carryover in a mock elution pool was also less than 0.1 ppm.

Figure 16:
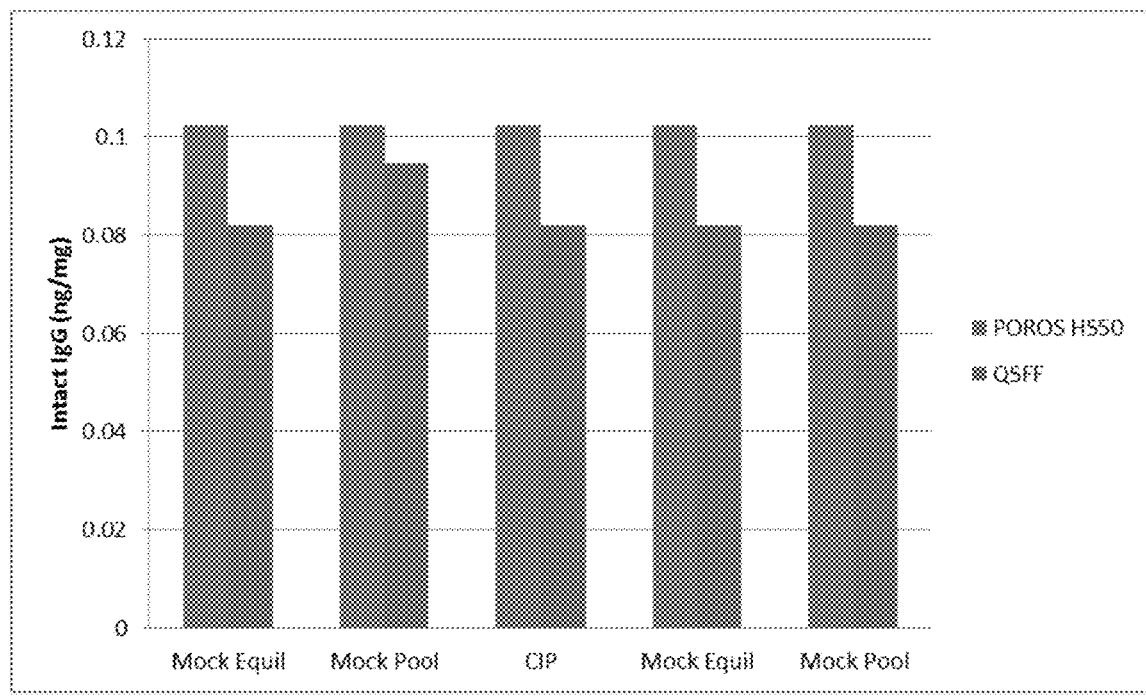
FIG. 16 shows MAbD carryover at different steps of the cleaning protocol on pilot scale columns.

To determine if the cleaning protocol would be effective on ion exchange chromatography columns at scale, the cleaning protocol was performed on pilot scale columns that had been previously loaded with MAbD. The columns were a 7.22 L POROS HS50 column and a 1.57 L QSFF column. Following loading and elution of MAbD, the columns were mock equilibrated without cleaning and then mock eluted. The columns were then cleaned according to the CIP protocol described above followed by additional mock equilibration and mock elution. Samples from each step were removed and analyzed for intact IgG as described above. Results are shown in FIG. 16. For both the POROS HS50 column and the QSFF column, the protein carryover was less than about 0.1 ppm.

Example 3. Evaluation of ProSep A Column for Multi-Product Use

Different cleaning solutions were evaluated at small scale in order to assess which solutions were most effective at reducing product carryover. Several different categories of solutions were tested, including acids, chaotropes, salts, and organic solvents. This study was designed to follow the standard protein A antibody process in order to best mimic generic process conditions, although actual processing conditions may differ depending on the specific product used.

Flow was directed in a downflow direction through the column for all processes with the exception of the cleaning cycle. Throughout the cleaning cycle, flow was directed upwards through the column in hopes of creating a best case cleaning scenario. Since feedstock is directed through the column in a downward direction during the loading cycle, the top of the Protein A column would theoretically foul the most. By directing flow of the cleaning cycle upwards, the theory is that the carryover and other impurities built up at the top of the column would not have to traverse through the entire column length before eluting out. At the time of this study, it was not clear if upflow was any more beneficial at cleaning the column than downflow. For the purposes of this section, since all experiments were consistent in using upflow, comparisons can still be made between the different cleaning solutions despite this finding.

Materials and Methods
Protein a Chromatography Processing

Protein A chromatography was performed using an ÄKTAexplorer 100 chromatography system (Amersham Pharmacia Biotech) and Unicorn 5.10 control software (GE Healthcare). ProSep A resin was used in substitute of ProSep vA resin. Performances of the two resins have previously been shown to be equivalent. The resin was packed in a 0.66 cm diameter Omnifit glass column to a bed height of 14 cm. Naïve resin was packed for every run. All experiments were performed at room temperature (20-30° C.). MAb1 and mAb2 harvested cell culture fluid (HCCF) were used. The standard protein A antibody process was maintained with flow rates at 30 CV/hr, load capacity at 14 g/L resin, and pooling from 0.5 OD to a final volume of 2 CV based on UV absorbance at 280 nm.

A precycle of elution and regeneration was followed by loading cycles consisting of equilibration, antibody load, three washes, elution/pooling, and regeneration. Nine loading cycles were run sequentially to sufficiently foul the column. A cleaning cycle followed consisting of an extension of regeneration, equilibration, 10 CVs of the cleaning agent to be tested, and regeneration. This cleaning cycle was run in an upflow direction using a slower flow rate of 10 CV/hr. 1 CV fractions were collected throughout the cleaning solution block. The column was then stored before running a series of mock runs (carryover cycles) to evaluate the product carryover. An integrity check consisting of a precycle, normal loading cycle, and storage followed the mock run to ensure that protein yields did not decrease. Each experiment was performed in duplicate.

A mock run is defined as a run in which the usual phases of each process step are followed with the exception of the load phase, during which no protein is loaded onto the column. Instead, Phosphate Buffered Saline (PBS) is loaded onto the column (mock load) to simulate the volume, pH, and conductivity of a normal load pool with protein. Carryover sample pools (mock pools) were collected from the mock run at the same starting volume where a normal protein elution pool would have been collected.

The overall process flow is summarized as follows:

| Precycle | |
|---|---|
| Elution | 3 CV |
| Regeneration | 3 CV |
| Loading Cycle (×9) | |
| Equilibration | 4 CV |
| Load with HCCF | 14 g/L |
| Wash 1 | 3 CV |
| Wash 2 | 3 CV |
| Wash 3 | 3 CV |
| Elution/Pool | 3 CV |
| Regeneration | 3 CV |
| Cleaning Cycle | |
| Regeneration | 7 CV |
| Equilibration | 5 CV |
| Cleaning Agent | 10 CV |
| Regeneration | 10 CV |
| Storage | 5 CV |
| Precycle | |
| Mock Run | |
| Loading cycle (PBS load) | |
| Integrity Check | |
| Loading cycle (HCCF load) | |
| Storage | |

Buffer components are shown in Table 7.

TABLE 7

Compositions of buffers used in Protein A chromatography processing.

| Buffer Name | Buffer Components |
|---|---|
| Equilibration | 25 mM Tris, 25 mM NaCl, 5 mM EDTA, pH 7.1 |
| Elution | 0.1M Acetic Acid, pH 2.9 |
| Regeneration | 0.1M Phosphoric Acid |
| Wash 2 | 0.4M Potassium Phosphate, pH 7.0 |
| Cleaning | Varies |
| Mock Load | Phosphate Buffered Saline (PBS) |
| Storage | 2% Benzyl Alcohol, 0.1M Na Acetate, pH 5.0 |

Cleaning agent compositions are shown in Table 8.

TABLE 8

Composition of cleaning agents

| Cleaning Agent | pH | Conductivity (mS/cm) |
|---|---|---|
| 25 mM Tris, 25 mM NaCl, 5 mM EDTA (Equilibration Buffer) | 7.1 | 5.5 |
| 1% v/v Phosphoric Acid | 1.5 | 15.5 |
| 0.1M Acetic Acid (Elution Buffer) | 2.9 | .5 |
| 19% Ethanol | 5.2 | 33,200.0 |
| 0.1M Imidazole/19% Ethanol | 7.5 | 1,061,000.0 |
| 2M Arginine HCl | 3.8 | 50.1 |
| 20% Hexylene Glycol | 5.4 | 1,937.5 |
| 2M Potassium Phosphate | 7.0 | 128.5 |
| 6M Guanidine HCl | 5.0 | 284.0 |
| 8M Urea/1M NaCl | 8.2 | 52.8 |

Post-Processing of Protein A Pools

Within 3 hours of elution, the cleaning fractions and carryover pools were conditioned with polysorbate 20 and sodium azide to a final concentration of 0.1% polysorbate 20 and 0.05% sodium azide. Polysorbate 20 is a detergent which prevents low levels of protein from adsorbing onto sample container walls and sodium azide is a preservative which prevents bacterial growth. The protein A pools (both protein and mock) were adjusted to pH 5.0 and the cleaning fractions were adjusted to between pH 5.0-7.0 using 1.5 M TRIS base. All samples were stored at 4° C. until analyzed for product (intact IgG).

Analytics

Protein pool concentrations were found using a UV spectrophotometer (Shimadzu) at an absorbance of 280 nm. Cleaning and mock pool samples were submitted in either duplicate or triplicate and analyzed for product using an Intact Human IgG ELISA.

The results from the Intact Human IgG ELISA were converted to carryover values using the following calculation:

$$\text{potential carryover (ng IgG/mg Product)} = \frac{\text{reported ELISA value (ng/mL)} \times \text{dilution factor}}{\text{lowest product concentration (mg/ml)}}$$

To represent the worst-case carryover, the lowest product concentrations from each experiment's protein pool samples were used for the carryover calculations (Table 9).

TABLE 9

Product Concentrations Used in the Carryover Calculations

| Cleaning Agent | Run # | Product Concentration Source (Cycle #) | Product Concentration (mg/mL) |
| --- | --- | --- | --- |
| Equilibration Buffer | 1 | 9 | 6.98 |
|  | 2 | 4 | 6.05 |
| 1% v/v Phosphoric Acid | 1 | 2 | 5.86 |
|  | 2 | 8 | 5.94 |
| 0.1M Acetic Acid | 1 | 1 | 6.27 |
|  | 2 | 3 | 6.18 |
| 19% Ethanol | 1 | 8 | 6.99 |
|  | 2 | 9 | 6.06 |
| 0.1M Imidazole/19% Ethanol | 1 | 8 | 6.84 |
|  | 2 | 2 | 6.00 |
| 2M Arginine HCl | 1 | 2 | 6.22 |
|  | 2 | 8 | 5.27 |
| 20% Hexylene Glycol | 1 | 9 | 6.24 |
|  | 2 | 9 | 5.37 |
| 2M Potassium Phosphate | 1 | 5 | 5.85 |
|  | 2 | 1 | 7.53 |
| 6M Guanidine HCl | 1 | 9 | 6.88 |
|  | 2 | 8 | 6.30 |
| 8M Urea/1M NaCl | 1 | 4 | 5.81 |
|  | 2 | 5 | 6.86 |

Results

Figure 17:
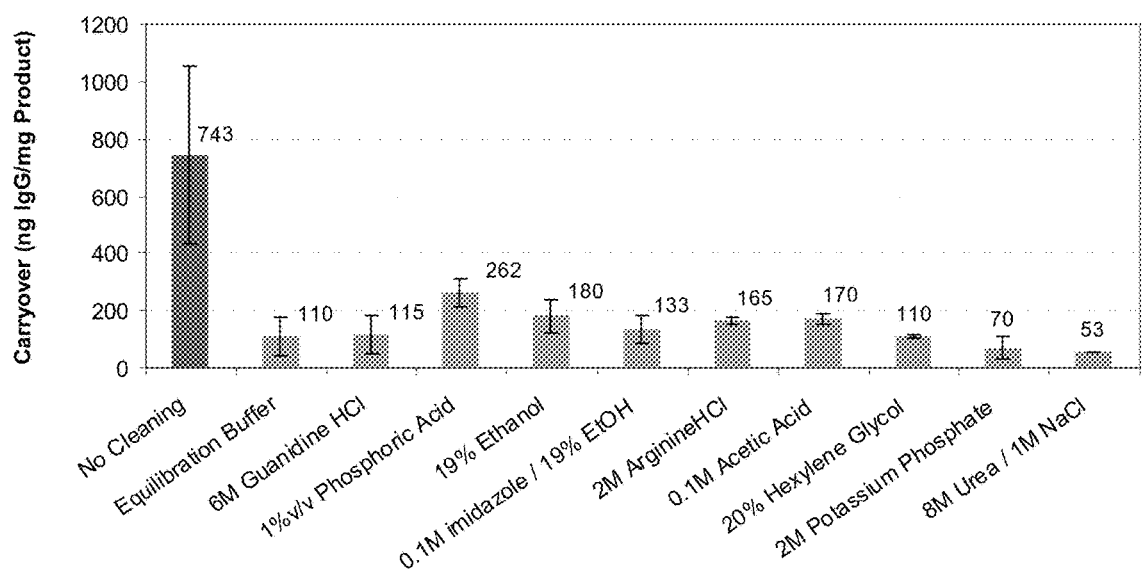
FIG. 17 shows a plot of intact human IgG carryovers as a function of different wash conditions.

The carryover results from the cleaning solution screenings are summarized in FIG. 17. For comparison, two runs were performed where all of the processing steps were the same but no cleaning cycles were performed. When compared to a column that has not been cleaned, all of the columns exposed to cleaning solutions showed marked reduction of carryover. The average carryover decreased between 65-93% when compared to a column not exposed to the cleaning cycle.

Equilibration buffer was originally included as a negative control for the cleaning solutions since protein normally does not elute from a Protein A column when exposed to equilibration buffer. However, the equilibration buffer performed just as well as any of the other solutions in reducing carryover. This suggested that additional flowthrough of buffer through the column helped remove carryover, regardless of the actual solution composition.

A high variability between runs was seen for many of the different cleaning solutions. This variability could be due in part to the use of two different feedstocks throughout the experiments. MAb1 HCCF was used for one of the two runs from each of the following samples: No Cleaning, Equilibration Buffer, 6M Guanidine HCl, 1% v/v Phosphoric Acid, 19% Ethanol, 0.1M Imidazole/19% Ethanol; mAb2 HCCF was used for all other runs. Limited feedstock availability prevented the use of a consistent feedstock throughout all of the runs. However, inconsistent feedstock may not explain all of the variability seen since the 2 M Potassium Phosphate samples showed high variability despite the use of mAb2 HCCF for both runs (56.5% RSD).

An additional load cycle was performed after the carryover cycles of each run to assess performance of the column after cleaning. Product yields were consistent with the yields obtained during load cycles before exposure to cleaning agents (results not shown).

Figure 18:
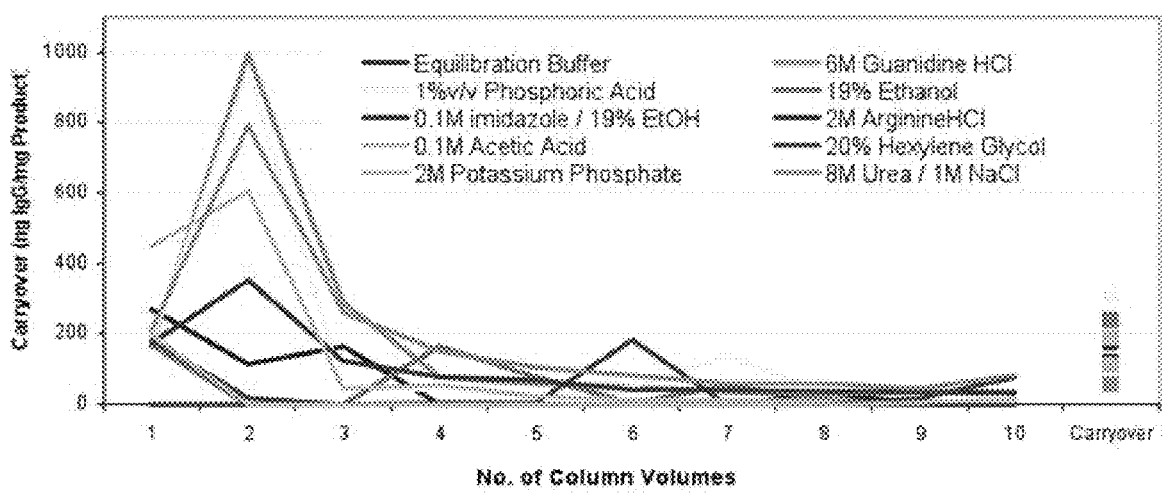
FIG. 18 shows a plot of protein carryover as a function of CV washes (resin cleaning efforts) with different buffer solutions on a ProSep® vA column Legend: 6 M guanidine HCl: magenta); 19% ethanol: red; 2 M arginine HCl: brown; 20% hexene glycol: grey; 8 M urea/1 M NaCl: orange; equilibration buffer: blue; 1% v/v phosphoric acid: yellow; 0.1 M Imidazole/19% Ethanol: black; 0.1 M Acetic acid: green; 2 M potassium phosphate: turquoise.

Fractions were collected across the cleaning agent block of the cleaning cycles in order to assess the amount of antibody coming out in the cleanings (FIG. 18). Because some of the cleaning agents may have had a denaturing effect on the proteins, the results were used to establish a trend rather than to find absolute quantities. All of the cleaning agents released antibody quantities that stabilized to low, nearly constant levels well within 10 CVs. In contrast, the carryovers that eluted out during the mock cycle remained at much higher concentrations. Even with buffers such as equilibration buffer where no protein degradation was expected, a higher level of carryover was observed despite low levels of antibody released from cleaning. These findings suggest that a simple reduction or extension of cleaning duration will not significantly affect carryover levels when this cleaning procedure is used.

Figure 19:
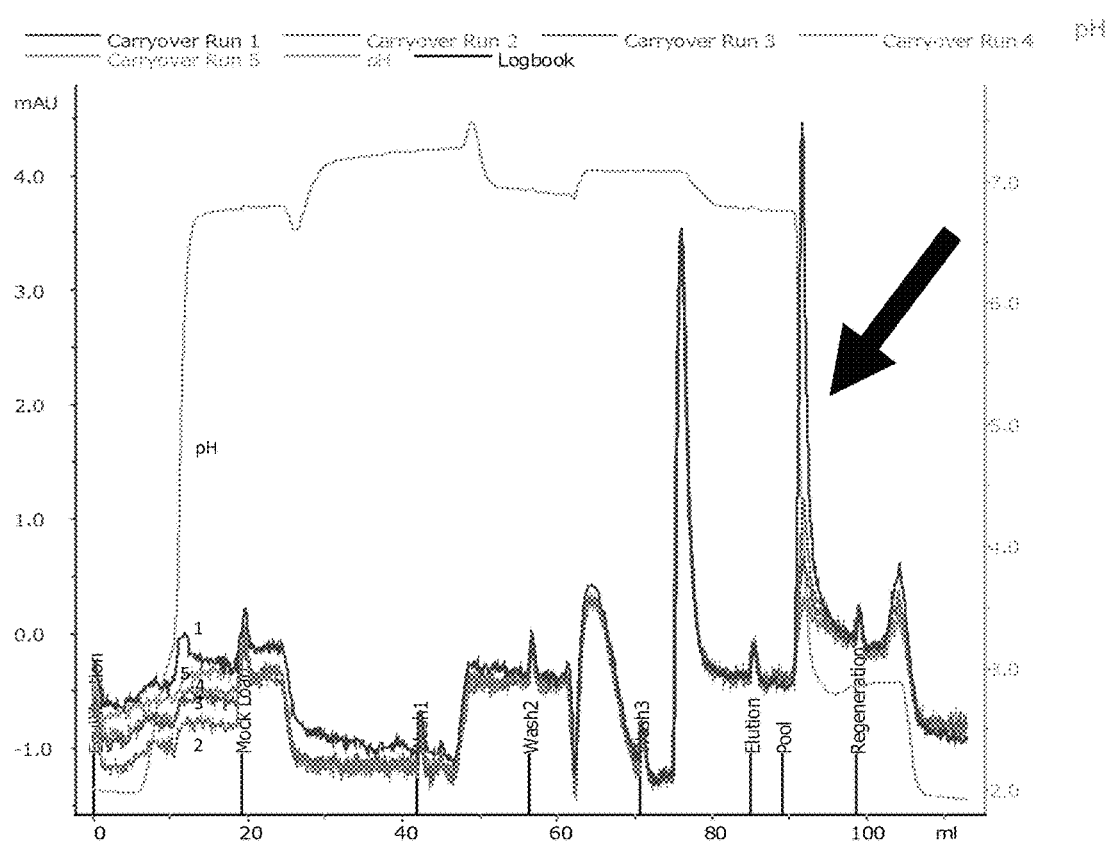
FIG. 19 is a chromatogram showing five consecutive mock runs of a 0.1 M acetic acid cleaning solution.
Figure 20:
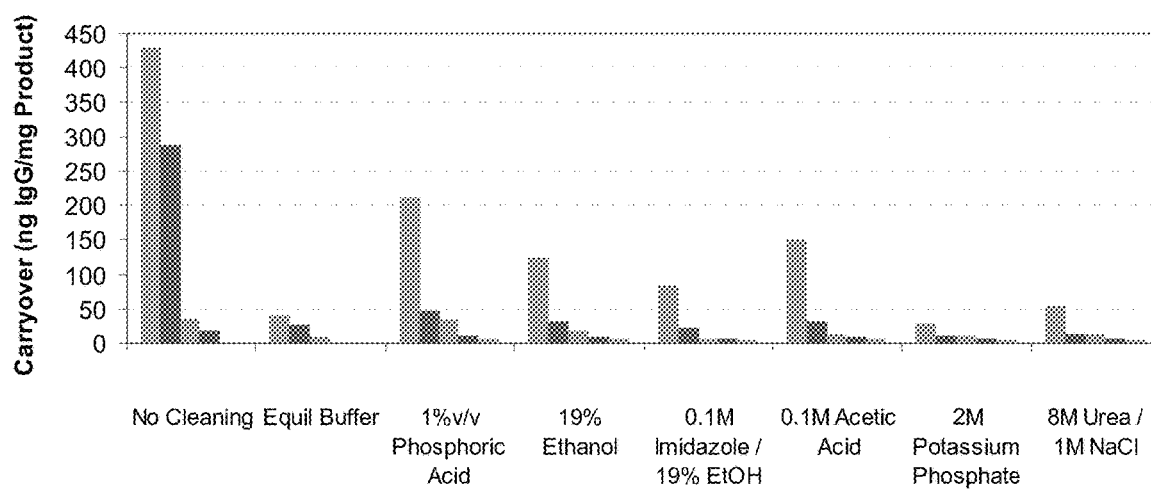
FIG. 20 is a chart showing carryover following consecutive mock runs with various cleaning solutions.
Figure 21:
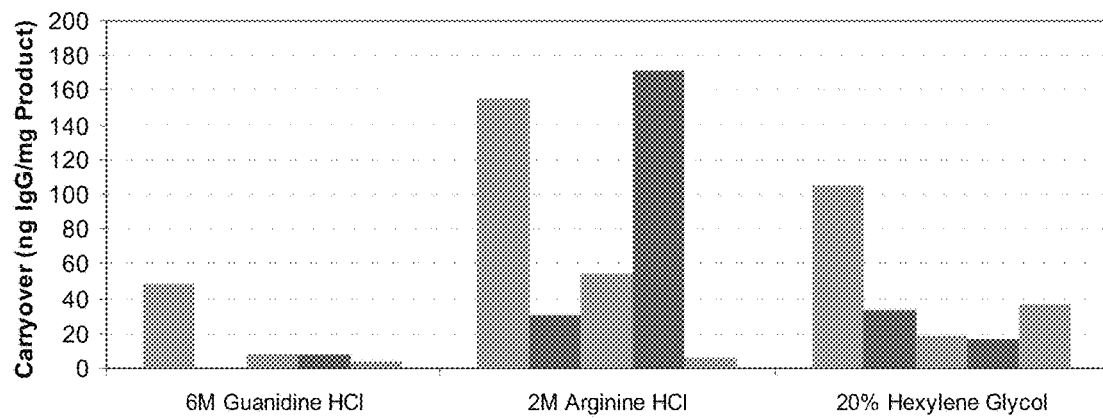
FIG. 21 is a chart showing carryover following consecutive mock runs with cleaning solutions 6 M guanidine hydrochloride, 2 M arginine hydrochloride, or 20% hexylene glycol.

Several consecutive mock runs were performed following the cleaning cycle for each solution tested. The UV280 nm signals from five consecutive mock runs of a 0.1 M Acetic Acid cleaning are shown overlaid in the chromatogram in FIG. 19. With every consecutive mock run performed, the sharp peak in the pooling region gradually decreased. This reduction of carryover with each consecutive cycle was not restricted to this particular column. As can be seen in FIG. 20, the same trend occurred with almost every cleaning solution that was screened. Even when no cleaning was done on the column, carryovers decreased significantly with each extra mock run performed. In FIG. 21, the 6M Guanidine HCl samples are missing data from the 2nd carryover, but the same trend was seen. The 20% Hexylene Glycol samples showed the same trend as well up until the 5th carryover. It has not been determined whether the high value of the 5th carryover reflects actual carryover results or human error in sampling.

The decrease in carryover with each consecutive mock run suggested that carryover could be reduced using standard Protein A buffers instead of more specialized cleaning agents such as those being screened. The use of existing buffers translates to easier implementation of these cleaning procedures in the purification pilot plant because less preparation time would be required for buffer batching and fewer uncertainties would exist about the effects of the chemicals on the column.

More importantly, these results also suggested pulsing of the mock run buffers as an alternative cleaning procedure for Protein A columns. Since the carryover was reduced more from consecutive mock runs than from continuous exposure to 0.1 M Acetic Acid or 1% v/v Phosphoric Acid, the low pH of the elution and regeneration buffers during the mock runs cannot wholly explain the improved cleaning. Instead, it is possible that the high-to-low pH transitions during the mock runs were responsible for the carryover reductions.

FIG. 21 shows that the 2 M Arginine HCl sample did not follow the carryover reduction trend. Power to the Akta system had been interrupted causing the column to be held in buffers after and possibly during the 3rd mock run. The increased carryover following the extended duration of buffer exposure indicated that a single carryover result may not be entirely indicative of how much protein remains on the column. The possibility of further carryover elution even after an initial result suggests a column is "clean" presents an important obstacle.

Ten different cleaning agents were screened in order to identify a suitable cleaning strategy that would reduce carryover in a Protein A column packed with ProSep A. All of the cleaning solutions helped reduce carryover; however, due to issues with variability, the majority of the agents showed similar performance. Carryover pools analyzed from consecutive mock runs showed a trend of decreased carryover with each additional mock run performed.

Example 4. Pulsing of High to Low pH Buffers

Studies were conducted to investigate pulsing of mock run buffers as a means of reducing product carryover. Once a basic strategy was identified, optimization was performed using larger small scale columns. Optimization parameters included analysis of flow directionality, flow rates, and static soaking.

Materials and Methods
Preliminary Analysis of Product Elution

Protein A chromatography was performed according to the methods described in Example 2 using mAb3 HCCF loaded at 15° C. Nine loading cycles were performed followed by storage, precycle, and two mock runs. No cleaning was performed. One CV fractions were collected across each of the mock runs and conditioned with TRIS base, polysorbate 20, and sodium azide as described previously. Fractions were analyzed by Intact Human IgG ELISA. pH pulsing and optimization All experiments were carried out using mAb3 HCCF on 1.6 cm diameter columns. Bed height remained at 14 cm. Nine loading cycles were performed followed by cleaning cycles consisting of 3 CVs of equilibration buffer and 3 CVs of regeneration buffer. Ten cleaning cycles were performed followed by storage, precycle, and a series of mock runs. One CV fractions were collected across the entire cleaning process. Cleaning fractions and mock pools were conditioned and analyzed as described previously.

Default cleaning procedures were run in a downflow direction at 30 CV/hr for ten cycles. Optimization studies involved modification of flow direction and flow rates, examination of static soaking conditions, and reduction of cleaning duration. For flow direction optimization, cleaning cycles were run in an upflow direction. For flow rate optimization, cleaning cycles were run at a flow rate of 15 CV/hr. Static soaking was examined by holding the column for three hours during the 4th cleaning cycle in either equilibration buffer or regeneration buffer. For optimization of static soaking, the column was held in equilibration buffer for three hours during four of the ten cleaning cycles. For optimization of cleaning duration, cleaning cycles were reduced to 2CVs of equilibration buffer and 2CVs of regeneration buffer. Additionally, static soaking in equilibration buffer was performed for five of the ten cleaning cycles. Optimization parameters are summarized in Table 10.

TABLE 10

Pulse Cleaning Optimization

| Optimization Parameter | Flow Rate | Flow Direction | Cycle Duration | Static Soaking |
|---|---|---|---|---|
| Preliminary pH Pulsing | 30 CV/hr | Downflow | 3 CV/buffer | N/A |
| Flow Direction | 30 CV/hr | Upflow | 3 CV/buffer | N/A |
| Flow Rate | 15 CV/hr | Downflow | 3 CV/buffer | N/A |
| Static Soaking | 30 CV/hr | Downflow | 3 CV/buffer | 3 hrs in Equil Buffer |
| Static Soaking | 30 CV/hr | Downflow | 3 CV/buffer | 3 hrs in Regen Buffer |
| Static Soaking | 30 CV/hr | Downflow | 3 CV/buffer | 4 Cycles-3 hrs in Equil Buffer |
| Cycle Duration | 30 CV/hr | Downflow | 2 CV/buffer | 5 Cycles-3 hrs in Equil Buffer |

Results

Figure 22:
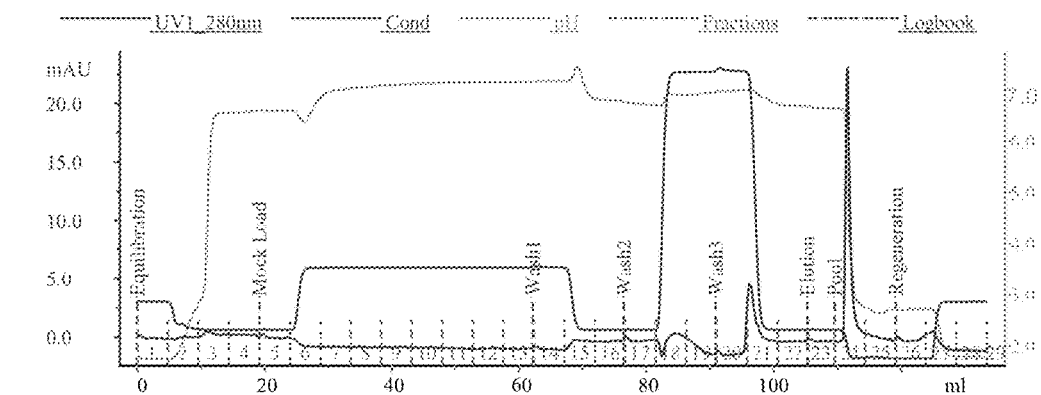
FIG. 22 shows a chromatogram of product elution without column cleaning (top panel). Carryover in each fraction is shown in the bottom panel.
Figure 22:
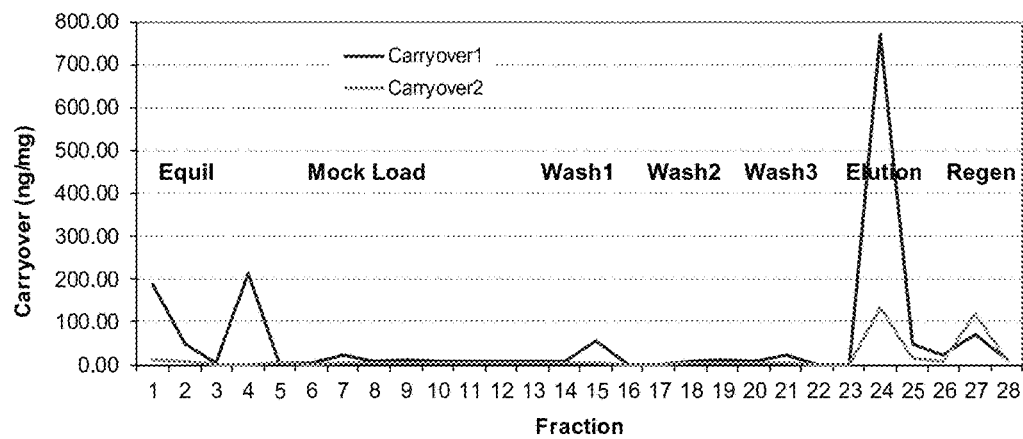

Fractions were collected across the first two mock run cycles of a fouled column to investigate when during the mock run cycle product actually elutes out. The chromatogram and carryover results are shown in FIG. 22. The majority of the product eluted at the high to low pH transition when the equilibration buffer was replaced by elution buffer. Product also eluted out to a lesser degree at the next pH drop when regeneration buffer replaced the elution buffer. These observations were repeated with the second carryover cycle. The carryover results confirmed that just holding the column at a low pH would not effectively clean the column. If the only requirement was low pH, the peaks during the 2nd carryover cycle should have been smaller and more protein should have come off during the entire elution and regeneration blocks of the first carryover cycle.

Figure 23:
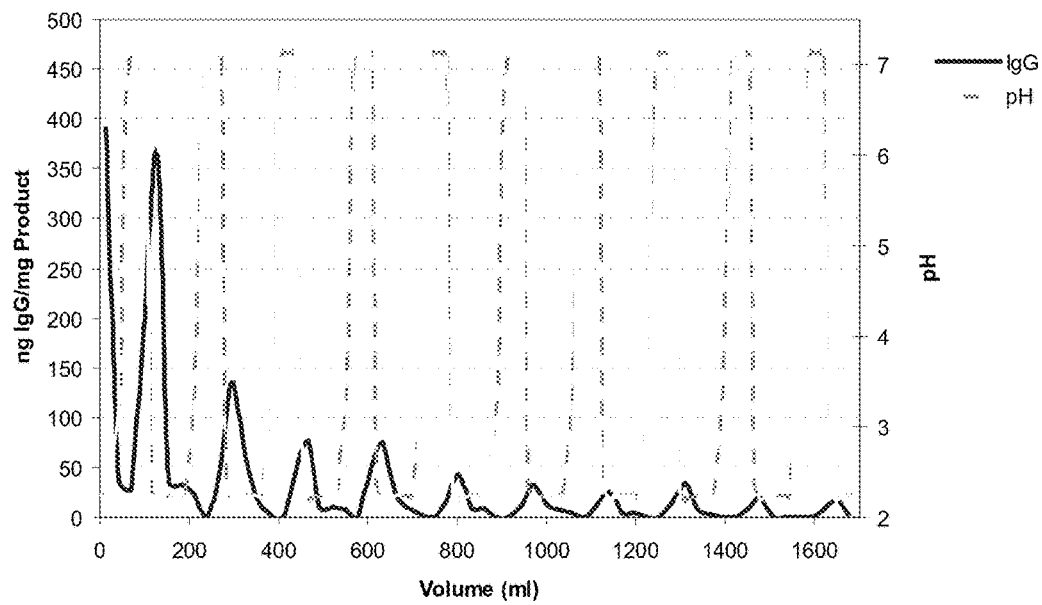
FIG. 23 shows product elution throughout pulse cleaning.

The combination of elution from the pH drops and additional elution during the second mock run strongly supported pulses of high-to-low pH as a potential cleaning strategy. Since protein elution peaked within three CVs of elution buffer, the buffer durations were set to three CVs for each of the high and low pH buffers. Equilibration buffer (pH 7.1) was chosen as the high pH buffer and regeneration buffer (pH 1.7) was chosen as the low pH buffer. pH pulsing Product elution throughout ten pulsing cycles of equilibration and regeneration buffers is shown in FIG. 23. Peaks of IgG elution from the column were present at every high-to-low pH transition of the cleaning. With each subsequent cycle, the quantity of protein eluting off decreased.

Figure 24:
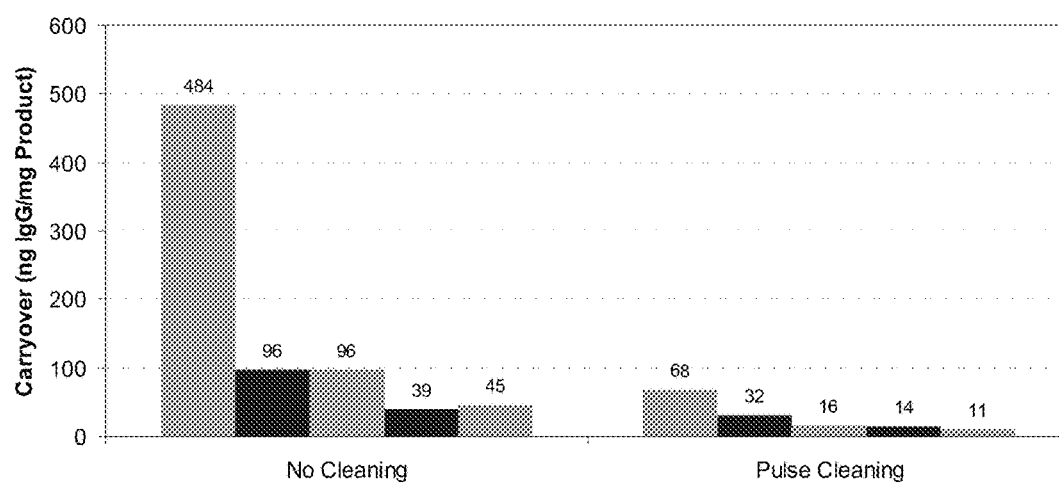
FIG. 24 is a graph showing carryover over consecutive mock runs with or without pulse cleaning.

Several consecutive mock runs were performed following the pulse cleaning. The carryover quantities from five consecutive mock runs are shown in FIG. 24. For comparison, consecutive carryovers are also shown from a column that had not been cleaned. The ten cycles of pH pulse cleaning resulted in an 86% reduction of carryover from the column, from 484 ng IgG/mg Product to 68 ng IgG/mg Product. Although cleaning resulted in marked reduction of carryover, additional mock runs still produced carryover. Optimization was needed to further reduce carryover.

Optimization of Pulse Cleaning

Figure 25:
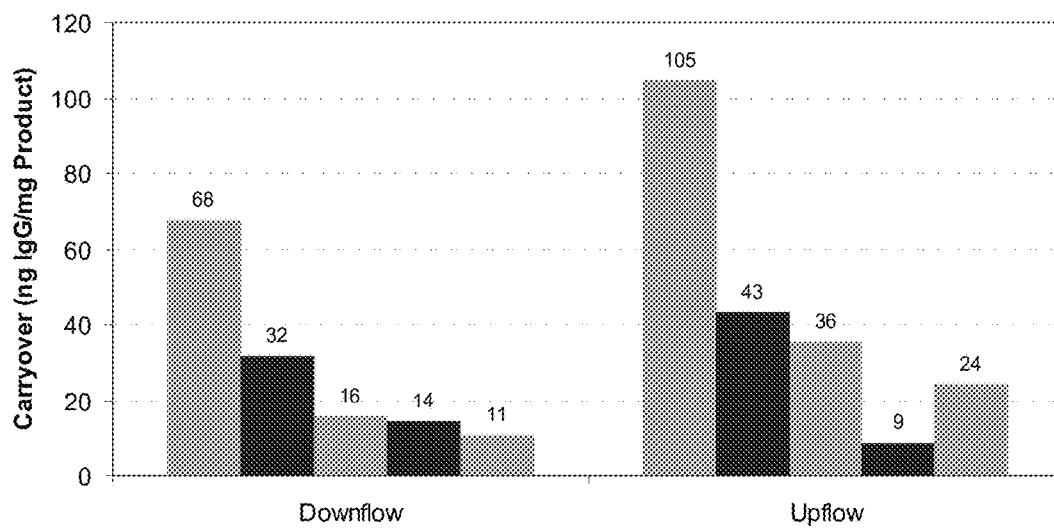
FIG. 25 is a graph showing carryover over consecutive mock runs using either downflow or upflow conditions.
Figure 26:
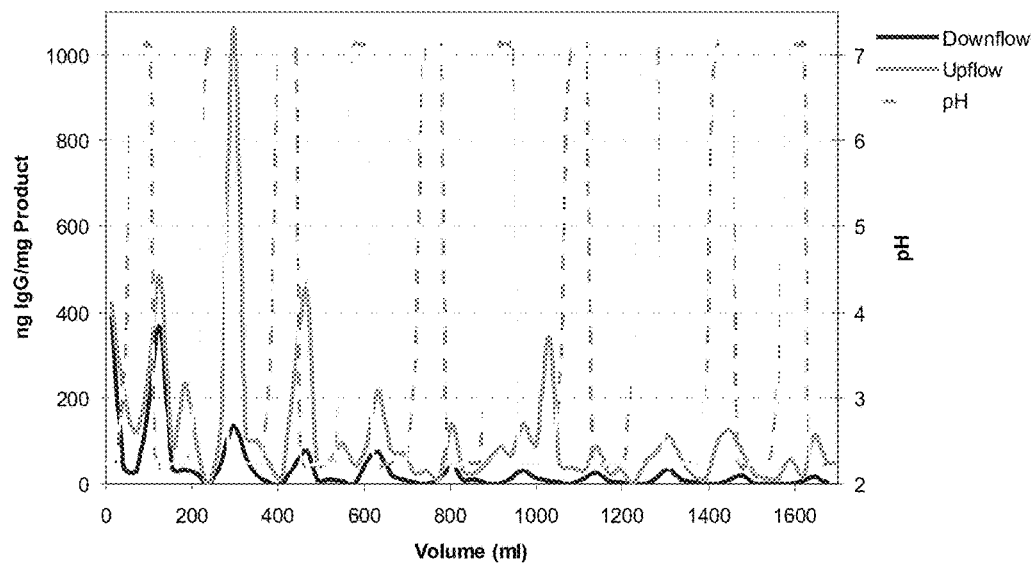
FIG. 26 shows a chromatogram of product elution throughout pulse cleaning. Black line shows downflow conditions, gray line shows upflow conditions, light gray shows pH.

Upflow and downflow of buffers through the column during the cleaning cycles were compared. The carryovers for five consecutive mock runs are shown in FIG. 25. Upflow resulted in a 54% increase in initial carryover when compared to downflow (105 ng IgG/mg Product vs. 68 ng IgG/mg Product). All subsequent carryovers showed an increase in carryover as well. The carryover during the fourth mock run was invalid because polysorbate 20 and sodium azide were mistakenly not added to the sample. FIG. 26 shows product elution throughout the entire cleaning duration for both upflow and downflow columns. While upflow resulted in more mock run carryover, it also caused more protein to elute off of the column throughout the ten cleaning cycles, effectively cleaning the column more thoroughly. Since a notable quantity of protein was still eluting off the column during the last cleaning cycle, the upflow run could arguably be extended with more cycles to remove more of the product eluting off as carryover.

Figure 27:
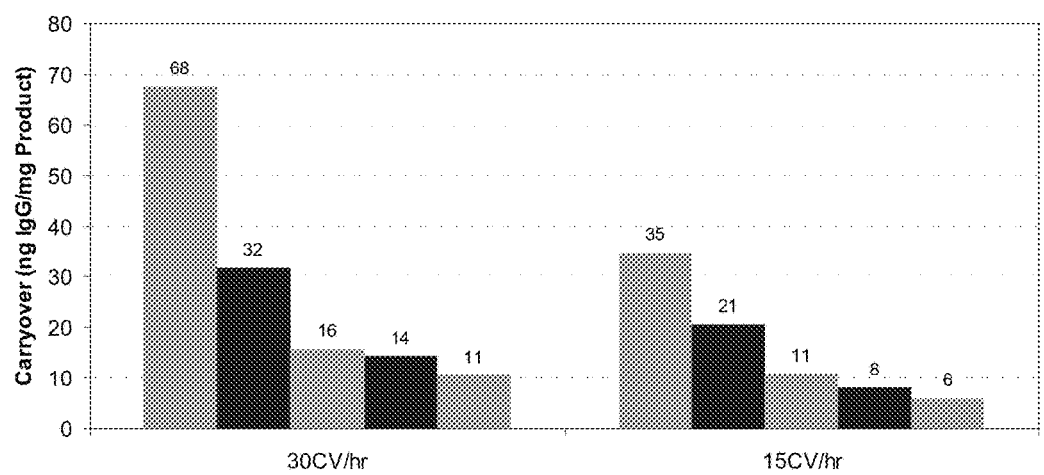
FIG. 27 shows carryover over consecutive mock runs at flow rates of 30 CV/hr and 15 CV/hr.

The effect of buffer flow rate during cleaning on mock run carryover levels is shown in FIG. 27. Reducing the flow rate in half from 30 CV/hr to 15 CV/hr reduced the initial carryover by nearly 50% (from 68 ng IgG/mg Product to 35 ng IgG/mg Product). While the slower flow rate effectively cut the carryover in half, the disadvantage was a doubling of cleaning time.

Figure 28:
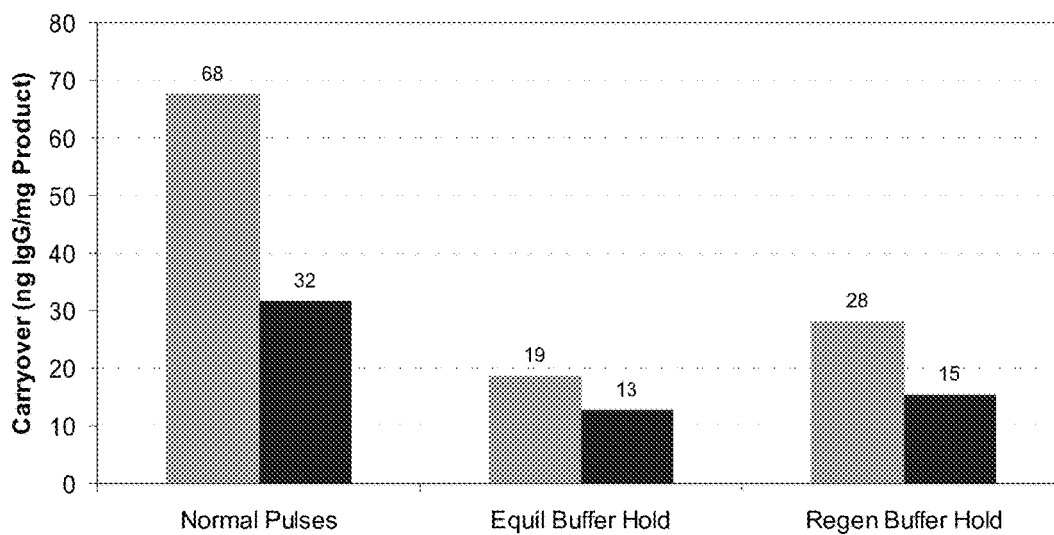
FIG. 28 shows carryover over consecutive mock runs with single static holds with equilibration buffer or regeneration buffer. Normal pulses represent samples with no static hold.

Results from static soaking of the column in buffer during the cleaning cycle are shown in FIG. 28. The column was held for three hours in either equilibration buffer or regeneration buffer and multiple carryovers were assessed. Soaking the column in equilibration buffer outperformed soaking of the column in regeneration buffer (19 ng IgG/mg Product vs. 28 ng IgG/mg Product). Both static soakings were a noticeable improvement to the 68 ng IgG/mg Product from normal pulse cleaning of the column. As with flow rate reduction, the disadvantage of increased cleaning time needed to be weighed against the advantage of carryover reduction.

Figure 29:
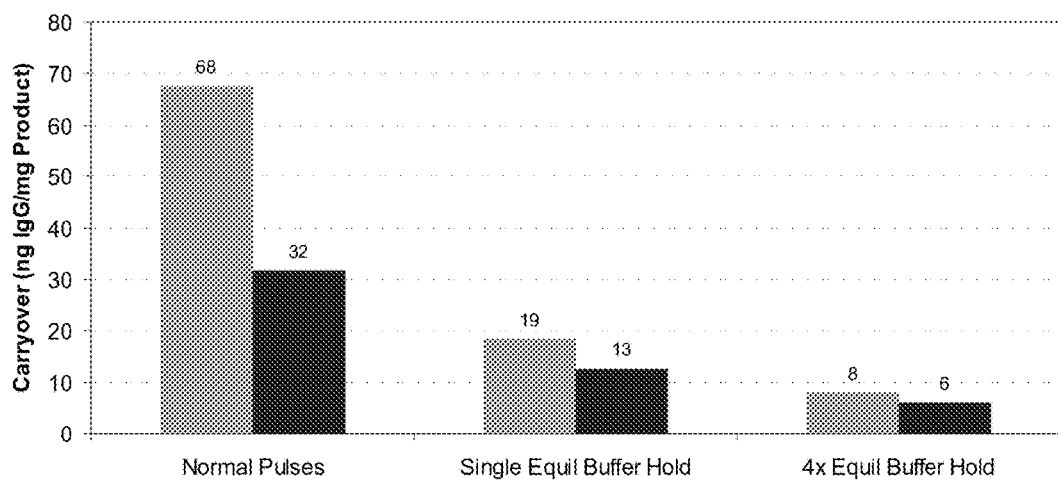
FIG. 29 shows carryover over consecutive mock runs with multiple static holds with equilibration buffer. Normal pulses represent samples with no static hold.
Figure 30:
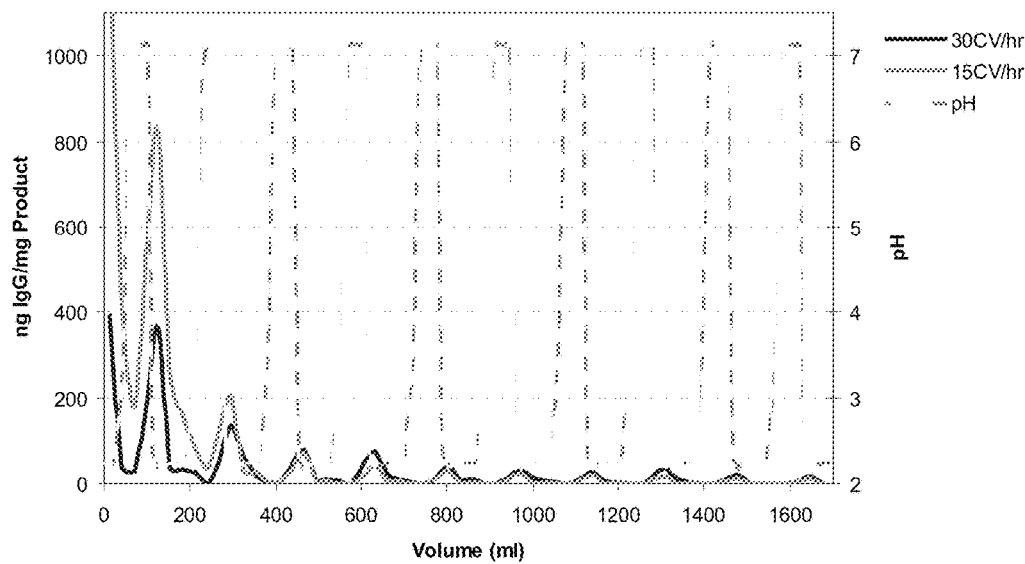
FIG. 30 shows a chromatogram showing product elution throughout the pulse cleaning. Black line shows 30 CV/hr conditions, gray line shows 15 CV/hr conditions, light gray shows pH.
Figure 31:
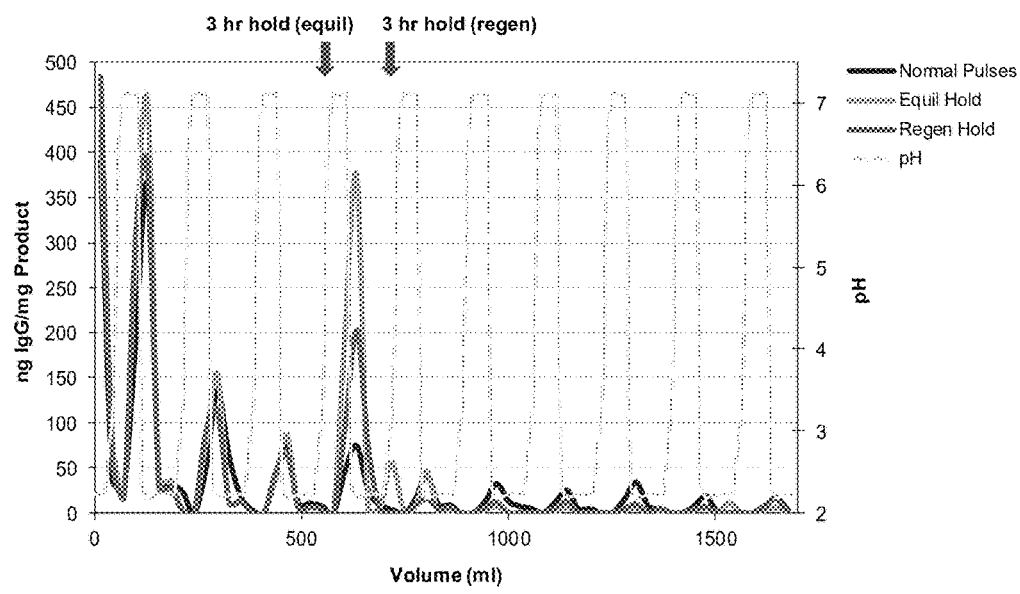
FIG. 31 shows a chromatogram showing product elution throughout the pulse cleaning with static holds. Black line shows normal pulses, medium gray line shows equilibration buffer hold conditions, dark gray shows regeneration buffer hold conditions, and light gray line shows pH.
Figure 32:
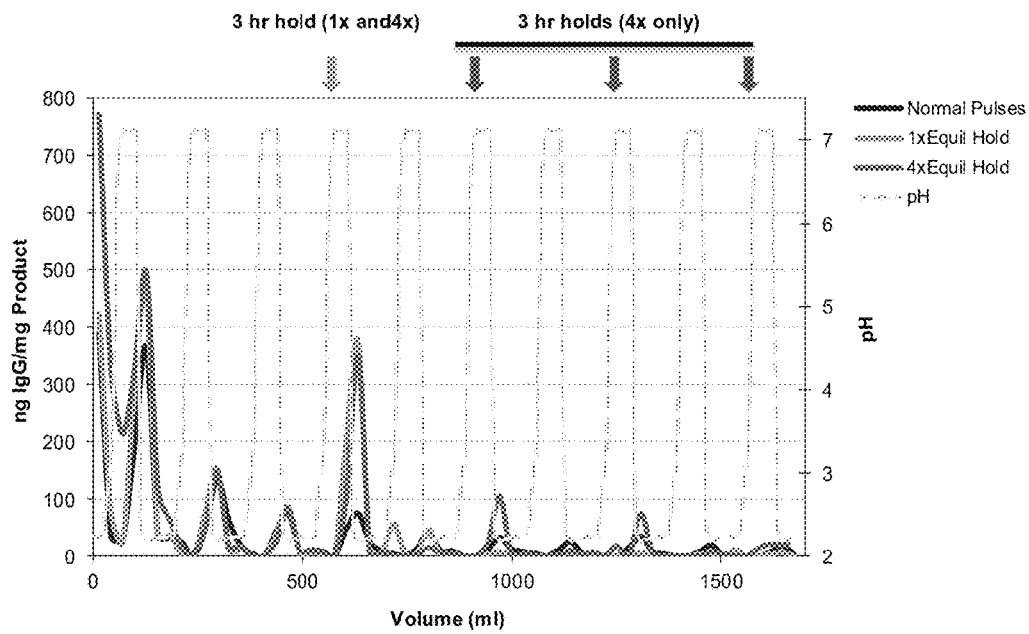
FIG. 32 shows a chromatogram showing product elution throughout the pulse cleaning with single or multiple static holds. Black line shows normal pulses, medium gray line shows 1× equilibration buffer hold conditions, dark gray shows 4× equilibration buffer hold conditions, and light gray line shows pH.

Static soaking of the column in buffer was assessed further by comparing a single three hour hold in equilibration buffer to multiple three hour holds. The column was held in a static soak for four of the ten pulsing cycles and evaluated for carryover (FIG. 29). With the multiple static soaks, carryover dropped from 19 ng IgG/mg Product to 8 ng IgG/mg Product.

Figure 33:
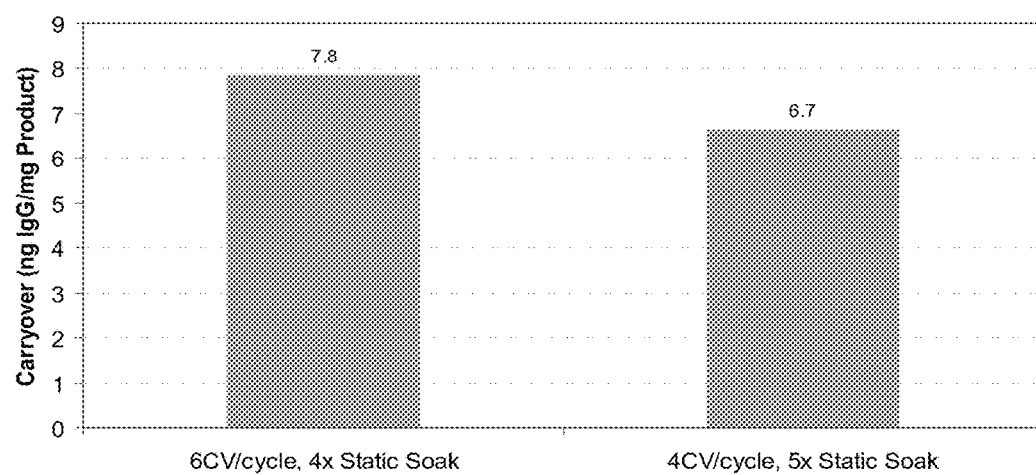
FIG. 33 shows reduced cycle duration effect on carryover under pulse cleaning conditions.
Figure 34:
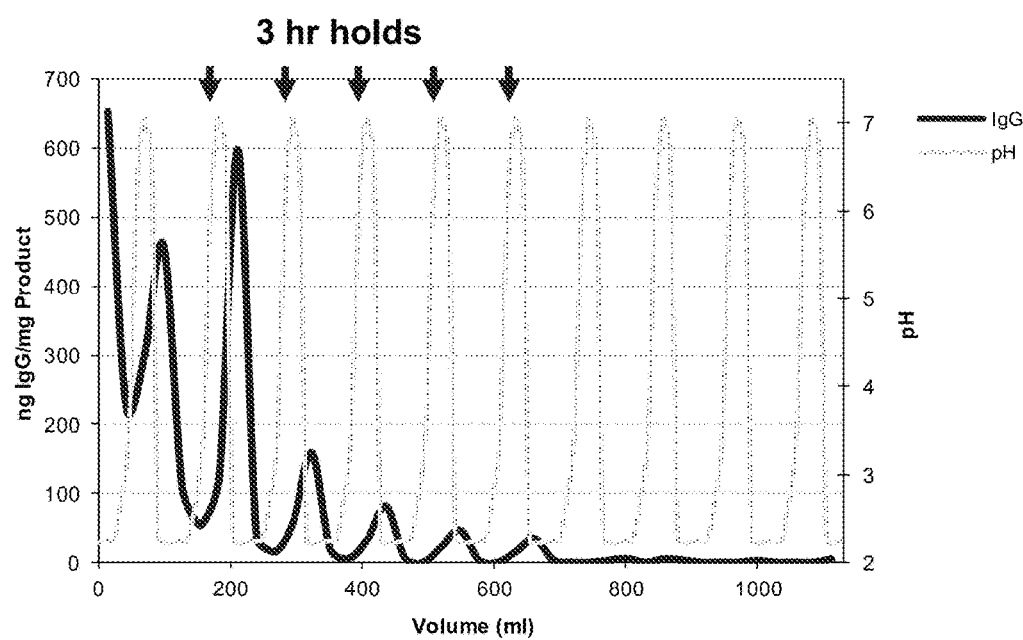
FIG. 34 shows a chromatogram showing product elution throughout the pulse cleaning with reduced cycle duration. Black line shows IgG and light gray line shows pH.

Fractions collected throughout the cleaning cycles for each of the optimization runs were assessed for product elution in order to determine optimal cleaning durations (FIGS. 23, 26, 30-32). The majority of the cleaning cycles showed little or no product elution during the third CVs of both equilibration and regeneration buffers. Consequently, the duration of each cleaning cycle was reduced to two CVs equilibration buffer and two CVs regeneration buffer. This reduction of cleaning duration translated to less buffer and shorter cleaning times; however, product carryover would either remain the same or increase slightly. To reduce carryover further while maintaining smaller buffer volumes, the number of static soakings was increased from four to five. FIG. 33 shows that these changes slightly reduced carryover from 7.8 ng IgG/mg Product to 6.7 ng IgG/mg Product. The product elution throughout column cleaning is shown in FIG. 34. By the end of the 10th cleaning cycle, 5.0 ng IgG/mg Product eluted out with the last column volume of regeneration buffer.

Example 5. Large-Scale Performance of Cleaning

The most promising pH pulse cleaning procedure identified during optimization studies was applied to previously used pilot scale columns. Columns for the study were chosen based upon molecule, dimensions, and number of previous protein contacts. Since only the Pharmacia skids allowed for automatic pause durations, columns were chosen that would not exceed the skids' flow rate cap of 2 L/min.

Materials and Methods

Previously used mAb4 and mAb5 Protein A columns were obtained from a pilot plant cold room storage. The mAb4 column measured 20 cm in diameter with a bed height of 13.5 cm and had been previously used for 28 cycles. Bioprocess skid 1538 (Amersham Biosciences Pharmacia) was used for cleaning and skid 1050 (Millipore) was used for the mock run. The mAb5 column (Pharmacia Index) measured 14 cm in diameter with a bed height of 15 cm and had been previously used for 20 cycles. Bioprocess skid 1076 (Amersham Pharmacia Biotech) was used for all mAb5 processes.

Ten cleaning cycles consisting of two CVs of equilibration buffer and two CVs of regeneration buffer were performed. The column was held in a 3 hour equilibration buffer static soak for five of the ten pulsing cycles. Cleaning was followed by storage of the column, sanitization of the skid, and a mock run. For the mAb5 column, an additional mock run without the column immediately followed sanitization to obtain a value for system carryover.

Mock run parameters were based on parameters previously used in Protein A processing of each specific molecule. For the mAb5 column, the wash 3 step was extended to four CVs per typical mAb5 Protein A chromatography. A summary of mock run parameters and the original runs used for reference are listed in Table 11.

TABLE 11

Parameters used in pilot plant scale mock runs

| Column ID/ Molecule | Parameter Source (Run Date) | Mock Load Volume (L) | Pool Collection Start Volume (L) | Product Concentration (g/L) |
|---|---|---|---|---|
| mAb4 | Dec. 19, 2007 | 41.2 | 4.9 | 7.06 |
| mAb5 | Nov. 16, 2007 | 56.9 | 3.6 | 4.95 |

Product carryovers are shown in Table 12. After cleaning, the aIGF1R column had a carryover of 48.2 ng IgG/mg Product while the antiAbeta column had a carryover of 8.6 ng IgG/mg Product. Previous studies have indicated that carryover values increase with increased protein contacts. Although the mAb4 column was exposed to eight more protein contacting cycles than the mAb5 column, the increased number of contacts alone may not be significant enough to explain the large disparity in carryover values.

TABLE 12

Results from pilot scale carryover studies

| Column | Carryover (ng IgG/mg Product) | Elution from Final CV of Cleaning (ng IgG/mg Product) | System Carryover (ng IgG/mg Product) |
|---|---|---|---|
| mAb4 | 48.2 | 12.7 | Not Assessed |
| mAb5 | 8.6 | 62.9 | 0.97 |

By the end of the final cleaning cycle, product was still eluting out with the cleaning buffer for both columns Compared to the 5.0 ng IgG/mg Product from the final cleaning CV observed during small scale optimization, the product elutions at pilot scale were higher than expected (12.7 and 62.9 ng IgG/mg Product for aIGF1R and antiAbeta columns, respectively).

System carryover was analyzed by performing a mock run with no column in place following skid sanitization. System carryover represents the amount of carryover attributable to the skid rather than to the Prosep A resin. While the cleaning procedure and sanitization of the skid should have eliminated all system carryover, 0.97 ng IgG/mg Product was still detected in the system mock pool during the mAb5 run. These results indicate that while system contribution to carryover was minimal, further cleaning of the skid itself may be necessary in order to ensure that absolutely no product carries over from one run to the next.

Application of the cleaning procedure used during small scale optimization to the pilot scale resulted in higher carryover levels with significant variability. Product continued to elute throughout the end of the cleaning cycle at higher levels than previously observed at the small scale as well. The system was found to contribute to small levels of carryover even when no column was in place.

Pulsing of buffers from high to low pH was found to be an effective means of reducing carryover at small scale. Using 1.6 cm diameter columns, carryover was reduced to 6.7 ng IgG/mg Product. However, application of the cleaning procedure to actual columns used during previous pilot runs resulted in much higher carryover values with the highest value so far measured at 48.2 ng IgG/mg Product. Although it is expected that carryover levels will differ somewhat between columns because of differences in column usage, the finalized cleaning procedure will need to ubiquitously eliminate carryover, regardless of the specifics of any given column. Additionally, it will be important to evaluate additional parameters such as long term column performance and minimum carryover detection limits.

What is claimed is:

1. A method to clean a chromatography material for reuse, the method comprising the steps of
    a) passing two or more material volumes of elution buffer through the material, wherein the elution buffer comprises about 0.15 M acetic acid and is about pH 2.9;
    b) statically holding the material in elution buffer for a time ranging from about 10 minutes to about 30 minutes;
    c) passing about two or more material volumes of elution buffer through the material; and
    d) passing about two or more material volumes of regeneration buffer through the material, wherein the regeneration buffer comprises about 0.1 N NaOH and is about pH 13;
    wherein the buffers are passed through the material at about 15 material volumes/hour.

2. A method to clean a chromatography material for reuse, the method comprising the steps of
    a) passing about two material volumes of elution buffer through the material, wherein the elution buffer comprises about 0.15 M acetic acid and is about pH 2.9;
    b) statically holding the material in elution buffer for about 30 minutes;
    c) passing about two material volumes of elution buffer through the material; and
        d) passing about four material volumes of regeneration buffer through the material, wherein the regeneration buffer comprises about 0.1 N NaOH and is about pH 13;
    wherein the buffers are passed through the material at about 15 material volumes/hour.

3. A method to clean a chromatography material for reuse, the method comprising the steps of
    a) passing about two material volumes of elution buffer through the material, wherein the elution buffer comprises about 0.15 M acetic acid and is about pH 2.9,
    b) statically holding the material in elution buffer for about 30 minutes,
    c) passing about two material volumes of elution buffer through the material, and
    d) passing about two and one-half material volumes of regeneration buffer through the material, wherein the regeneration buffer comprises about 0.1 N NaOH and is about pH 13,
    e) statically holding the material in regeneration buffer for about 30 minutes,
    f) passing about two and one-half material volumes of regeneration buffer through the material;
    wherein the buffers are passed through the material at about 15 material volumes/hour.

4. A method to clean a chromatography material for reuse, the method comprising the steps of
    a) passing about two material volumes of equilibration buffer through the material, wherein the equilibration buffer comprises about 25 mM Tris and about 25 mM NaCl and is about pH 7.1;
    b) statically holding the material in equilibration buffer for about 30 minutes;
    c) passing about two material volumes of equilibration buffer through the material;
    d) passing about two material volumes of elution buffer through the material, wherein the elution buffer comprises about 0.15 M Acetic acid and is about pH 2.8;
    e) statically holding the material in elution buffer for about 30 minutes;
    f) passing about two material volumes of elution buffer through the material;
    g) passing about two material volumes of regeneration buffer through the material, wherein the regeneration buffer comprises 0.1 N NaOH, pH 13;
    h) statically holding the material in regeneration buffer for about 30 minutes;
    i) passing about two material volumes of regeneration buffer through the material.

5. A method to clean a chromatography material for reuse, the method comprising the steps of
    a) passing about four material volumes of equilibration buffer through the material, wherein the equilibration buffer comprises about 25 mM Tris and about 25 mM NaCl and is pH 7.1;
    b) performing six cycles of the steps comprising
        i) passing about three material volumes of elution buffer through the material, wherein the elution buffer comprises about 0.15 M Acetic acid and is about pH 2.8;
        ii) statically holding the material in elution buffer for about 10 minutes;
        iii) passing about one material volume of elution buffer through the material;
        iv) passing about three material volumes of regeneration buffer through the material, wherein the regeneration buffer comprises about 0.1 N NaOH and is about pH 13;
        v) statically holding the material in regeneration buffer for about 10 minutes;
        vi) passing about one material volume of regeneration buffer through the material.

6. A method to clean a chromatography material for reuse, the method comprising six cycles of the steps of
  a) passing about three material volumes of elution buffer through the material, wherein the elution buffer comprises about 0.15 M Acetic acid and is about pH 2.8;
  b) statically holding the material in elution buffer for about 15 minutes;
  c) passing about one material volume of elution buffer through the material;
  d) passing about three material volumes of regeneration buffer through the material, wherein the regeneration buffer comprises about 0.1 N NaOH and is about pH 13;
  e) statically holding the material in regeneration buffer for about 15 minutes;
  f) passing about one material volume of regeneration buffer through the material;
  g) passing about three material volumes of storage buffer through the material, wherein the storage buffer comprises about 100 mM sodium acetate, about 2% benzyl alcohol, and is about pH 5.0;
  e) statically holding the material in storage buffer for about 15 minutes;
  f) passing about one material volume of storage buffer through the material;
  wherein the buffers are passed through the material at about 15 material volumes/hour.

7. The method of claim 5, wherein the chromatography material is in a chromatography column.

8. The method of claim 5, wherein the chromatography material is an affinity material.

9. The method of claim 8, wherein the affinity material is a protein A affinity material.

10. The method of claim 5, wherein the chromatography material is used for large-scale production of a polypeptide.

11. A method to clean a chromatography material for reuse, the method comprising the steps of
  a) passing about three material volumes of equilibration buffer through the material, wherein the equilibration buffer comprises about 40 mM sodium acetate and is about pH 5.5;
  b) passing about two material volumes of about 0.5 N NaOH through the material
  c) statically holding the material in about 0.5 N NaOH for about 10 minutes;
  d) passing about one material volume of about 0.5 N NaOH through the material; and
  e) statically holding the material in about 0.5 N NaOH for about 10 minutes;
  f) passing about one material volume of about 0.5 N NaOH through the material.

12. The method of claim 11, wherein the chromatography material is an ion exchange material.

13. The method of claim 12 herein the ion exchange material is a cation exchange material.

14. The method of claim 11, wherein the chromatography material is used for large-scale production of an antibody.

15. A method to clean a chromatography material for reuse, the method comprising the steps of
  a) passing about three material volumes of equilibration buffer through the material, wherein the equilibration buffer comprises about 50 mM Tris, 85 mM sodium acetate and is about pH 8.8 and about 8.6 mS/cm;
  b) passing about two material volumes of about 0.5 N NaOH through the material
  c) statically holding the material in about 0.5 N NaOH for about 10 minutes;
  d) passing about one material volume of about 0.5 N NaOH through the material; and
  e) statically holding the material in about 0.5 N NaOH for about 10 minutes;
  f) passing about one material volume of about 0.5 N NaOH through the material.

16. The method of claim 15, wherein the chromatography material is an ion exchange material.

17. The method of claim 16, wherein the ion exchange material is an anion exchange material.

18. The method of claim 5, wherein the buffer is passed through the material in a downflow direction or an upflow direction.

19. The method of claim 5, wherein the cleaning of the chromatography material is measured by running a mock elution after cleaning the chromatography material.

20. The method of claim 19, wherein an eluent of the mock elution comprising one or more of <0.25 mg/mL total protein, <1 ppm IgG fragments, <1 ppm leached protein A, <1 µg/mL CZE LIF, <1 ppm CHOP, and <1 pg/mL CHO DNA indicates effective cleaning of the material for multi-product use.

21. The method of claim 5, wherein the chromatography material is stable in alkali.

22. The method of claim 5, wherein the chromatography material is used to purify a polypeptide.

23. The method of claim 5, wherein the chromatography material is cleaned following purification of a first polypeptide and wherein the chromatography material is used to purify a second polypeptide following the cleaning.

24. The method of claim 23, wherein the first polypeptide is an antibody or immunoadhesin.

25. The method of claim 24, wherein the first polypeptide is an immunoadhesin.

26. The method of claim 24, wherein the first polypeptide is an antibody.

27. The method of claim 26, wherein the antibody is a monoclonal antibody.

28. The method of claim 27, wherein the monoclonal antibody is a chimeric antibody, humanized antibody, or human antibody.

29. The method of claim 28, wherein the monoclonal antibody is an IgG monoclonal antibody.

30. The method of claim 29, wherein the antibody is an antigen binding fragment.

31. The method of claim 30, wherein the antigen binding fragment is Fab fragment, a Fab' fragment, a F(ab')$_2$ fragment, a scFv, a di-scFv, a bi-scFv, a tandem (di, tri)-scFv, a Fv, a sdAb, a tri-functional antibody, a BiTE, a diabody or a triabody.

32. The method of claim 23, wherein the first polypeptide is an enzyme, a hormone, a fusion protein, an Fc-containing protein, an immunoconjugate, a cytokine or an interleukin.

33. The method of claim 23, wherein the first polypeptide is a first antibody or a first immunoadhesin and the second polypeptide is a second antibody or second immunoadhesin.

34. The method of claim 4, wherein the buffers are passed through the material at about 15 material volumes/hour.

35. The method of claim 5, wherein the buffers are passed through the material at about 15 material volumes/hour.

36. The method of claim 11, wherein the buffers are passed through the material at about 15 material volumes/hour.

* * * * *